(12) United States Patent
Power et al.

(10) Patent No.: US 10,201,559 B2
(45) Date of Patent: *Feb. 12, 2019

(54) COMPOSITIONS OF SELENOORGANIC COMPOUNDS AND METHODS OF USE THEREOF

(71) Applicant: Alltech, Inc., Nicholasville, KY (US)

(72) Inventors: Ronan Power, Lexington, KY (US); Zi-Jian Lan, Lexington, KY (US); Alexandros Yiannikouris, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 195 days.

This patent is subject to a terminal disclaimer.

(21) Appl. No.: 15/121,412

(22) PCT Filed: Mar. 14, 2014

(86) PCT No.: PCT/US2014/029542
§ 371 (c)(1),
(2) Date: Aug. 25, 2016

(87) PCT Pub. No.: WO2015/137983
PCT Pub. Date: Sep. 17, 2015

(65) Prior Publication Data
US 2016/0361338 A1    Dec. 15, 2016

(51) Int. Cl.
| | |
|---|---|
| *A01N 43/04* | (2006.01) |
| *A61K 31/70* | (2006.01) |
| *A61K 31/7135* | (2006.01) |
| *A61K 31/7076* | (2006.01) |
| *C07D 473/34* | (2006.01) |
| *A61K 31/28* | (2006.01) |
| *A61K 38/05* | (2006.01) |
| *A61K 38/28* | (2006.01) |
| *A61K 31/706* | (2006.01) |
| *A61K 31/7064* | (2006.01) |

(52) U.S. Cl.
CPC .......... *A61K 31/7135* (2013.01); *A61K 31/28* (2013.01); *A61K 31/7076* (2013.01); *A61K 38/05* (2013.01); *A61K 38/28* (2013.01); *C07D 473/34* (2013.01); *A61K 31/706* (2013.01); *A61K 31/7064* (2013.01)

(58) Field of Classification Search
None
See application file for complete search history.

(56) References Cited

U.S. PATENT DOCUMENTS

| | | | |
|---|---|---|---|
| 8,796,241 B2 | 8/2014 | Lubin et al. | |
| 8,865,763 B2 | 10/2014 | Lyons et al. | |
| 9,833,486 B2 | 12/2017 | Power et al. | |
| 2006/0093684 A1 | 5/2006 | Takeda et al. | |
| 2006/0198906 A1 | 9/2006 | Majeed et al. | |
| 2007/0077238 A1 | 4/2007 | Teo et al. | |
| 2007/0122491 A1 | 5/2007 | Lyons et al. | |
| 2008/0107755 A1 | 5/2008 | Lyons et al. | |
| 2012/0094947 A1 | 4/2012 | Lubin et al. | |
| 2015/0057243 A1 | 2/2015 | Zhou et al. | |
| 2016/0045533 A1 | 2/2016 | Power | |
| 2016/0082033 A1 | 3/2016 | Power | |
| 2016/0090397 A1 | 3/2016 | Zhou et al. | |
| 2016/0113977 A1 | 4/2016 | Power et al. | |
| 2016/0361338 A1 | 12/2016 | Power et al. | |

FOREIGN PATENT DOCUMENTS

| | | |
|---|---|---|
| WO | 2013151975 A1 | 10/2013 |
| WO | 2014144776 A1 | 9/2014 |
| WO | WO-2015137983 A1 | 9/2015 |

OTHER PUBLICATIONS

Lowell et al. Science (2005), vol. 307, pp. 384-387.*
Can et al. Biological Trace Element Research (2005), vol. 105, pp. 135-150.*
International Preliminary Report on Patentability for International Patent Application No. PCT/US2014/029542 dated Sep. 14, 2016, 7 pages.
Brennan, K. M., et al., "Effects of organic and inorganic dietary selenium supplementation on gene expression profiles in oviduct tissue from broiler-breeder hens," Animal Reproduction Science, 125 (2011) 180-188, avail. online Apr. 2011.
Preud'homme, H., et al., "Large Scale identification of selenium metabolites by online size-exclusion-reversed phase liquid chromatography with combined inductively coupled plasma (ICP-MS) and electrospray ionization linear trap-Orbitrap mass spectrometry (ESI-MS(n))", Metallomics, May 2012, vol. 4 (5), pp. 422-432.
Pieczenik, S. R., et al., "Mitochondrial dysfunction and molecular pathways of disease", Experimental and Molecular Pathology, 2007, vol. 83, pp. 84-92.
Pinto, A., et al., "Supranutritional selecnium induces alterations in molecular targets related to energy metabolism in skeletal muscle and visceral adipose tissue of pigs", Journal of Inorganic Biochemistry, 2012, vol. 114, pp. 47-54.
Amaudguilhem, C., et al., "Selenium metabolomics in yeast using complementary reversed-phase/hydrophilic ion interaction (HILIC) liquid chromatography-electrospray hybrid quadrupole trap/ Orbitrap mass spectrometry", Anal. Chim. Acta., Dec. 13, 2012 (757), pp. 26-38.
Ouerdane, L., et al., "Comprehensive speciation of low-molecular weight selenium metabolites in mustard seeds using HPLC-electrospray linear trap/Orbitrap tandem mass spectrometry", Metallomics, Sep. 2013, 5 (9), pp. 1294-1304.
Bierla, K., et al., "Comprehensive speciation of selenium in selenium-rich yeast", Trends in Analytical Chemistry, Dec. 2012, vol. 41, pp. 122-132.

(Continued)

Primary Examiner — Patrick T Lewis
(74) Attorney, Agent, or Firm — Choate, Hall & Stewart LLP; Brenda Herschbach Jarrell

(57) ABSTRACT

The present application relates to compositions comprising selenium compounds, such as 5'-Methylselenoadenosine, Se-Adenosyl-L-homocysteine, Gamma-glutamyl-methyl-seleno-cysteine, a compound of formula (I), formula (II), a compound of formula (III) and combinations thereof, and methods of using the same in enhancing mitochondrial function, or treating mitochondrial dysfunction.

10 Claims, 22 Drawing Sheets

(56) References Cited

OTHER PUBLICATIONS

Duclos, R. I., et al., "Synthesis and characterization of Se-adenosyl-L-selenohomocysteine selenoxide", J Sulphur Chem., Apr. 2015, 36(2), pp. 135-144.
Kogami, M., et al., "An efficient method for the synthesis of selenium modified nucleosides: its application in the synthesis of Se-adenosyl-L-selenomethionine (SeAM)", Organic & Biomolecular Chemistry, Aug. 2015, 13(36), pp. 9405-9417.
Bothwell, I. R., et al., "Large-Scale, Protection-Free Synthesis of Se-Adenosyl-L-selenomethionine Analogues and Their Application as Cofactor Surrogates of Methyltransferases", Org. Lett., May 2014, 16(11), pp. 3056-3059.
Singh, S., et al., "Facile Chemoenzymatic Strategies for the Synthesis and Utilization of S-Adenosyl-(L)-Methionine Analogues", Angew. Chem. Int. Ed., Mar. 2014, 53 (15), pp. 3965-3969.
SciFinder, "Kogami_2015_Org_Bio_Chem_Structures", ACS, 2015, structure 31, 1805788-83-3, 8 pages.
International Search Report for International Patent Application PCT/US2014/US2014/029542 dated Jul. 31, 2014, 3 pages.
U.S. Appl. No. 14/855,128, filed Sep. 15, 2015, Ronan Power et al.
U.S. Appl. No. 14/855,065, filed Sep. 15, 2015, Ronan Power et al.
International Search Report and the Written Opinion for corresponding International Patent Application PCT/US2015/050476 dated Dec. 17, 2015.
International Search Report and the Written Opinion for International Patent Application PCT/US15/50490 dated Jan. 27, 2016.

\* cited by examiner

HEK293T kidney cells

C2C12 skeletal muscle cells

IMR-32 neuronal cells

IMR-32 neuronal cells

IMR-32 neuronal cells

MT function in stressed rat brain

AML-12 liver cells

AML-12 liver cells

AML-12 liver cells

IMR-32 neuronal cells

IMR-32 neuronal cells

IMR-32 neuronal cells

IMR-32 neuronal cells

IMR-32 neuronal cells

AML-12 liver cells

AML-12 liver cells

COMPOSITIONS OF SELENOORGANIC COMPOUNDS AND METHODS OF USE THEREOF

The present application is a National Stage Application of PCT/US 2014/029542 filed on Mar. 14, 2014, the disclosure of which is incorporated herein by reference in its entirety.

FIELD OF THE PRESENT APPLICATION

The present application relates to compositions of selenoorganic compositions and compounds and methods for their use in various biological pathways to enhance mitochondrial function, treat disease, and inhibit or enhance specific processes in particular types of animal and human cells.

BACKGROUND

Selenium (Se) is an essential trace element that plays a critical role in many biological processes, such as reproduction, thyroid hormone metabolism, DNA synthesis, and protection from oxidative damage and infection. Selenium is incorporated at the catalytic site of various selenium dependent enzymes such as glutathione peroxidase (GPx), thioredoxin reductases, and one methionine-sulfoxidereductase. These selenoenzymes contribute to regulation of metabolic activity, immune function, antioxidant defense, intracellular redox regulation, and mitochondrial function.

The organelle known as the mitochondrion ("MT") is the main energy source in cells of higher organisms. Mitochondria provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis. Mitochondrial respiration occurs on the inner mitochondrial membrane and is achieved by the flow of electrons through the electron transport system, which contains four complexes (complex I, II, III, and IV) with a further complex (complex V) serving as a site for ATP synthesis (ATP synthase). Impairment or reduction of activity of any complex disrupts electron flow and may cause mitochondrial respiratory dysfunction (See, e.g., Schildgen et al., *Exp Hematol* 2011; 39:666-67510,11; Arthur et al., *Mol Neurodegener* 2009; 4:37).

Mitochondrial dysfunction leading to cell death, reactive oxygen species production, increased oxidative DNA damage, increased autophagy, and loss of mitochondrial membrane potential has been associated with conditions such as diabetes, obesity, aging related neurodegeneration including Alzheimer's disease, stroke, insulin resistance, and atherosclerosis. An inorganic form of selenium, sodium selenite, has been shown to affect mitochondrial function in certain circumstances. Mehta et al. showed a marker of mitochondrial biogenesis, PGC1a, is increased in ischemic brain tissue and that sodium selenite further increases PGC1a after ischemia and recirculation. (Mehta et al., BMC Neuroscience 2012 13:79). Tirosh et al. showed that a high dose but not an intermediate dose of sodium selenite prevented hapten induced impairment of mitochondrial function due to hapten induced inflammation in colon tissue. (Tirosh et al., Nutrition 2007 23:878). These results suggest that inorganic selenium can impact mitochondrial function in cells undergoing damage. However, some studies have found that sodium selenite is less bioavailable than other forms of selenium calling into question its effectiveness. (Rider et al., J Anim Physiol Anim Nutr (Berl) 2010 94(1):99-110).

In addition, results in the literature indicate that different chemical forms of selenium have different bioactivities. For example, a selenozolidine was more effective at reducing the number of lung tumors than selenomethionine (Poerschke et al, J Biochem Molecular Toxicology 2012 26:344). Barger et al. showed that mice fed different sources of selenium, for example, selenium methionine, sodium selenite and selenized yeast, had differential effects on gene expression and on specific functional pathways of mitochondrial structure and function. (Barger et al, Genes and Nutrition 2012 7:155).

Because of the apparent difference in bioactivity and availability of distinct chemical forms of selenium, there is a need to identify chemical forms of selenium and to characterize their effects on biological processes. Characterization of these effects on biological processes can lead to medicinal regulation of significant biological processes to prevent or combat diseases, such as those diseases linked to mitochondrial dysfunction. Diseases linked to mitochondrial dysfunction may be prevented or treated by administering particular chemical forms of selenium that reduce mitochondrial dysfunction or upregulate mitochondrial function in one or more types of animal or human cells. One explanation for the variation in bioactivity could be that different forms of selenium have different effects on biological pathways at the molecular level.

SUMMARY OF THE INVENTION

The present application is directed to seleno-organic compounds, compositions, and methods of using the compounds and compositions. The compounds include 5'-Methylselenoadenosine ("compound C"), Se-Adenosyl-L-homocysteine ("compound D"), Gamma-glutamyl-methylselenocysteine ("compound E"), a compound of formula I, compound of formula II, a compound of formula III, and combinations thereof. As described herein, compositions and combinations thereof are useful to enhance mitochondrial function, to treat mitochondrial dysfunction, to treat Alzheimer's disease, and to modulate glucose metabolism in a tissue-specific and tissue-appropriate manner.

In one aspect of the present application, different chemical forms of organic selenium are identified as biologically active. Selenium containing compounds as described herein can be obtained from selenized yeast or can be chemically synthesized as described herein. Selenized yeast contains many selenium and sulfur compounds but not all of the selenium compounds in selenized yeast impact biological processes. In addition, a mixture of selenium and sulfur compounds in selenized yeast have been shown to be inhibitory to each other or to negatively impact biological processes.

Another aspect of the present application provides analogs or derivatives of the biologically active selenium compounds described herein. Analogs and/or derivatives of the selenium-containing compounds can be prepared synthetically. In some embodiments, the analogs have increased stability, decreased oxidation, increased half-life, and/or target the compounds to a specific tissue.

In another aspect of the present application, different chemical forms of selenium have been shown to have different tissue specificity (e.g. some compounds are active on neuronal cells but not liver cells). In addition, the same selenium containing composition may activate a transcriptional activator in one cell type while it inactivates the same transcriptional activator in a different cell type. These differential activities and tissue specificities of different selenium-containing compounds and combinations thereof are surprising and unexpected.

One aspect of the present application provides compositions comprising a compound selected from the group consisting of 5'-Methylselenoadenosine, Se-Adenosyl-L-homocysteine, Gamma-glutamyl-methylseleno-cysteine, a compound of formula (I), a compound of formula II, a compound of formula (III), and combinations thereof. In further embodiments, one or more of these compounds can be isolated and/or purified.

In other embodiments, compositions may exclude one or more of 5'-Methylthioadenosine, S-Adenosyl-L-homocysteine, Gamma-glutamyl-methyl-cysteine, or glutamyl selenocysteine, because one or more of these compounds may be unnecessary to the composition or inhibitory to other compounds in the composition.

Another aspect of the present application provides methods of using the compositions described herein to enhance mitochondrial function, treat mitochondrial dysfunction, treat Alzheimer's disease, and/or modulate glucose metabolism.

In embodiments, a method for treating Alzheimer's disease comprises: administering an effective amount of a composition to a subject, the composition comprising 5'-Methylselenoadenosine, a compound of formula (I), or mixtures thereof. In other embodiments, one or more of these compounds can be isolated and/or purified.

In still other embodiments, a method for treating Alzheimer's disease comprises: administering an effective amount of a composition to a subject, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III). In embodiments of this invention, one or more of these compounds can be isolated and/or purified.

In other embodiments, a method for inhibiting B amyloid accumulation in one or more neuronal cells comprises: administering an effective amount of a composition to the one or more neuronal cells, the composition comprising a compound selected from the group consisting of 5'-Methylselenoadenosine, a compound of formula (I), and mixtures thereof, wherein the effective amount inhibits B amyloid accumulation in one or more neuronal cells as compared to neuronal cells not treated with the composition. In further embodiments, one or more of these compounds can be isolated and/or purified.

In another embodiment, a method for inhibiting B amyloid accumulation in one or more neuronal cells comprises: administering an effective amount of a composition to one or more neuronal cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount inhibits B amyloid accumulation in neuronal cells as compared to neuronal cells not treated with the composition. In further embodiments, one or more of these compounds can be isolated and/or purified.

In embodiments, a method for inhibiting tau phosphorylation in one or more neuronal cells comprises: administering an effective amount of a composition to the one or more neuronal cells, the composition comprising a compound selected from the group consisting of 5'-Methylselenoadenosine, a compound of formula (I), and mixtures thereof, wherein the effective amount inhibits tau phosphorylation in one or more neuronal cells as compared to neuronal cells not treated with the composition. In further embodiments, one or more of these compounds can be isolated and/or purified.

In other embodiments, a method for inhibiting tau phosphorylation in one or more neuronal cells comprises: administering an effective amount of a composition to the one or more neuronal cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount inhibits tau phosphorylation in neuronal cells as compared to neuronal cells not treated with the composition. In further embodiments, one or more compounds can be isolated and/or purified.

In embodiments, a composition comprises 5'-Methylselenoadenosine, or a compound of formula (I) or a selenoglycoside thereof. In yet other embodiments, the composition may exclude glutamyl selenocysteine, methionine, or selenomethionine because of their potential inhibitory effects in the composition on active compounds in the composition.

In some embodiments, the effective amount administered to a subject is 200 micrograms or less per day. In embodiments, the composition of the present invention is administered once daily to a subject.

In another aspect, a method for enhancing mitochondrial function in one or more cells selected from the group consisting of skeletal muscle cell, neuronal cell, and combinations thereof, comprises: administering an effective amount of a composition to the one or more cells, the composition comprising a compound selected from the group consisting of 5'-Methylselenoadenosine, Se-Adenosyl-L-homocysteine, Gamma-glutamyl-methylseleno-cysteine, a compound of formula (I), a compound of formula (III), and combinations thereof, wherein the effective amount enhances mitochondrial function as compared to cells not treated with the composition. In further embodiments, one or more compounds can be isolated and/or purified.

In other embodiments, a method for enhancing mitochondrial function in one or more liver cells comprises: administering an effective amount of a composition to the one or more liver cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount enhances mitochondrial function as compared to cells not treated with the composition. In further embodiments, one or more compounds can be isolated and/or purified.

In another aspect, a method of modulating glucose metabolism in one or more cells selected from the group consisting of liver cells, skeletal muscle cells, and mixtures thereof, said method comprises: administering an effective amount of a composition to the one or more cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount modulates glucose metabolism as compared to cells not treated with the composition. In further embodiments, one or more compounds can be isolated and/or purified.

In embodiments, a method of decreasing expression of glucose 6 phosphatase complex in one or more liver cells, comprises: administering an effective amount of a composition to the one or more cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount inhibits expression glucose 6 phosphatase as compared to cells not treated with the composition. In further embodiments, one or more compounds can be isolated and/or purified.

BRIEF DESCRIPTION OF THE DRAWINGS

The accompanying drawings, which are incorporated in and constitute a part of the description, illustrate several aspects of the invention and together with the description, serve to explain the principles of the invention. A brief description of the drawings is as follows.

DETAILED DESCRIPTION

Definitions

Figure 1:
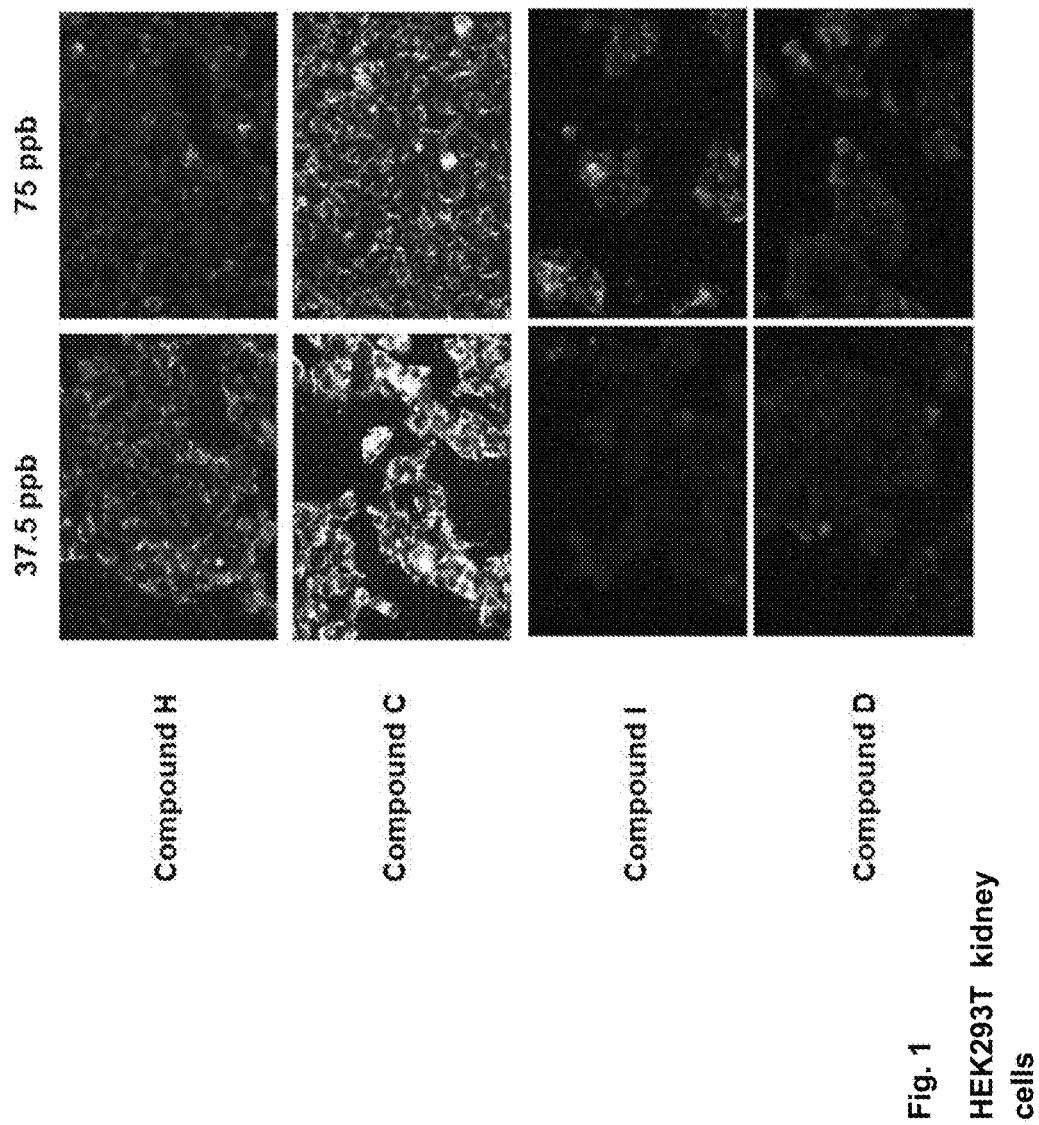
FIG. 1 shows enhanced mitochondrial ("MT") potential (fluorescence) upon treatment of HEK293T kidney cells with 5'-Methylselenoadenosine ("compound C") but not Se-Adenosyl-L-homocysteine ("compound D"). Images were captured at the same exposure time and magnification under the fluorescence microscope.

As used herein, the terms "administration" and "administering" refer to the act of giving a drug, prodrug, or other agent, or therapeutic treatment (e.g., compositions of the present application) to a subject (e.g., a subject or in vivo, in vitro, or ex vivo cells, tissues, and organs). Exemplary routes of administration to the human body can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

The term "alkyl" refers to a branched or unbranched saturated hydrocarbon group of 1 to 24 carbon atoms. Preferred "alkyl" groups herein contain 1 to 16 carbon atoms; i.e. $C_{1-16}$ alkyl. Examples of an alkyl group include, but are not limited to, methyl, ethyl, propyl, iso-propyl, butyl, iso-butyl, secondary-butyl, tertiary-butyl, pentyl, iso-pentyl, neo-pentyl, hexyl, iso-hexyl, 3-methylpentyl, 2,3-dimethylbutyl, neo-hexyl, heptyl, octyl, nonyl, decyl, undecyl, dodecyl, tridecyl, tetradecyl, pentadecyl, and hexadecyl. Most preferred are "lower alkyl" which refer to an alkyl group of one to six, more preferably one to four, carbon atoms. The alkyl group may be optionally substituted with an acyl, amino, amido, azido, carboxyl, alkyl, aryl, halo, guanidinyl, oxo, sulfanyl, sulfenyl, sulfonyl, heterocyclyl or hydroxyl group.

The term "alkali metal" refers to refers to metallic salts include, but are not limited to, appropriate alkali metal (group 1a) salts, alkaline earth metal (group IIa) salts, and other physiological acceptable metals. Such salts can be made from aluminum, calcium, lithium, magnesium, potassium, sodium and zinc.

The term "alkenyl" refers to a straight or branched carbon chain containing at least one carbon-carbon double bond. In exemplary embodiments, "alkenyl" refers to a hydrocarbon containing 2, 3, 4, 5, 6, 7, 8, 9 or 10 carbon atoms, i.e. $C_{1-10}$ alkenyl. Examples of an alkenyl group include, but are not limited to, ethene, propene, butene, pentene, hexene, heptene, octene, nonene and decene. The alkenyl group may be optionally substituted with an amino, alkyl, halo, or hydroxyl group.

The term "amido" refers to either a C-amido group such as —CONR'R" or an N amido group such as —NR'COR" wherein R' and R" as used in this definition are independently hydrogen, alkyl, alkenyl, alkynyl, alkoxy, carbocyclic, heterocyclic, aryl, or aralkyl. A "sulfoamido" group includes the —NR'—SO$_2$—R". Most preferably, R' and R" are hydrogen, alkyl, aryl, or aralkyl.

The term "alkynyl" refers to a straight or branched carbon chain containing at least one carbon-carbon triple bond. In exemplary embodiments, "alkynyl" refers to a hydrocarbon containing 2, 3, 4, 5, 6, 7, 8, 9 or 10 carbon atoms, i.e., $C_{2-10}$ alkynyl. Examples of an alkynyl group include, but are not limited to, ethyne, propyne, butyne, pentyne, hexyne, heptyne, octyne, nonyne and decyne. The alkynyl group may be optionally substituted with an amino, alkyl, halo, or hydroxyl group.

The term "aryl" refers to a carbocyclic aromatic system containing one, two or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, tetralin, indane, indene, and biphenyl. The aryl group may optionally be substituted with an amino, alkyl, halo, hydroxyl, carbocyclic, heterocyclic, or another aryl group.

The term "cycloalkyl" refers to a monocyclic saturated or partially saturated carbon ring, wherein the number of ring atoms is indicated by a range of numbers. In exemplary embodiments, "cycloalkyl" refers to a carbon ring as defined above containing 3-12 ring atoms (i.e. $C_{3-12}$ cycloalkyl). As used herein, cycloalkyl encompasses monocyclo, bridged, spiro, fused, bicyclo and tricyclo ring structures. Examples of a cycloalkyl group include, but are not limited to, cyclopropyl, cyclobutyl, cyclopentyl, cyclopentenyl, cyclohexyl, cyclohexenyl, cycloheptyl, cycloheptenyl, norbornyl, decalin, adamantyl, and cyclooctyl. The cycloalkyl group may be optionally substituted with an amino, alkyl, halo, or hydroxyl group.

The term "aralkyl" refers to aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl. The terms benzyl and phenylmethyl are interchangeable.

The term "aryloxy" refers to aryl groups, as defined above, attached to an oxygen atom. The aryloxy groups may optionally be substituted with a halo, hydroxyl, or alkyl group. Examples of such groups include phenoxy, 4-chloro-3-ethylphenoxy, 4-chloro-3-methylphenoxy, 3-chloro-4-ethylphenoxy, 3,4-dichlorophenoxy, 4-methylphenoxy, 3-trifluoromethoxyphenoxy, 3-trifluoromethylphenoxy, 4-fluorophenoxy, 3,4-dimethylphenoxy, 5-bromo-2-fluorophenoxy, 4-bromo-3-fluorophenoxy, 4-fluoro-3-methylphenoxy, 5,6,7,8-tetrahydronaphthyloxy, 3-isopropylphenoxy, 3-cyclopropylphenoxy, 3-ethylphenoxy, 4-tert-butylphenoxy, 3-pentafluoroethylphenoxy, and 3-(1,1,2,2-tetrafluoroethoxy)phenoxy.

The term "alkoxy" refers to oxy-containing groups substituted with an alkyl, or cycloalkyl group. Examples include, without limitation, methoxy, ethoxy, tert-butoxy, and cyclohexyloxy. Most preferred are "lower alkoxy" groups having one to six carbon atoms. Examples of such groups include methoxy, ethoxy, propoxy, butoxy, iso-propoxy, and tert-butoxy groups.

The term "aralkoxy" refers to oxy-containing aralkyl groups attached through an oxygen atom to other groups. "Lower aralkoxy" groups are those phenyl groups attached to lower alkoxy group as described above. Examples of such groups include benzyloxy, 1-phenylethoxy, 3-trifluoromethoxybenzyloxy, 3-trifluoromethylbenzyloxy, 3,5-difluorobenzyloxy, 3-bromobenzyloxy, 4-propylbenzyloxy, 2-fluoro-3-trifluoromethylbenzyloxy, and 2-phenylethoxy. The term "acyl" refers to —C(=O)R wherein R used in this definition is hydrogen, alkyl, alkenyl, alkynyl, carbocyclic, heterocyclic, aryl, or aralkyl. Most preferably, R is hydrogen, alkyl, aryl, or aralkyl.

The term "carboxyl" refers to —R'C(=O)OR", wherein R' and R" as used in this definition are independently hydrogen, alkyl, alkenyl, alkynyl, carbocyclic, heterocyclic, heterocyloalkyl, aryl, ether, or aralkyl, or R' can additionally be a covalent bond. "Carboxyl" includes both carboxylic acids, and carboxylic acid esters. The term "carboxylic acid" refers to a carboxyl group in which R" is hydrogen, or a salt. Such acids include formic, acetic, propionic, butryic, valeric acid, 2-methyl propionic acid, oxirane-carboxylic acid, and cyclopropane carboxylic acid. The term "carboxylic acid ester" or "ester" refers to a carboxyl group in which R" is alkyl, alkenyl, alkynyl, carbocyclic, heterocyclic, aryl, or aralkyl. Examples of carboxylic acids include, but are not limited to formic acid, acetic acid, propionic acid, butanoic acid, pentanoic acid, hexanoic acid, heptanoic acid, octanoic acid, nonanoic acid, decanoic acid, cyclopropanecarboxylic acid, cyclobutanecarboxylic acid, cyclopentanecarboxylic acid, cyclohexanecarboxylic acid, cycloheptanecarboxylic acid, cyclooctanecarboxylic acid, or cyclononanecarboxylic acid.

The term "carbonyl" refers to refers to a C=O moiety, also known as an "oxo" group.

The term "heterocycle" or "heterocyclyl" or "heterocyclic ring" refers to an optionally substituted, saturated or unsaturated, aromatic or non-aromatic cyclic hydrocarbon with 3 to 12, or 5 to 6, carbon atoms, wherein at least one of the ring atoms is an O, N, S, P or Se. For example, in some embodiments, a ring N atom from the heterocyclyl is the bonding atom to —C(O) to form an amide, carbamate, or urea. In exemplary embodiments, "heterocyclyl" refers to a cyclic hydrocarbon as described above containing 4, 5, or 6 ring atoms (i.e., $C_{4-6}$ heterocyclyl). Examples of a heterocyclic group include, but are not limited to, aziridine, oxirane, thiirane, azetidine, oxetane, thietane, pyrrolidine, imidazole, tetrahydrofuran, pyran, thiopyran, thiomorpholine, thiomorpholine S-oxide, oxazoline, tetrahydrothiophene, piperidine, tetrahydropyran, thiane, imidazolidine, oxodioxolenyl, oxazolidine, thiazolidine, dioxolane, dithiolane, piperazine, oxazine, dithiane, dioxane, pyridinyl, furanyl, benzofuranyl, isobenzofuranyl, pyrrolyl, thienyl, 1,2,3-triazolyl, 1,2,4-triazolyl, indolyl, imidazolyl, thiazolyl, thiadiazolyl, pyrimidinyl, oxazolyl, triazinyl, and tetrazolyl. Exemplary heterocycles include benzimidazole, dihydrothiophene, dioxin, dioxane, dioxolane, dithiane, dithiazine, dithiazole, dithiolane, furan, indole, 3-H indazole, 3-H-indole, indolizine, isoindole, isothiazole, isoxazole, morpholine, oxazole, oxadiazole, oxathiazole, oxathiazolidine, oxazine, oxadiazine, piperazine, piperidine, purine, pyran, pyrazine, pyrazole, pyridine, pyrimidine, pyrimidine, pyridazine, pyrrole, pyrrolidine, tetrahydrofuran, tetrazine, thiadiazine, thiadiazole, thiatriazole, thiazine, thiazole, thiophene, triazine, and triazole. The heterocycle may be optionally substituted with an amino, alkyl, alkenyl, alkynyl, halo, hydroxyl, carbocyclic, thio, other heterocyclic, or aryl group.

The term "heteroaryl" refers to a cyclic hydrocarbon, where at least one of the ring atoms is an O, N, S, P or Se, the ring is characterized by delocalized [pi] electrons (aromaticity) shared among the ring members, and wherein the number of ring atoms is indicated by a range of numbers. Heteroaryl moieties as defined herein have C, N, S, P or Se bonding hands. For example, in some embodiments, a ring N atom from the heteroaryl is the bonding atom to —C(O) to form an amide, carbamate, or urea. In exemplary embodiments, "heteroaryl" refers to a cyclic hydrocarbon as described above containing 5 or 6 ring atoms (i.e. $C_{5-6}$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine. The term "hydroxy" or "hydroxyl" refers to the substituent —OH.

The term "oxo" refers to the substituent =O.
The term "nitro" refers to $NO_2$.
The term "azido" refers to $N_3$.
The term "sulfur analog(s)" refers to an analogue of a compound of interest in which one or more selenium atoms have been replaced by one or more sulfur atoms, respectively.

The term "sulfanyl" refers to —SR' where R' as used in this definition is hydrogen, alkyl, alkenyl, alkynyl, carbocyclic, heterocyclic, aryl, or aralkyl. The term "sulfenyl" refers to —SOR' where R' as used is this definition is hydrogen, alkyl, alkenyl, alkynyl, carbocyclic, heterocylic, aryl, or aralkyl.

The term "sulfonyl" refers to —SOR' where R' refers to hydrogen, alkyl, alkenyl, alkynyl, carbocyclic, heterocylic, aryl, or aralkyl.

The term "ketone" refers to a moiety containing at least one carbonyl group where the carbonyl carbon is bound to two other carbon atoms. In exemplary embodiments, "ketone" refers to a carbonyl-containing moiety as described above containing 3, 4, 5, 6, 7, 8, 9 or 10 carbon atoms (i.e. $C_{3-10}$ ketone). Examples of a ketone group include, but are not limited to, acetone, butanone, pentanone, hexanone, heptanone, octanone, nonanone, decanone, cyclobutanone, cyclopentanone, cyclohexanone, cycloheptanone, cyclooctanone, cyclononanone and cyclodecanone.

The term "amino" refers to a primary, secondary or tertiary amino group of the formula —NR'R" wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", includes unsubstituted, monosubstituted (e.g., monoalkylamino or monoarylamino), and disubstituted (e.g., dialkylamino or aralkylamino) amino groups. Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "amine" refers to a primary, secondary or tertiary amino group of the formula —NR'R" wherein R' and R" as used in this definition are independently hydrogen, acyl, alkyl, alkyenyl, alkynyl, aralkyl, aryl, carboxyl, cycloalkyl, heterocyclic, or other amino (in the case of hydrazide) or R' and R" together with the nitrogen atom to which they are attached, form a ring having 4-8 atoms. Thus, the term "amino", as used herein, includes unsubstituted, monosubstituted (e.g., monoalkylamino or monoarylamino), and disubstituted (e.g., dialkylamino or aralkylamino) amino groups Amino groups include —$NH_2$, methylamino, ethylamino, dimethylamino, diethylamino, methyl-ethylamino, pyrrolidin-1-yl or piperidino, morpholino, etc. Other exemplary "amino" groups forming a ring include pyrrolyl, imidazolyl, pyrazolyl, isothiazolyl, isoxazolyl, pyridyl, pyrazinyl, pyrimidinyl, pyridazinyl, indolizinyl, imidazolyl, isoindolyl, indolyl, indazolyl, purinyl, quinolizinyl. The ring containing the amino group may be optionally substituted with another amino, alkyl, alkenyl, alkynyl, halo, or hydroxyl group.

The term "alcohol" refers to "hydroxy" or "hydroxyl" refers to the substituent —OH.

The term "amino alcohol" refers to a functional group containing both an alcohol and an amine group. As used herein, "amino alcohols" also refers to amino acids as defined above having a carbon bound to an alcohol in place of the carboxylic acid group. In exemplary embodiments, the term "amino alcohol" refers to an amino alcohol as defined above wherein the amine is bound to the carbon adjacent to the alcohol-bearing carbon. In exemplary embodiments, "amino alcohol" refers to an amine and alcohol-containing moiety as described above containing 1, 2, 3, 4, 5, 6, 7, 8, 9, 10, 11 or 12 carbon atoms (i.e., $C_{1-12}$ amino alcohol). Examples of amino alcohols include, but are not limited to, ethanolamine, heptaminol, isoetarine, norepinephrine, propanolamine, sphingosine, methanolamine, 2-amino-4-mercaptobutan-1-ol, 2-amino-4-(methylthio)butan-1-ol, cysteinol, phenylglycinol, prolinol, 2-amino-3-phenyl-1-propanol, 2-amino-1-propanol, cyclohexylglycinol, 4-hydroxy-prolinol, leucinol, tert-leucinol, phenylalaninol, a-phenylglycinol, 2-pyrrolidinemethanol, tyrosinol, valinol, serinol, 2-dimethylaminoethanol, histidinol, isoleucinol, leucinol, methioninol, 1-methyl-2-pyrrolidinemethanol, threoninol, tryptophanol, alaninol, argininol, glycinol, glutaminol, 4-amino-5-hydroxypentanamide, 4-amino-5-hydroxypentanoic acid, 3-amino-4-hydroxybutanoic acid, lysinol, 3-amino-4-hydroxybutanamide, and 4-hydroxy-prolinol.

The term "amino acid" refers to a group containing a carboxylic acid and an amine bound to the carbon atom immediately adjacent to the carboxylate group, and includes both natural and synthetic amino acids. Examples of amino acids include, but are not limited to, arginine, histidine, lysine, aspartic acid, glutamic acid, serine, threonine, asparagine, glutamine, cysteine, selenocysteine, glycine, proline, alanine, valine, isoleucine, leucine, methionine, phenylalanine, tyrosine, tryptophan. The carboxyl is substituted with H, a salt, ester, alkyl, or aralkyl. The amino group is substituted with H, acyl, alkyl, alkenyl, alkynyl, carboxyl, cycloalkyl, aralkyl, or heterocyclyl.

The term "ether" refers to the group —R'—O—R" wherein R' and R" as used in this definition are independently hydrogen, alkyl, alkenyl, alkynyl, carbocyclic, heterocylic, aryl, or aralkyl, and R' can additionally be a covalent bond attached to a carbon.

The term "halogen" refers to a fluorine, chlorine, bromine or iodine atom.

The term "halide" refers to a functional group containing an atom bond to a fluorine, chlorine, bromine or iodine atom. Exemplary embodiments disclosed herein may include "alkyl halide," "alkenyl halide," "alkynyl halide," "cycloalkyl halide," "heterocyclyl halide," or "heteroaryl halide" groups. In exemplary embodiments, "alkyl halide" refers to a moiety containing a carbon-halogen bond containing 1, 2, 3, 4, 5, 6, 7, 8, 9 or 10 carbon atoms (i.e., $C_{1-10}$ alkyl halide). Examples of an alkyl halide group include, but are not limited to, fluoromethyl, fluoroethyl, chloromethyl, chloroethyl, bromomethyl, bromoethyl, iodomethyl and iodoethyl groups. Unless otherwise indicated, any carbon-containing group referred to herein can contain one or more carbon-halogen bonds. By way of non-limiting example, a Cialkyl group can be, but is not limited to, methyl, fluoromethyl, difluoromethyl, trifluoromethyl, chloromethyl, dichloromethyl, trichloromethyl, bromomethyl, dibromomethyl, tribromomethyl, iodomethyl, diiodomethyl, triiodomethyl, chlorofluoromethyl, dichlorofluoromethyl, and difluorochloromethyl.

In the compounds described herein, heteroatoms are capable of bearing multiple different valencies. By way of non-limiting example, S, Se and N can be neutral or hold a positive charge, and O can be neutral or hold a positive or negative charge.

In some embodiments, compounds according to formula (I), (II), or (III) encompass diastereomers and enantiomers of the illustrated compounds. Enantiomers are defined as one of a pair of molecular entities which are mirror images of each other and non-superimposable. Diastereomers or diastereoisomers are defined as stereoisomers other than enantiomers. Diastereomers or diastereoisomers are stereoisomers not related as mirror images. Diastereoisomers are characterized by differences in physical properties.

The terms "compound C" or "Compound C", shown herein, refers to 5'-Methylselenoadenosine; also known as (2R,4S,5S)-2-(6-amino-9H-purin-9-yl)-5-((methylselanyl)methyl)tetrahydrofuran-3,4-diol, CAS Registry Number 5135-40-0, and includes any pharmaceutically acceptable salts thereof

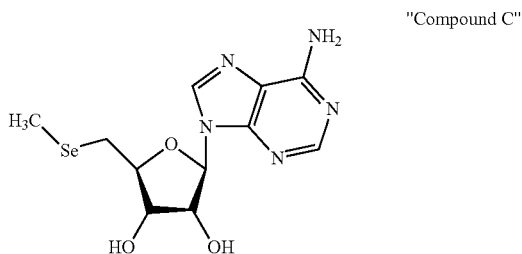

"Compound C"

The terms "compound D" or "Compound D", shown herein, refers to 5'-Selenoadenosyl homocysteine; (2R)-2-amino-4-((((2S,3S,5R)-5-(6-amino-9H-purin-9-yl)-3,4-dihydroxytetrahydrofuran-2-yl)methyl)selanyl)butanoic acid, CAS Registry Number 4053-91-2, and includes any pharmaceutically acceptable salts thereof

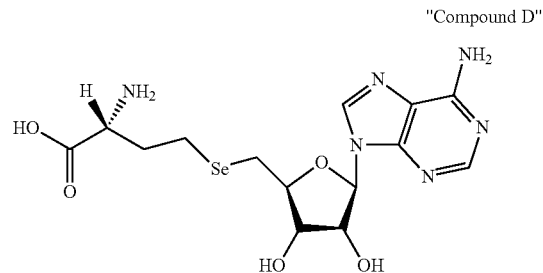

"Compound D"

The terms "compound E" or "Compound E", shown herein, refers to gamma-glutamyl-methylseleno-cysteine or γ-L-glutamyl-Se-methyl-L-cysteine; also known as N5-(1-carboxy-2-(methylselanyl)ethyl)-L-glutamine, or any pharmaceutically acceptable salt thereof.

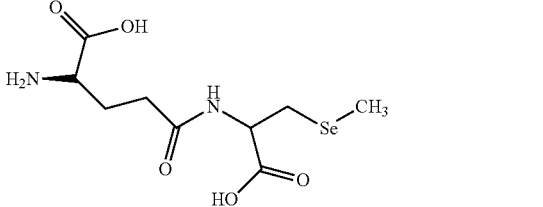

"Compound E"

The terms "compound H" or "Compound H", shown herein, refers to 5'-Methylthioadenosine; 5'-S-Methyl-5'-thioadenosine, CAS Registry No. 2457-80-9, or a pharmaceutically acceptable salt thereof.

"Compound H"

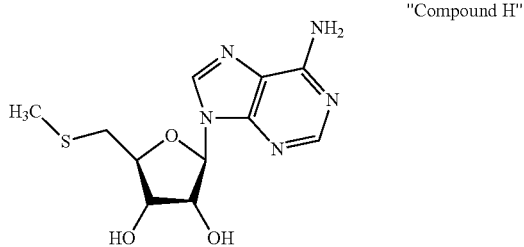

The terms "compound I" or "Compound I" refers to S-Adenosyl-L-homocysteine, also known as (S)-5'-(S)-(3-Amino-3-carboxypropyl)-5'-thioadenosine, CAS Registry No. 979-92-0, or a pharmaceutically acceptable salt thereof "Compound I"

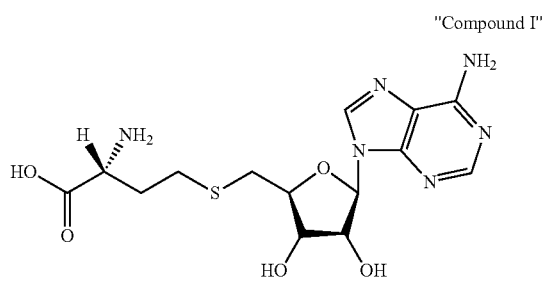

The terms "compound J" or "Compound J", shown herein, refers to γ-L-glutamyl-methyl-L-cysteine, also known as Gamma-glutamyl-methyl-cysteine, or a pharmaceutically acceptable salt thereof "Compound J"

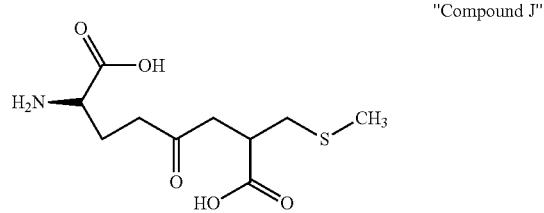

The term "compounds CDE" refers to a mixture of compound C, compound D and compound E, or pharmaceutically acceptable salts thereof The term "compounds HIJ" refers to a mixture of compound H, compound I and compound J, or pharmaceutically acceptable salts thereof The terms "analog" and "derivative" are interchangeable and refer to a natural or non-natural modification of at least one position of a given molecule. For example, a derivative of a given compound or molecule is modified either by addition of a functional group or atom, removal of a functional group or atom or change of a functional group or atom to a different functional group or atom (including, but not limited to, isotopes).

The term "comprising" refers to a composition, compound, formulation or method that is inclusive and does not exclude additional elements or method steps.

The term "consisting of" refers to a compound, composition, formulation, or method that excludes the presence of any additional component or method steps.

The term "consisting essentially of" refers to a composition, compound, formulation or method that is inclusive of additional elements or method steps that do not materially affect the characteristic(s) of the composition, compound, formulation or method.

The term "compound(s)" refers to any one or more chemical entity, pharmaceutical, drug, and the like that can be used to treat or prevent a disease, illness, sickness, or disorder of bodily function. Compounds comprise both known and potential therapeutic compounds. A compound can be determined to be therapeutic by screening using the screening methods of the present application. A "known therapeutic compound" refers to a therapeutic compound that has been shown (e.g., through animal trials or prior experience with administration to humans) to be effective in such treatment. In other words, a known therapeutic compound is not limited to a compound efficacious in the treatment of disease (e.g., neurodegenerative disease).

The term "composition(s)" refers to the combination of one or more compounds with or without another agent, such as but not limited to a carrier agent. (e.g., one or more selenium containing compounds with a carrier, inert or active, making the composition especially suitable for diagnostic or therapeutic use in vitro, in vivo or ex vivo.

The term "component" refers to a constituent part of a compound, or a composition. For example, components of a composition can include a compound, a carrier, and any other agent present in the composition.

The term "effective amount" refers to the amount of a composition or compound sufficient to effect beneficial or desired results. An effective amount can be administered in one or more applications or dosages and is not intended to be limited to a particular formulation or administration route.

The term "hydrate" refers to a compound disclosed herein which is associated with water in the molecular form, i.e., in which the H—OH bond is not split, and may be represented, for example, by the formula R×H$_2$O, where R is a compound disclosed herein. A given compound may form more than one hydrate including, for example, monohydrates (R×H$_2$O), dihydrates (R$_2$×H$_2$O), trihydrates (R$_3$×H$_2$O), and the like.

The term "inhibitory" or "antagonistic" refers to the property of a compound that decreases, limits, or blocks the action or function of another compound.

The term "isolated" refers to the separation of a material from at least one other material in a mixture or from materials that are naturally associated with the material. For example, a compound synthesized synthetically is separated from a starting material or an intermediate.

The term "mitochondrial potential" refers to voltage difference across the inner mitochondrial membrane maintained by the net movement of positive charges across the membrane.

The term "modulates" refers to a change in the state (e.g. activity or amount) of a compound from a known or determined state.

"Optional" or "optionally" refers to a circumstance in which the subsequently described event or circumstance may or may not occur, and that the description includes instances where said event or circumstance occurs and instances in which it does not. "Optionally" is inclusive of embodiments in which the described conditions is present and embodiments in which the described condition is not present. For example, "optionally substituted phenyl" means that the phenyl may or may not be substituted, and that the description includes both unsubstituted phenyl and phenyl wherein there is substitution. "Optionally" is inclusive of embodiments in which the described conditions is present and embodiments in which the described condition is not present.

The term "organic selenium" or "seleno-organic compound" refers to any organic compound wherein selenium replaces sulfur. Thus, organic selenium can refer to any such compound biosynthesized by yeast, or it can refer to free organic seleno-compounds that are chemically synthesized. An example of the latter is free selenomethionine. In some cases, seleno-organic compounds also include selenometabolites.

The terms "patient" or "subject" are used interchangeably and refer to any member of Kingdom Animalia. Preferably a subject is a mammal, such as a human, domesticated mammal or a livestock mammal.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ration.

The phrase "pharmaceutically-acceptable carrier" refers to a pharmaceutically-acceptable material, composition or vehicle, such as a liquid or solid filler, diluent, excipient, solvent or encapsulating material, involved in carrying or transporting the subject selenium containing compound or analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "prodrug" refers to a pharmacologically active or more typically an inactive compound that is converted into a pharmacologically active agent by a metabolic transformation. Prodrugs of a compound of any of the formulae above are prepared by modifying functional groups present in the compound of any of the formulae above in such a way that the modifications may be cleaved in vivo to release the parent compound. In vivo, a prodrug readily undergoes chemical changes under physiological conditions (e.g., are hydrolyzed or acted on by naturally occurring enzyme(s)) resulting in liberation of the pharmacologically active agent. Prodrugs include compounds of any of the formulae above wherein a hydroxy, amino, or carboxy group is bonded to any group that may be cleaved in vivo to regenerate the free hydroxyl, amino or carboxy group, respectively. Examples of prodrugs include, but are not limited to esters (e.g., acetate, formate, and benzoate derivatives) of compounds of any of the formulae above or any other derivative which upon being brought to the physiological pH or through enzyme action is converted to the active parent drug. Conventional procedures for the selection and preparation of suitable prodrug derivatives are described in the art (see, for example, Bundgaard. Design of Prodrugs. Elsevier, 1985).

The term "purified" or "to purify" or "substantially purified" refers to the removal of a component such as inactive, inhibitory components, unreacted compounds, or alternative compounds produced during synthesis, (e.g., contaminants) from a composition to the extent that 10% or less (e.g., 10%, 9%, 8%, 7%, 6%, 5%, 4%, 3%, 2%, 1% or less) of the composition is not active compounds or pharmaceutically acceptable carrier.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," J. Pharma. Sci. 1977; 66:1).

The term "pharmaceutically acceptable salts" includes, but is not limited to, salts well known to those skilled in the art, for example, mono-salts (e.g. alkali metal and ammonium salts) and poly salts (e.g. di- or tri-salts,) of the compounds of the invention. Pharmaceutically acceptable salts of compounds of the disclosure are where, for example, an exchangeable group, such as hydrogen in —OH, —NH—, or —P(=O)(OH)—, is replaced with a pharmaceutically acceptable cation (e.g. a sodium, potassium, or ammonium ion) and can be conveniently be prepared from a corresponding compound disclosed herein by, for example, reaction with a suitable base. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The terms "selenium-enriched yeast" and "selenized yeast" refer to any yeast (e.g., *Saccharomyces cerevisiae*) that is cultivated in a medium containing inorganic selenium salts. The present application is not limited by the selenium salt used. Indeed, a variety of selenium salts are contemplated to be useful in the present application including, but not limited to, sodium selenite, sodium selenate, cobalt selenite or cobalt selenate. A selenium-containing compound in such yeast preparations is selenomethionine which will be present in a form that is incorporated into polypeptides/ proteins. The amount of total cellular selenium present in the form of selenomethionine in such preparations will vary, but can be between 10 and 100%, 20-60%, 50-75% and between 60 and 75%. The remainder of the organic selenium in selenized yeast preparations is predominantly made up of intermediates in the pathway for selenomethionine biosynthesis. These include, but are not limited to, selenocysteine, selenocystathionine, selenohomocysteine and seleno-adenosylselenomethionine. The amount of residual inorganic selenium salt in the finished product is generally quite low (e.g., <2%).

The term "substituted" in connection with a moiety refers to a further substituent which is attached to the moiety at any acceptable location on the moiety. Unless otherwise indicated, moieties can bond through a carbon, nitrogen, oxygen, sulfur, or any other acceptable atom. Examples of substituents include, but are not limited to amines, alcohols, thiols, ethers, alkenes, alkynes, epoxides, aziridines, oxiranes, azetidines, dihydrofurans, pyrrolidines, pyrans, piperidines, aldehydes, ketones, esters, carboxylic acids, carboxylates, imines, imides, azides, azo groups, eneamines, alkyl halides, alkenyl halides, alkynyl halides, aryl halides, phosphines, phosphine oxides, phophinites, phosphonites, phosphites, phohsphonates, phosphates, sulfates, sulfoxides, sulfonyl groups, sulfoxyl groups, sulfonates, nitrates, nitrites, nitriles, nitro groups, nitroso groups, cyanates, thiocyanates, isothiocyanates, carbonates, acyl halides, peroxides, hydroperoxides, hemiacetals, hemiketals, acetals, ketals, orthoesters, orthocarbonate esters, sulfides, disulfides, sulfonic acids, sulfonic acids, thiones, thials, phosphodiesters, boronic acids, boronic esters, boronic acids and boronic esters.

The terms "treating", "treat" or "treatment" refer to therapeutic treatment where the object is to slow down (e.g., lessen or postpone the onset of) an undesired physiological condition, disorder or disease, or to obtain beneficial or desired results such as partial or total restoration or inhibition in decline of a parameter, value, function or result that had or would become abnormal. Beneficial or desired results include, but are not limited to, alleviation of symptoms; diminishment of the extent or vigor or rate of development of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether or not it translates to immediate lessening of actual clinical symptoms, or enhancement or improvement of the condition, disorder or disease.

The term "reagent(s) capable of specifically detecting gene expression" refers to reagents capable of or sufficient to detect the expression of various genes described in detail herein. Examples of suitable reagents include, but are not limited to, nucleic acid probes capable of specifically hybridizing to mRNA or cDNA, and antibodies (e.g., monoclonal or polyclonal antibodies).

The term "toxic" refers to any detrimental or harmful effects on a subject, a cell, or a tissue as compared to the same cell or tissue prior to the administration of the toxicant.

Compounds and Compositions

One aspect of the present application is directed to 5'-Methylselenoadenosine ("compound C"), Se-Adenosyl-L-homocysteine ("compound D"), Gamma-glutamyl-methylseleno-cysteine ("compound E") and analogs thereof. Some embodiments include a composition comprising an compound of Formula I, Formula II, and/or Formula III and combinations thereof.

In some embodiments, a composition is provided comprising a compound according to formula (I):

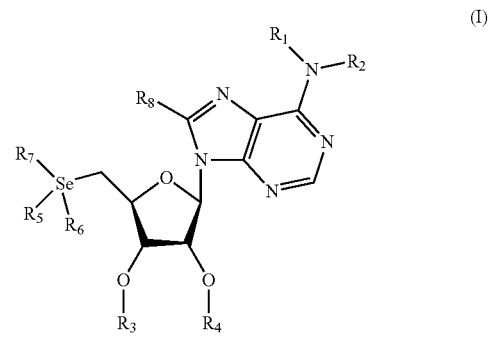

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_7$ is H, alkyl, alkenyl, alkynyl, ketone, amino alcohol, amino acid, OR', Se—R', S—R', where R' is selected from H, alkyl, cycloalkyl, aryl, aralkyl, or heterocyclyl; and $R_8$ is hydrogen, azido, alkyl, alkenyl, alkynyl.

In further embodiments, one or more of these compounds of Formula (I) can be isolated and/or purified.

In some embodiments, a composition is provided comprising a compound according to formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', or C(O)OR', where R' is selected from alkyl, cycloalkyl, aryl, aralkyl, or heterocyclyl; $R_5$ and $R_6$ are each absent; and $R_7$ is alkyl, or amino acid.

In some embodiments, a composition is provided comprising a compound according to formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; $R_5$ and $R_6$ are each absent; and $R_7$ is alkyl, or amino acid; with the proviso that 5'-selenoadenosyl methionine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se (methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In a specific aspect, a composition is provided comprising a compound, or a pharmaceutically acceptable salt, hydrate, or prodrug thereof, according to formula (I) that is 5'-methylselenoadenosine ("compound C").

In some embodiments, compositions comprise a compound according to formula (I), or a pharmaceutically acceptable salt, hydrate, or prodrug thereof, with the proviso that 5'-selenoadenosyl methionine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In some embodiments, a composition is provided comprising a compound according to formula (II):

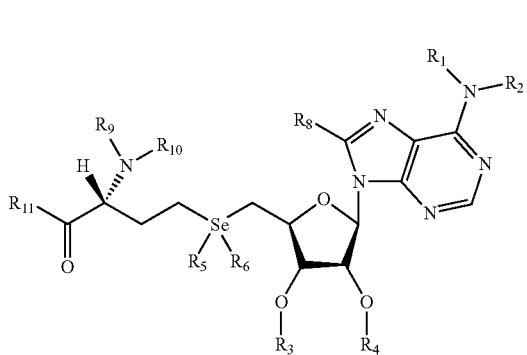

(II)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_8$ is hydrogen, azido, alkyl, alkenyl, alkynyl;

$R_9$ is H, acyl, alkyl, alkenyl, alkynyl, aralkyl, carboxyl, cycloalkyl, C(O)R', C(O)OR', where R' is alkyl, cycloalkyl, aryl, aralkyl, or heterocyclyl; or $R_9$ together with $R_{10}$ form a heterocyclic ring having 4 to 8 ring members with at least one heteroatom selected from oxygen or nitrogen;

$R_{10}$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_9$ together with $R_{10}$ form a heterocyclic ring having 4 to 8 ring members with at least one heteroatom selected from oxygen or nitrogen; and $R_{11}$ is OH, OR, alkoxy, aralkoxy, or amino, where R is selected from alkyl, cycloalkyl, aryl, aralkyl, heterocyclyl, or a pharmaceutically acceptable salt, or inner salt.

In further embodiments, one or more of these compounds of Formula (II) can be isolated and/or purified.

In some embodiments, a composition is provided comprising a compound according to formula (II), or a pharmaceutically acceptable salt, hydrate, or prodrug thereof, wherein $R_1$, $R_3$, $R_4$, $R_8$ and $R_9$ are each H; $R_2$ is H, acyl, alkyl, carboxyl, C(O)R', or C(O)OR', where R' is selected from alkyl, cycloalkyl, aryl, aralkyl, or heterocyclyl; $R_5$ and $R_6$ are absent; $R_{10}$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; and $R_{11}$ is OH, OR, alkoxy, aralkoxy, or amino, where R is selected from alkyl, cycloalkyl, aryl, aralkyl, heterocyclyl, or a pharmaceutically acceptable salt, or inner salt.

In some embodiments, a composition is provided comprising a compound according to formula (II), or a pharmaceutically acceptable salt, hydrate, or prodrug thereof, wherein $R_1$, $R_2$, $R_3$, $R_4$, $R_5$, $R_6$, $R_7$, $R_8$, $R_9$, $R_{10}$ are as defined above and wherein $R_{11}$ is OH or OR, where R is selected from methyl, ethyl, propyl, isopropyl, butyl, sec-butyl, or tert-butyl.

In a specific aspect, a composition is provided comprising a compound according to formula (II), or a pharmaceutically acceptable salt, hydrate, or prodrug thereof, that is 5'-selenoadenosyl homocysteine (compound "D"), or a pharmaceutically acceptable salt, hydrate, or prodrug thereof.

In some embodiments, compositions comprise a compound according to formula (II), or a pharmaceutically acceptable salt, hydrate, or prodrug thereof; with the proviso that 5'-selenoadenosyl methionine, allylselenoadenosyl homocysteine, seleno-adenosyl homocysteine, and selenohydroxy adenosyl homocysteine may each be excluded from the composition.

In some embodiments, a composition is provided comprising a compound according to formula (III):

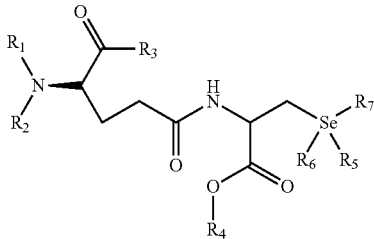

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is OH, OR, alkoxy, aralkoxy, or amino, where R is selected from alkyl, cycloalkyl, aryl, aralkyl, heterocyclyl, or a pharmaceutically acceptable salt, or inner salt;

$R_4$ is H, alkyl, alkenyl, alkynyl, cycloalkyl, aryl, aralkyl, heterocyclyl, or a pharmaceutically acceptable salt, or inner salt;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl; and $R_7$ is H, alkyl, alkenyl, alkynyl, ketone, OR', Se—R', S—R', where R' is selected from H, alkyl, cycloalkyl, aryl, aralkyl, or heterocyclyl.

In some embodiments, a composition is provided comprising or a compound according to formula (III), or a pharmaceutically acceptable salt, hydrate, or prodrug thereof, wherein $R_1$ and $R_2$ are each H;

$R_3$ is OH, OR, alkoxy, aralkoxy, or amino, where R is selected from alkyl, cycloalkyl, aryl, aralkyl, heterocyclyl, or a pharmaceutically acceptable salt, or inner salt;

$R_4$ is H, or a pharmaceutically acceptable salt, or inner salt;

$R_5$ and $R_6$ are absent; and $R_7$ is alkyl, alkenyl or alkynyl.

In further embodiments, one or more of these compounds of Formula (III) can be isolated and/or purified.

In some embodiments, a composition is provided comprising a compound according to formula (III), or a pharmaceutically acceptable salt, hydrate, or prodrug thereof, wherein $R_1$ and $R_2$ are each H; $R_3$ is OH or OR, where R is selected from methyl, ethyl, propyl, isopropyl, butyl, sec-butyl, or tert-butyl; $R_4$ is H; $R_5$ and $R_6$ are absent; and $R_7$ is alkyl that is methyl, ethyl, propyl, isopropyl, butyl, isobutyl, sec-butyl, or tert-butyl.

In some embodiments, a composition is provided comprising a compound according to formula III, or a pharmaceutically acceptable salt, hydrate, or prodrug thereof, wherein $R_1$ and $R_2$ are each H; $R_3$ is OH or OR, where R is selected from methyl, ethyl, propyl, isopropyl, butyl, sec-butyl, or tert-butyl; $R_4$ is H; $R_5$ and $R_6$ are absent; and $R_7$ is methyl.

In a specific aspect, a composition is provided comprising a compound according to formula (III), or a pharmaceutically acceptable salt, hydrate, or prodrug thereof, that is gamma-glutamyl-methylseleno-cysteine ("compound E"), or a pharmaceutically acceptable salt, hydrate, or prodrug thereof.

In some embodiments, a composition comprises a compound according to formula (III), or a pharmaceutically acceptable salt, hydrate, or prodrug thereof, with the proviso that γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, and selenoglutathione-γ-glutamoylcysteine may each be excluded from the composition.

In some embodiments, a composition is provided comprising one or more compounds according to one or more of formulas (I), (II) and/or (III), wherein each of the following compounds is excluded from the composition in order to minimize selenium toxicity, remove inactive or inhibitory compounds, and/or maximize the therapeutic index of the composition, wherein the excluded compounds are γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, selenoadenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selenoxide, and seleno-adenosyl-Se(methyl)-selenoxide.

In embodiments, any of the compounds described herein can be modified with a prodrug to prolong half-life, to protect the compound against oxidation, to target the compound to a tissue, and/or to allow the compound to pass the blood brain barrier.

In embodiments, a prodrug comprises a selenoglycoside. Glycosides include mono, di and oligo saccharides. Saccharides can include ribose, glucose, galactose, or mannose. For example a galactose conjugated to a selenium moiety could target the compound to the liver.

In other embodiments, a prodrug comprises a selenazolidine. These compounds provide for slow release of the compound.

In yet other embodiments, a prodrug comprises conjugation of a seleno-organic compound as described herein to a vitamin such as C or E. These prodrug conjugates have improved protective effects.

In yet other embodiments, a prodrug is a cytochrome P450 activated prodrug. For example, cyclic phosphates or phosphonates. In particular, nucleosides have been modified with these molecules and provide for targeting of molecules to the liver. Exemplary prodrugs include HepDirect prodrugs. Other embodiments of cytochrome P450 activated prodrug improve bioavailability and are described in Huttunen et al, Current Medicinal Chemistry 2008 15:2346.

In embodiments, any of the compounds of formula (I), Formula (II), Formula (III) can be modified to reduce oxidation of selenium. In embodiments, compounds can form a dimer through linkage between selenium atoms.

In embodiments, any of the compounds of formula (I), Formula (II), Formula (III) can be modified by linkage to a tissue targeting agent or other agent for increasing half-life of the compound. In embodiments, tissue targeting agents include antibodies specific for binding to a tissue specific antigen, a transferrin receptor, or a prodrug as described herein.

In other embodiments, the compounds can be linked to or combined with a polymeric carrier or nanoparticle carrier to deliver compositions to the brain and to provide for other tissue targeting. Such polymeric carriers include, but are not limited to, polyethylene glycol, polylactides, polyglycolides, polyorthoesters, polyvinyl pyrrolidone, and polyvinyl alcohols. Microspheres and liposomes include polydilactic coglycolic acid (PLGA) microspheres. Other nanoparticles include phospholipids, chitosan, lactic acid, and dextran.

Lipid prodrugs are also suitable for use with the compounds of the invention. By non-limiting example, certain lipid prodrugs are described in Hostetler et al., (1997 Biochem. Pharm. 53:1815-1822), and Hostetler et al., 1996 Antiviral Research 31:59-67), both of which are incorporated in their entirety herein by reference. Additional examples of suitable prodrug technology is described in WO 90/00555; WO 96/39831; WO 03/095665A2; U.S. Pat. Nos. 5,411,947; 5,463,092; 6,312,662; 6,716,825; and U.S. Published Patent Application Nos. 2003/0229225 and 2003/0225277 each of which is incorporated in their entirety herein by reference. Such prodrugs may also possess the ability to target the drug compound to a particular tissue within the patient, e.g., liver, as described by Erion et al., (2004 J. Am. Chem. Soc. 126:5154-5163; Erion et al., Am. Soc. Pharm. & Exper. Ther. DOI:10.1124/jept.104.75903 (2004); WO 01/18013 A1; U.S. Pat. No. 6,752,981), each of which is incorporated in their entirety herein by reference. By way of non-limiting example, other prodrugs suitable for use with the compounds of the invention are described in WO 03/090690; U.S. Pat. No. 6,903,081; U.S. Patent Application No. 2005/0171060A1; U.S. Patent Application No. 2002/0004594A1; and by Harris et al., (2002 Antiviral Chem & Chemo. 12: 293-300; Knaggs et al., 2000 Bioorganic & Med. Chem. Letters 10: 2075-2078) each of which is incorporated in their entirety herein by reference.

In some embodiments, a composition is provided comprising one or more compounds each according to formula (I). In some aspects, the composition comprising one or more compounds each according to formula (I) comprises 5'-methylselenoadenosine, or a pharmaceutically acceptable salt, hydrate, or prodrug thereof; and 5'-selenoadenosyl homocysteine, or a pharmaceutically acceptable salt, hydrate, or prodrug thereof.

In some embodiments, a composition is provided comprising one or more compounds each according to formula (I) and formula (III). In some aspects, the composition comprising one or more compounds each according to formula (I) and formula (III) comprises 5'-methylselenoadenosine, or a pharmaceutically acceptable salt, hydrate, or prodrug thereof; 5'-selenoadenosyl homocysteine, or a pharmaceutically acceptable salt, hydrate, or prodrug thereof; and gamma-glutamyl-methylseleno-cysteine, or a pharmaceutically acceptable salt, hydrate, or prodrug thereof.

In some embodiments, the composition comprising one or more compounds each according to formula (I) and formula (III) comprises 5'-methylselenoadenosine, or a pharmaceutically acceptable salt, hydrate, or prodrug thereof; and gamma-glutamyl-methylseleno-cysteine, or a pharmaceutically acceptable salt, hydrate, or prodrug thereof.

In some embodiments, a composition is provided comprising one or more compounds each according to formula (II) and formula (III). In some aspects, the composition comprising one or more compounds each according to formula (II) and formula (III) comprises 5'-selenoadenosyl homocysteine, or a pharmaceutically acceptable salt, hydrate, or prodrug thereof; and gamma-glutamyl-methylseleno-cysteine, or a pharmaceutically acceptable salt, hydrate, or prodrug thereof.

According to another aspect, the present invention provides a pharmaceutical composition, which comprises a therapeutically-effective amount of one or more compounds of the present invention or a pharmaceutically-acceptable salt, ester or prodrug thereof, together with a pharmaceutically-acceptable diluent or carrier. Pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions may be formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions.

As is well known in the medical arts, dosages for any one subject may depend upon many factors, including the patient's size, body surface area, age, the particular compound to be administered, sex, time and route of administration, general health, and interaction with other drugs being concurrently administered. Depending on the target sought to be altered by treatment, pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

Pharmaceutical compositions suitable for use in the present application include compositions wherein the active ingredients (e.g., 5'-Methylselenoadenosine, Se-Adenosyl-L-homocysteine, Gamma-glutamyl-methylseleno-cysteine, a compound of formula I, a compound of formula II, a compound of Formula III, and combinations thereof are contained in an effective amount to achieve the intended purpose. For example, in a preferred embodiment, an effective amount of a pharmaceutical composition comprises an amount of a compound selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof. Determination of effective amounts is well within the capability of those skilled in the art, especially in light of the disclosure provided herein.

Selenized yeast comprising 2% or less inorganic selenium generally contains many selenium containing components. Major selenium components of a typical water extract of selenized yeast are selenoproteins and selenomethionine. Other small molecular weight components with a molecular weight of less than 1000 kilodaltons ("Kda") have been identified, isolated, and purified. Some of the components and compounds present in selenized yeast or a water extract thereof have a less desirable bioactivity or even inhibitory bioactivity on mitochondrial function when isolated from such selenized yeast. Compounds such as glutamyl selenocysteine, and sulfur containing compounds such as 5'-Methylthioadenosine, S-Adenosyl-L-homocysteine, and Gamma-glutamyl-methyl-cysteine are inactive or in some cases inhibitory as described and shown herein.

Some selenium-containing compounds have also been prepared synthetically, purified and screened in a bioactivity assay. Concentration ranges for screening include about 15 to about 500 parts per billion. Bioactivity can be detected even at 15 ppb for the compositions described herein. In embodiments, the bioactivity assay is the mitochondrial potential assay. Not all components and compounds found in selenized yeast or a water extract thereof have biological activity when obtained from such yeast and some inhibit desired biological activity.

In embodiments, synthetically produced selenium-containing compounds are formulated in compositions in ratios that differ from that present in the water extract. For example, a typical water extract would have a ratio of Gamma-glutamyl-methylseleno-cysteine to 5'-Methylselenoadenosine or Se-Adenosyl-L-homocysteine of 7 to 1. In embodiments, compositions containing synthetically produced compounds may comprise an equal amount of each selenium-containing compound, for example, a ratio of at least 1:1:1 of Gamma-glutamyl-methylseleno-cysteine to 5'-Methylselenoadenosine to Se-Adenosyl-L-homocysteine. In other embodiments, a composition may comprise at least two components in ratios of 5:1 to 1:1.

Compositions comprising one or more compounds including 5'-Methylselenoadenosine, Se-Adenosyl-L-homocysteine, Gamma-glutamyl-methylseleno-cysteine, a compound of formula (I), a compound of formula (II), a compound of Formula III, and combinations thereof can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art.

Compositions comprising selenium are useful for intravenous administration as well as parenteral administration, such as intravenous, subcutaneous, intramuscular, and intraperitoneal. For injection, a composition comprising selenium (e.g., a pharmaceutical composition) of the present application may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

Compositions comprising 5'-Methylselenoadenosine, Se-Adenosyl-L-homocysteine, Gamma-glutamyl-methylseleno-cysteine, a compound of formula (I), a compound of formula (II), a compound of formula (III), and combinations thereof may be added to a nutritional drink or food (e.g., ENSURE, POWERBAR, or the like), a multi-vitamin, nutritional products, food products, etc. for daily consumption.

In other embodiments, compositions of the present application can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

In some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In embodiments, the compositions may include one or more amino acids or selenoamino acids, such as methionine, cysteine, or selenocysteine in order to minimize toxicity. In one embodiment of the present application, the pharmaceutically acceptable carrier is pharmaceutically inert. In another embodiment of the present application, compositions comprising selenium may be administered alone to individuals subject to, at risk of, or suffering from a disease or condition associated with mitochondrial dysfunction.

Methods of Using Compounds and Compositions

As described herein, the compounds and combinations thereof are useful to enhance mitochondrial function, to treat mitochondrial dysfunction, to treat Alzheimer's disease, and to modulate glucose metabolism in a tissue-specific and tissue-appropriate manner.

A. Mitochondrial Function and Dysfunction

Mitochondria are the main energy-producing organelles in cells of higher organisms. Mitochondria provide direct and indirect biochemical regulation of a wide array of cellular respiratory, oxidative and metabolic processes. These include electron transport chain (ETC) activity, which drives oxidative phosphorylation to produce metabolic energy in the form of adenosine triphosphate (ATP), and which also underlies a central mitochondrial role in intracellular calcium homeostasis.

In addition to their role in energy production in growing cells, mitochondria (or, at least, mitochondrial components) participate in programmed cell death (PCD), also known as apoptosis (See, e.g., Newmeyer et al., Cell 1994, 79:353-364; Liu et al., Cell 1996, 86:147-157). Apoptosis is required for normal development of the nervous system, and for proper functioning of the immune system. Moreover, some disease states are thought to be associated with either insufficient or excessive levels of apoptosis (e.g., cancer and autoimmune diseases, and stroke damage and neurodegeneration in Alzheimer's disease in the latter case, respectively). The role of mitochondria in apoptosis has been documented (See, e.g., Green and Reed, Science, 1998, 281:1309-1312; Green, Cell, 1998, 94:695-698; and Kromer, Nature Medicine, 1997, 3:614-620).

Mitochondria-associated diseases (e.g., caused by dysfunctional mitochondria) may also be related to loss of mitochondrial membrane electrochemical potential by mechanisms other than free radical oxidation, and permeability transition may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of diseases associated with altered mitochondrial function, including degenerative diseases as well as diseases/conditions associated with aging (e.g., cancer, cardiovascular disease and cardiac failure, type 2 diabetes, Alzheimer's and Parkinson's diseases, fatty liver disease, cataracts, osteoporosis, muscle wasting, sleep disorders and inflammatory diseases such as psoriasis, arthritis and colitis). The methods as described herein are useful to enhance mitochondrial function whether or not the cells in a subject are in a stressed or diseased condition.

The compounds and compositions as disclosed herein exhibit tissue specificity regarding their effects on mitochondrial function.

Embodiments include a method or use of enhancing mitochondrial function in one or more kidney cells comprising: administering an effective amount of the composition to the cells, the composition comprising a compound selected from the group consisting of 5'-Methylselenoadenosine, a compound of Formula I, and mixtures thereof, wherein the effective amount enhances mitochondrial function as compared to cells not treated with the composition. In further embodiments, one or more compounds can be isolated and/or purified.

In embodiments, the composition may exclude one or more of Se-Adenosyl-L-homocysteine, Gamma-glutamyl-methylseleno-cysteine, glutamyl selenocysteine, a compound of formula III, 5'-Methylthioadenosine, or S-Adenosyl-L-homocysteine.

In embodiments, the present application provides a use of a composition comprising a compound selected from the group consisting of 5'-Methylselenoadenosine, a compound of Formula I and mixtures thereof, wherein the effective amount enhances mitochondrial function in a kidney cell.

In embodiments, a composition comprises a compound selected from the group consisting of 5'-Methylselenoadenosine and/or a compound of formula I. In embodiments, compositions for enhancing mitochondrial function in kidney cells may not include one or more of Se-Adenosyl-L-homocysteine, Methylthioadenosine, or S-Adenosyl-L-homocysteine.

Embodiments of the present application include a method or use of enhancing mitochondrial function in one or more cells selected from the group consisting of skeletal muscle cell, neuronal cell, and combinations thereof, said method comprising: administering an effective amount of the composition to the cells, the composition comprising a compound selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof, wherein the effective amount enhances mitochondrial function as compared to cells not treated with the composition. In further embodiments, one or more compounds can be isolated and/or purified.

In embodiments, the present application provides a use of a composition comprising a compound selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof, wherein the effective amount enhances mitochondrial function in in one or more cells selected from the group consisting of skeletal muscle cell, neuronal cell, and combinations thereof.

In embodiments, a composition comprises a compound selected from the group consisting of 5'-Methylselenoadenosine, Se-Adenosyl-L-homocysteine, a compound of formula I, a compound of Formula II, and combinations thereof. In embodiments, compositions for enhancing mitochondrial function in muscle cells may not include one or more of Methylthioadenosine, or S-Adenosyl-L-homocysteine. While not meant to limit the scope of the present application, Methylthioadenosine or S-Adenosyl-L-homocysteine exhibit toxic effects on mitochondrial function in skeletal muscle cells.

The presence of certain sulfur-containing molecules in commonly used selenium supplements, such as selenium-enriched yeast, may, in some cases, inhibit mitochondrial activity and lead, over time, to a pro-diabetic state. It is well documented in the literature that adult-onset diabetes is linked to a gradual decline in mitochondrial activity over a period of several years. This is particularly important in the case of skeletal muscle which, it is estimated, uses 75-80% of daily ingested glucose. Even modest declines (e.g. a 20% inhibition) in the ability of muscle mitochondria to efficiently burn glucose can, over time, lead to serious health problems. The two-fold stimulation of mitochondrial activity noted in skeletal muscle cells in response to compound Se-Adenosyl-L-homocysteine, for example, may represent a way to avoid or delay mitochondrial decline in the muscle tissue of pre-diabetic or diabetic subjects.

In embodiments, a composition for enhancing mitochondrial function in neuronal cells comprises a compound selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof. In further embodiments, one or more compounds can be isolated and/or purified. In embodiments, compositions for enhancing mitochondrial function in neuronal cells may not include one or more of selenomethionine, or glutamylselenocysteine.

In embodiments, a composition for enhancing mitochondrial function in neuronal cells comprises a compound selected from the group consisting of Se-Adenosyl-L-homocysteine, and/or a compound of formula II and at least one other selenium compound selected from the group consisting of 5'-Methylselenoadenosine, Gamma-glutamyl-methylseleno-cysteine, a compound of formula I, a compound of Formula III and combinations thereof.

In embodiments, a composition for enhancing mitochondrial function in neuronal cells comprises a composition comprising a compound selected from the group consisting of 5'-Methylthioadenosine, S-Adenosyl-L-homocysteine, Gamma-glutamyl-methyl-cysteine, and combinations thereof. In embodiments, a composition targeted to neuronal cells may contain one or more sulfur analogs that enhance the mitochondrial activity in neuronal cells.

Other embodiments include a method or use of enhancing mitochondrial function in one or more liver cells comprising: administering an effective amount of the composition to the cells, the composition comprising at least three different compounds selected from the group consisting of 5'-Methylselenoadenosine, Se-Adenosyl-L-homocysteine, Gamma-glutamyl-methylseleno-cysteine, a compound of formula I, and a compound of formula III, wherein the effective amount enhances mitochondrial function as compared to cells not treated with the composition. In further embodiments, one or more compounds can be isolated and/or purified.

In embodiments, the present application provides a use of a composition comprising at least three different compounds selected from the group consisting of 5'-Methylselenoadenosine, Se-Adenosyl-L-homocysteine, Gamma-glutamyl-methylseleno-cysteine, a compound of formula I, and a compound of formula III, for enhancing mitochondrial function in liver cells.

In embodiments, a composition for enhancing mitochondrial function in one or more liver cells comprises at least three compounds selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof to enhance mitochondrial function in liver cells. In embodiments, a composition may exclude one or more compounds selected from the group consisting of 5'-Methylthioadenosine, S-Adenosyl-L-homocysteine, glutamyl-methyl-cysteine, and combinations thereof.

In embodiments, the enhancement of mitochondrial function ranges from an approximately 50% increase to a 500% increase as compared to a cell of identical type not treated with the compound. The magnitude of the response depends on the cell type, the specific compound and the time in contact with the cell. In embodiments, the effect on mitochondrial function is about −66% to +200% as compared to a cell of the same type treated with one or more sulfur analogs of the selenium compounds. In the case of some cell types, the sulfur analogs have no measurable effect on mitochondrial activity, in others they are inhibitory and in others still, they are stimulatory.

In embodiments, one or more of the compounds have a tissue specific effect on the expression of uncoupling proteins. Uncoupling proteins (UCP) in mitochondria (MT) are important for thermogenesis and maintenance of mitochondrial potential or integrity. Loss of UCP2 has been documented to cause shorter lifespan and elevated production of reactive oxygen species (ROS) in MT (See, e.g., Andrews et al. Am J Physiol Endocrinol Metab, 2009. 296(4): p. E621-7; Andrews et al., Curr Aging Sci, 2010. 3(2): p. 102-12). However, because UCPs uncouple electron transport in mitochondria they have the net result of lowering ATP production from glucose in a cell. It is well known that the production of mitochondrial ATP is critical for glucose-stimulated insulin secretion (GSIS) by pancreatic beta-cells. In fact, it has been shown that inhibition of one UCP in particular, UCP2, reverses diet-induced diabetes by positively affecting both insulin secretion and action (De Souza et al., FASEB J, 2007, 21(4): 1153-1163.

In embodiments, a method or use of downregulating Ucp2 and/or Ucp3 gene expression in a neuronal cell comprises: administering an effective amount of a composition to the cells, the composition comprising a compound selected from the group consisting of 5'-Methylselenoadenosine, Se-Adenosyl-L-homocysteine, Gamma-glutamyl-methylseleno-cysteine, a compound of formula I compound of formula II, a compound of formula III, and combinations thereof, wherein the effective amount downregulates expression of Ucp2 and/or Ucp3 in neuronal cells as compared to cells not treated with the composition. In further embodiments, one or more compounds can be isolated and/or purified.

In embodiments, the present application provides a use of a composition comprising a compound selected from the group consisting of 5'-Methylselenoadenosine, Se-Adenosyl-L-homocysteine, Gamma-glutamyl-methylseleno-cysteine, a compound of formula I compound of formula II, a compound of formula III, and combinations thereof, for downregulating Ucp2 and/or Ucp3 gene expression in a neuronal cell.

In other embodiments, a method or use of downregulating Ucp2 gene expression in a liver cell comprises: administering an effective amount of the composition to the cells, the composition comprising at least three compounds selected from the group consisting of 5'-Methylselenoadenosine, Se-Adenosyl-L-homocysteine, Gamma-glutamyl-methylseleno-cysteine, a compound of formula I compound of formula II, a compound of formula III, and combinations thereof, wherein the effective amount downregulates expression of Ucp2 in liver cells as compared to cells not treated with the composition. In further embodiments, one or more compounds can be isolated and/or purified.

In embodiments, the present application provides a use of a composition comprising at least three different compounds selected from the group consisting of 5'-Methylselenoadenosine, Se-Adenosyl-L-homocysteine, Gamma-glutamyl-methylseleno-cysteine, a compound of formula I, and a compound of formula III, for downregulating Ucp2 and/or Ucp3 gene expression in a liver cell.

Methods of determining gene expression in a cell are known to those of skill in the art and include hybridization with probes such as on an array or by PCR methods. Arrays and/or primers for determining gene expression are commercially available. Primers can readily be designed using exemplary sequences for Ucp1, Ucp2 and/or Ucp3. Exemplary sequences for Ucp 1 are found at NM_021833/gI194733736, Ucp2 are found at NM_003355/gI13259540, and for Ucp3 are found at NM_003356/gI 215273349.

In embodiments, the effective amount of compounds and compositions as described herein is an amount effective to enhance mitochondrial function without being toxic to the cells. Enhancing mitochondrial function can be determined using a number of assays on a sample taken from a subject treated in accord with the compositions described herein. The effective amounts selected do not show toxicity for any of the exemplified cells including kidney, mouse skeletal, human neuronal, or mouse liver cells.

As is well known in the medical arts, dosages for any one subject may depend upon many factors, including the patient's size, body surface area, age, the particular compound to be administered, sex, time and route of administration, general health, and interaction with other drugs being concurrently administered.

In embodiments, the effective amount of a composition to administer to a subject for enhancing mitochondrial function in one or more kidney, neuronal, liver, or skeletal muscle cells is about at least 5 ug or greater or 800 ug or less per day of a single desirable biologically active selenium-containing compound or multiple desirable biologically active selenium-containing compounds. When multiple desirable biologically active selenium-containing compounds are present, the effective amount of the composition is the total for all desirable biologically active selenium-containing compounds in the composition.

In embodiments, an effective amount to administer to a subject is about 5 ug to about 800 ug and every number in between, 5 ug to about 700 ug and every number in between, 5 ug to about 600 ug and every number in between, 5 ug to about 500 ug and every number in between, 5 ug to about 400 ug and every number in between, 5 ug to about 300 ug and every number in between, 5 ug to about 200 ug and every number in between, 5 ug to about 100 ug and every number in between, or 5 ug to 50 ug and every number in between.

In embodiments of compositions comprising desirable biologically active selenium-containing compounds as described herein, an effective amount to administer to a subject is preferably 200 ug or less per day or 50 ug or less per day. In embodiments, the dose may be adjusted depending on efficacy or whether any overt signs of selenium toxicosis, such as garlicky breath, hair loss, or flaky nails are observed in the subject.

In embodiments, in compositions that comprise at least two or more compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof the compounds are present in the composition in equal proportions. In other embodiments the ratio of one desirable biologically active selenium-containing compound to another can be about 4:1 to 1:1.

In embodiments, the dose is administered at least once daily for a period of time to achieve a steady state of elemental selenium in the blood. In embodiments, the dose is administered daily for at least 60 or 90 days. In embodiments, the dose is administered while the subject is experiencing symptoms of the disease or disorder. In embodiments, the subject is at an age where the risk of mitochondrial related diseases is increased, e.g. at least 40 years of age.

The methods of the present application find use in treating (e.g., prophylactically or therapeutically) a subject (e.g., a subject with a condition associated with mitochondrial dysfunction). While not meant to limit the scope of the disclosure, evidence has been presented that three synthetic organoselenium compounds have the ability, either singly or in various combinations, to significantly increase mitochondrial activity in diverse cell types; namely, kidney cells, skeletal muscle cells, neuronal cells and liver cells. Mechanistically, modulation of UCPs may offer one explanation for this increase and we present evidence below that the expression of other proteins, critical to mitochondrial function and biogenesis, may also be favorably affected by these compounds. Regardless of mechanism of action, however, the fact that these compounds can stimulate mitochondrial activity in a cross-tissue manner means that they may be particularly valuable in ameliorating the onset and progress of seemingly diverse diseases; for example, Alzheimer's disease (AD) and Type2Diabetes (T2DM).

Compositions comprising one or more of compounds including 5'-Methylselenoadenosine, Se-Adenosyl-L-homocysteine, Gamma-glutamyl-methylseleno-cysteine, a compound of formula I, a compound of formula II, a compound of Formula III, and combinations thereof can be administered to a subject (e.g., a patient) in any number of ways as described herein.

In embodiments for delivery to skeletal muscles, the compositions as described herein can be applied topically in the form of a gel, a patch or a cream.

In other embodiments, delivery to the brain can be targeted by using liposomes or PLGA spheres having an antibody, transferrin receptor, or prodrug as a targeting agent.

In other embodiments, delivery to the liver can be targeted by using targeted prodrugs as described herein, including HepDirect or selenoglycosides.

Accordingly, in some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers.

In another embodiment of the present application, compositions comprising seleno-organic compounds described herein may be administered alone to individuals subject to, at risk of, or suffering from a disease or condition associated with mitochondrial dysfunction. Such diseases include diabetic kidney disease, Alzheimer's disease, and type II diabetes.

B. Alzheimer's Disease

Alzheimer's Disease ("AD") is the 6th leading cause of death in the United States of America ("USA") and is the most common form of dementia. Currently, this disease is estimated to affect 5.1 million people aged 65 and over in the USA. AD is histopathologically characterized by two hallmark lesions Aβ plaques (See Kumar et al., 2000) and NFTs which are composed of hyper-phosphorylated forms of the microtubule-associated protein tau (See Dunckley et al., published online 2005 Oct. 19, 2005, and paragraphs 155-163 of the published patent Application-201110038889 AI). There exists abundant evidence in the literature that both Aβ and NFTs are crucial partners in the pathogenesis of Alzheimer's disease and that they act individually and in concert to maximize cognitive impairment and neuronal loss in affected individuals. Mutations in amyloid precursor protein (APP) induce AD with 100% penetration, and familial AD (FAD)-associated mutations of APP, presenilin-I (PSEN) and presenilin-2 (PSEN-2) lead to an increased level of amyloid β generation and Aβ aggregation.

Moreover, the APP-overexpressing mouse (APP-Tg) exhibits Aβ deposition and memory impairment without forming NFTs or suffering neuronal loss. Plaques are formed when amyloid precursor protein (APP) is aberrantly processed by two enzymes called β secretase and γ-secretase, resulting in the formation of the 39 to 42 amino acid peptide of β amyloid. The γ-secretase enzyme is actually a multi-enzyme complex which incorporates presenilin-I (PSEN) and presenilin-2 (PSEN-2) as two key components.

Accumulation of Aβ is associated with loss of memory in AD models and a reduction in APP expression reverses this loss (See Kumar et al., Peptides 21:1769 2000). Therefore, reduction in APP expression (either at a gene or protein level) is understood by practitioners as an approach to take to counter age-dependent or neurodegenerative disorders like AD that involve memory loss.

Modulation or inhibition of PSEN, PSEN-2, Nicastrin (which controls protein trafficking in the γ-secretase complex) has been an important goal of AD therapeutic research and some notable successes have been published. For example, highly specific inhibitors that modulate PSEN activity in human neurons not only affected Aβ generation but also affected the Notch signaling pathway (See Seiffert et al., J Biol. Chem. 275:34086 2000). This was accompanied by changes in neurite morphology and indicated that regulation of γ secretase PSEN-1 activity has clinically beneficial effects on the neuritic pathology of AD (See Figueroa et al., Neurobiology Dis. 9:49 2002). Furthermore, downregulation of PSEN was shown to decrease the secretion of Aβ protein (See Luo et al., Acta Pharmacol. Sin. 25:1613 2004) and inhibition of PSEN in SAMP8 mice was found to significantly improve memory (See Kumar et al., J. Exp. Biol. 212:494 2009).

Thus, Aβ is toxic to neurons, contributes to neuronal cell death and, Aβ levels can be altered in the brain by modulating the levels/activities of its precursor, APP, or the enzyme complex(es) which process APP. A practitioner immediately understands and appreciates that an agent capable of inhibiting APP expression and/or APP processing into Aβ (e.g., B or γ secretase) is a therapeutic target for AD therapy.

The selenium-containing compounds and compositions as disclosed herein affect the gene expression of genes involved in B amyloid processing and tau phosphorylation. In addition, such compounds and compositions exhibit tissue specificity regarding gene expression of genes relating to transcriptional activators.

In embodiments, a method or use for inhibiting B amyloid accumulation in one or more neuronal cells comprises: administering an effective amount of a composition to the one or more neuronal cells, the composition comprising a compound selected from the group consisting of 5'-Methylselenoadenosine, a compound of formula (I), and mixtures thereof wherein the effective amount inhibits B amyloid accumulation in neuronal cells as compared to neuronal cells not treated with the composition.

In embodiments, a method or use for inhibiting B amyloid accumulation in one or more neuronal cells comprises: administering an effective amount of a composition to the one or more neuronal cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount inhibits B amyloid accumulation in neuronal cells as compared to neuronal cells not treated with the composition. In further embodiments, one or more compounds can be isolated and/or purified.

In embodiments, the present application provides a use of a composition comprising a compound selected from the group consisting of 5'-Methylselenoadenosine, a compound of formula (I), or at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) 5'-Methylselenoadenosine, a compound of Formula I and mixtures thereof, for inhibiting B amyloid accumulation in neuronal cells.

In embodiments, a composition comprises a compound selected from the group consisting of 5'-Methylselenoadenosine, a compound of formula (I) and mixtures thereof to inhibit expression of Presenilin 1 (PSEN) and Nicastrin in neuronal cells. In embodiments, the neuronal cells are IMR 32 cells. IMR 32 cells are human neuronal cells that are a model for Alzheimer's disease. (Neill et al., J. Neuroscience Res. 1994 39:482) In embodiments, compositions for inhibiting gene expression in neuronal cells may not include one or more of Se-Adenosyl-L-homocysteine, or Methylthioadenosine.

In embodiments, the present application provides a use of a composition comprising a compound selected from the group consisting of 5'-Methylselenoadenosine, a compound of formula (I), or at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) 5'-Methylselenoadenosine, a compound of Formula I and mixtures thereof, for inhibiting expression of presenilin 1 and nicastrin in neuronal cells.

In embodiments, a composition comprises a compound selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof to inhibit gene expression of nicastrin and presenilin 1 in neuronal cells. In embodiments, compositions for inhibiting gene expression in neuronal cells may not include one or more of selenomethionine or glutamyl selenocysteine.

In embodiments, compositions include 5'-Methylselenoadenosine and/or a compound of formula (I) and at least one other selenium compound selected from the group consisting of Se-Adenosyl-L-homocysteine, Gamma-glutamyl-methylseleno-cysteine, a compound of formula (II), a compound of formula (III) and combinations thereof. In further embodiments, one or more compounds can be isolated and/or purified.

In embodiments, a composition comprises at least three compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof inhibit gene expression in neuronal cells.

In embodiments, a method or use for inhibiting tau phosphorylation in one or more neuronal cells comprises: administering an effective amount of a composition to the one or more neuronal cells, the composition comprising a compound selected from the group consisting of 5'-Methylselenoadenosine, a compound of formula (I), and mixtures thereof, wherein the effective amount inhibits tau phosphorylation in neuronal cells as compared to neuronal cells not treated with the composition.

In embodiments, a method or use for inhibiting tau phosphorylation in one or more neuronal cells comprises: administering an effective amount of a composition to the one or more neuronal cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount inhibits tau phosphorylation in neuronal cells as compared to neuronal cells not treated with the composition. In further embodiments, one or more compounds can be isolated and/or purified.

In embodiments, the present application provides a use of a composition comprising a compound selected from the group consisting of 5'-Methylselenoadenosine, a compound of formula (I), or at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) 5'-Methylselenoadenosine, a compound of Formula I and mixtures thereof, for inhibiting tau phosphorylation in a neuronal cell.

In embodiments, a composition comprises a compound selected from the group consisting of 5'-Methylselenoadenosine and/or a compound of formula I to inhibit expression of Gsk3B in neuronal cells. In embodiments, compositions for inhibiting Gsk3B gene expression in neuronal cells may not include one or more of Se-Adenosyl-L-homocysteine, or Methylthioadenosine.

In embodiments, a composition comprises a compound selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof to inhibit to phosphorylation of tau in neuronal cells. In embodiments, compositions for inhibiting phosphorylation of tau in neuronal cells may not include one or more of methionine or other sulfur containing compounds.

In embodiments, compositions include 5'-Methylselenoadenosine and/or a compound of formula (I) and at least one other selenium compound selected from the group consisting of Se-Adenosyl-L-homocysteine Gamma-glutamyl-methylseleno-cysteine, a compound of formula (II), a compound of formula (III) and combinations thereof.

In embodiments, a composition comprises at least two compounds selected from the group consisting of 5'-Methylselenoadenosine, Gamma-glutamyl-methylseleno-cysteine, a compound of formula I, a compound of Formula III, and combinations thereof to inhibit phosphorylation of tau in neuronal cells.

In embodiments, a composition comprises a compound selected from the group consisting of Gamma-glutamyl-methylseleno-cysteine and/or a compound of formula (III) to inhibit total tau in neuronal cells. In embodiments, compositions for inhibiting total tau in neuronal cells may not include one or more of Se-Adenosyl-L-homocysteine, or Methylthioadenosine.

In embodiments, a method or use for inhibiting FOXO phosphorylation in one or more neuronal cells comprises: administering an effective amount of a composition to the one or more neuronal cells, the composition comprising a compound selected from the group consisting of 5'-Methylselenoadenosine, Se-Adenosyl-L-homocysteine, Gamma-glutamyl-methylseleno-cysteine, a compound of formula (I), a compound of formula (III), and combinations thereof, wherein the effective amount inhibits FOXO phosphorylation as compared to cells not treated with the composition. In further embodiments, one or more compounds can be isolated and/or purified.

In embodiments, the present application provides a use of a composition comprising a compound selected from the group consisting of 5'-Methylselenoadenosine, Se-Adenosyl-L-homocysteine, Gamma-glutamyl-methylseleno-cysteine, a compound of formula (I), a compound of formula (III), and combinations thereof for inhibiting FOXO phosphorylation in neuronal cells.

In embodiments, a method or use for inhibiting FOXO phosphorylation in one or more neuronal cells while enhancing FOXO phosphorylation in one or more liver cells, comprises: administering an effective amount of a composition to the liver and neuronal cells, the composition comprising at least three compounds selected from the group consisting of consisting of: 5'-Methylselenoadenosine, Se-Adenosyl-L-homocysteine, Gamma-glutamyl-methyl-seleno-cysteine, a compound of formula (I), a compound of formula (III), and combinations thereof, wherein the effective amount decreases FOXO phosphorylation in neuronal cells and increases FOXO phosphorylation in liver cells as compared to cells not treated with the composition.

In embodiments, a composition comprises a compound selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof to inhibit phosphorylation of FOXO3 and/or FOXO 4 in neuronal cells. In embodiments, compositions for inhibiting phosphorylation of FOXO 3 and/or FOXO4 in neuronal cells may not include methionine or selenomethionine. In embodiments, compositions include 5'-Methylselenoadenosine and/or a compound of formula (I) and at least one other selenium compound selected from the group consisting of Se-Adenosyl-L-homocysteine, Gamma-glutamyl-methylseleno-cysteine, a compound of formula (II), a compound of formula (III) and combinations thereof.

In embodiments, a composition comprises at least three compounds selected from the group consisting of 5'-Methylselenoadenosine, Se-Adenosyl-L-homocysteine, Gamma-glutamyl-methylseleno-cysteine, a compound of formula (I), a compound of formula(II), a compound of formula (III), and combinations thereof to inhibit phosphorylation of FOXO 3 and FOXO 4 in neuronal cells.

In embodiments, a composition comprises a compound selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof to enhance expression of PGC1a in neuronal cells. In embodiments, compositions for enhancing expression of PGC 1a in neuronal cells may not include methionine or seleno methionine.

In embodiments, the present application provides a use of a composition comprising a compound selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof to enhance expression of PGC1a in neuronal cells.

In embodiments, a method or use of increasing expression of PGC1a in one or more neuronal cells, comprises: administering an effective amount of a composition to the one or more neuronal cells, the composition comprising at least three different compounds selected from the group consisting of: 5'-Methylselenoadenosine, Se-Adenosyl-L-homocysteine, Gamma-glutamyl-methylseleno-cysteine, a compound of formula (I), and a compound of formula (III), wherein the effective amount increases expression PGC1a as compared to cells not treated with the composition.

In embodiments, a method or use for increasing expression of PGC1a in one or more neuronal cells and not affecting expression of PGC1a in one or more liver cells, comprises: administering an effective amount of a composition to the liver and neuronal cells, the composition comprising at least three compounds selected from the group consisting of consisting of 5'-Methylselenoadenosine, Se-Adenosyl-L-homocysteine, Gamma-glutamyl-methyl-seleno-cysteine, a compound of formula (I), a compound of formula (III), and combinations thereof, wherein the effective amount increases expression of PGC1a in one or more neuronal cells and does not affect expression of PGC1a in one or more liver cells as compared to cells not treated with the composition.

In embodiments, compositions comprise a compound selected from the group consisting of 5'-Methylselenoadenosine and/or a compound of formula I and at least one other selenium compound selected from the group consisting of Se-Adenosyl-L-homocysteine, Gamma-glutamyl-methylseleno-cysteine, a compound of formula II, a compound of Formula III and combinations thereof.

In embodiments, a composition comprises at least three compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula(III), and combinations thereof to enhance expression of PGC1 a in neuronal cells.

In embodiments, the enhancement of PGC1a expression, decrease in FOXO phosphorylation, decrease in PSEN, decrease in nicastrin, decrease in Gsk3b ranges from an approximately 50% increase or decrease to a 500% increase or decrease, respectively, as compared to a cell of identical type not treated with the compound. The magnitude of the response depends on the cell type, the specific compound and the time in contact with the cell.

The effects of the compounds and compositions of the present application on the phosphorylation of FOXO 3 and FOXO 4 and on the expression of PGC1a exhibit a tissue specificity. While not meant to limit the present application, in neuronal cells, the inhibition of phosphorylation of FOXO3 and FOXO4 allows FOXO to enter the nucleus and activate transcription. PGC1a is also a transcriptional activator that regulates energy metabolism in the cell including gluconeogenesis. FOXO and PGC1a contribute to transcriptional activation of genes such as glucose-6-phophatase (G6pc). An enhancement of gluconeogenesis would provide neuronal cells with the ability to generate glucose and maintain energy stores.

As discussed above, the generation of Aβ and phosphorylated tau contribute significantly to the pathology of Alzheimer's disease. The results presented herein provide evidence that the compounds and compositions described herein affect gene expression of presenilin 1 and nicastrin. These two enzymes have been shown to be involved in the generation of Aβ. In addition, the inhibition of phosphorylation of tau and/or total tau are evidence that the compounds and compositions as described herein also affect the production of NFT. In addition, the effect of the compounds on enhancing mitochondrial function, enhancing FOXO activation, and increasing gene expression of PGC1a provide neuronal cells with enhanced mitochondrial function that may also work to treat Alzheimer's by minimizing oxidative stress. Previous studies have shown that App transgenic mice fed selenium enriched yeast but not a normal diet or selenium deficient diet had decreased production of B amyloid plaque. (Lovell et al., Free Rad. Biol. Med. 46:1527 2009)

Methods of determining gene expression in a cell are known to those of skill in the art and include hybridization with probes such as on an array or by PCR methods. Arrays and/or primers for determining gene expression are commercially available. Primers can readily be designed using exemplary sequences for PSEN 1, PSEN2, Nicastrin and Gsk3b. Exemplary sequences for PSEN 1 are found at NM_000021/NM_007318, PSEN2 are found at NM_000447/NM_012486, Nicastrin are found at NM_015331 and for Ucp3 are found at NM_002093.

In embodiments, a method or use of treating Alzheimer's disease comprises: administering an effective amount of a composition comprising a compound selected from the group consisting of 5'-Methylselenoadenosine, a compound of formula (I), and combinations thereof to a subject. In embodiments, compositions for treating Alzheimer's disease may not include one or more Methylthioadenosine, or S-Adenosyl-L-homocysteine.

In embodiments, a method or use of treating Alzheimer's disease comprises: administering a compound selected from the group consisting of 5'-Methylselenoadenosine, Se-Adenosyl-L-homocysteine, Gamma-glutamyl-methylseleno-cysteine, a compound of formula (I), a compound of formula II, a compound of Formula III, and combinations thereof. In embodiments, compositions for treating Alzheimer's may not include methionine or selenomethionine.

In embodiments, the present application provides a use of a composition comprising a compound selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof to treat Alzheimer's disease.

In embodiments, compositions include 5'-Methylselenoadenosine and/or a compound of formula (I) and at least one other selenium compound selected from the group consisting of Se-Adenosyl-L-homocysteine, Gamma-glutamyl-methylseleno-cysteine, a compound of formula (II), a compound of formula (III) and combinations thereof. In further embodiments, one or more compounds can be isolated and/or purified.

In embodiments, a method or use of treating Alzheimer's disease further comprises selecting a composition that treats the symptoms of Alzheimer's disease without causing an adverse effect on glucose metabolism in the liver. In embodiments, the composition comprises 5'-Methylselenoadenosine and/or a compound of formula (I). In embodiments, the composition may exclude one or more of Se-Adenosyl-L-homocysteine, Gamma-glutamyl-methylseleno-cysteine, a compound of formula (II), or a compound of formula (III). In embodiments, the composition comprises at least three compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof. In embodiments, the composition excludes one or more of H (5'-Methylthioadenosine), I (S-Adenosyl-L-homocysteine), or J (Gamma-glutamyl-methyl-cysteine).

In embodiments, a composition comprises at least three compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof for treating Alzheimer's disease.

In embodiments, the effective amount of compounds and compositions as described herein is an amount effective to treat Alzheimer's disease without being toxic to the cells. The effective amounts selected do not show toxicity for any of the exemplified cells including kidney, mouse skeletal, human neuronal, or mouse liver cells.

In embodiments, the effective amount of compounds and compositions as described herein is an amount effective to ameliorate symptoms of Alzheimer's disease and/or modulates gene expression as described herein without being toxic to the cells. Modulation of gene expression in neuronal cells can be determined as described herein using a number of assays on a sample taken from a subject treated in accord with the compositions described herein.

As is well known in the medical arts, dosages for any one subject may depend upon many factors, including the patient's size, body surface area, age, the particular compound to be administered, sex, time and route of administration, general health, and interaction with other drugs being concurrently administered.

In embodiments, an effective amount of a composition for treating Alzheimer's, inhibiting B amyloid processing and/or tau phosphorylation in neuronal cells is about 5 ug or greater or 800 ug or less per day of a single desirable biologically active selenium-containing compound or multiple desirable biologically active selenium-containing compounds. When multiple desirable biologically active selenium-containing compounds are present, the effective amount of the composition is the total for all compounds in the composition being administered to a subject.

In embodiments an effective amount administered to a subject in a day is about 5 ug to about 800 ug and every number in between, 5 ug to about 700 ug and every number in between, 5 ug to about 600 ug and every number in between, 5 ug to about 500 ug and every number in between, 5 ug to about 400 ug and every number in between, 5 ug to about 300 ug and every number in between, 5 ug to about 200 ug and every number in between, 5 ug to about 100 ug and every number in between, and 5 ug to 50 ug and every number in between.

In embodiments, effective amounts of compositions administered to a subject comprising desirable biologically active selenium-containing compounds as described herein, are preferably 200 ug or less per day or 50 ug or less per day. In embodiments, the dose may be adjusted depending on efficacy or whether any overt signs of selenium toxicosis, such as garlicky breath, hair loss, or flaky nails are observed in the subject.

In embodiments, in compositions that comprise two or more compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof, compounds are present in the composition in equal proportions. In other embodiments the ratio of one compound to another can be about 4:1 to 1:1.

In embodiments, the dose is administered at least once daily for a period of time to achieve a steady state of elemental selenium in the blood. In embodiments, the dose is administered daily for at least 60 or 90 days. In embodiments, the dose is administered while the subject is experiencing symptoms of the disease or disorder. In embodiments, the subject is at an age where the risk of mitochondrial related diseases is increased, e.g. at least 40 years of age.

The methods of the present application find use in treating (e.g., prophylactically or therapeutically) a subject (e.g., a subject with a condition associated with Alzheimer's disease, B amyloid processing, tau phosphorylation, and gene expression of presenilin 1, nicastrin, PGC1a, and phosphorylation of tau and FOXO3 and FOXO 4). Compositions comprising one or more of compounds including 5'-Methylselenoadenosine, Se-Adenosyl-L-homocysteine, Gamma-glutamyl-methylseleno-cysteine, a compound of formula (I), a compound of formula (II), a compound of formula (III), and combinations thereof can be administered to a subject (e.g., a patient) intravenously in a pharmaceutically acceptable carrier such as physiological saline. Standard methods for intracellular delivery of compounds can be used (e.g., delivery via liposome). Such methods are well known to those of ordinary skill in the art. Compositions comprising selenium are useful for intravenous administration as well as parenteral administration, such as intravenous, subcutaneous, intramuscular, and intraperitoneal.

In embodiments, a composition of the invention is formulated to cross the blood brain barrier. The compositions of the invention can be combined with an implant material suitable for delivery to the brain such as polymeric biodegradable implants such as ethylene co vinyl acetate. Other types of targeting can involve receptor mediated transport such as the insulin receptor and the transferrin receptor. These receptors can be integrated into liposomes or microspheres also including the compositions as described herein. In other embodiments, delivery to the brain can be targeted by using liposomes or PLGA spheres having an antibody, transferrin receptor, or prodrug as a targeting agent.

Accordingly, in some embodiments of the present application, compositions and/or formulations comprising selenium can be administered to a subject alone, or in combination with other forms of selenium, drugs, small molecules, or in pharmaceutical compositions where it is mixed with excipient(s) or other pharmaceutically acceptable carriers. In one embodiment of the present application, the pharmaceutically acceptable carrier is pharmaceutically inert. In another embodiment of the present application, compositions comprising selenium may be administered alone to individuals subject to, at risk of, or suffering from a disease or condition associated with B amyloid processing or tau phosphorylation. Compositions comprising 5'-Methylselenoadenosine, Se-Adenosyl-L-homocysteine, Gamma-glutamyl-methylseleno-cysteine, a compound of formula (I), a compound of formula (II), a compound of formula (III), and combinations thereof may be added to a nutritional drink or food (e.g., ENSURE, POWERBAR, or the like), a multivitamin, nutritional products, food products, etc. for daily consumption.

Glucose Metabolism

Noninsulin-dependent (Type II) diabetes mellitus (DM) is a disease characterized by insulin resistance in skeletal muscle, liver and fat, combined with defects in insulin secretion due to pancreatic β-cell function. Insulin resistance is a central feature of Type II diabetes. It is known, for example, that the vast majority of Type II diabetics are insulin-resistant. Likewise, insulin resistance in the offspring of Type II diabetics is the best predictor for later development of the disease (See, e.g., Warram et al., Ann Intern Med. 113:909 1990). Interventions that reduce insulin resistance also prevent the development of diabetes. Optimal mitochondrial function is required for normal glucose-stimulated insulin secretin from pancreatic beta cells.

Skeletal muscle and liver are the two key insulin-responsive organs in the maintenance of glucose homeostasis. The transition of these organs to an insulin-resistant state accounts for most of the changes in glucose metabolism seen in patients with Type II diabetes (See, e.g., Lowell and Shulman, Science 21:307 2005). Of these two organs, skeletal muscle is the more important in terms of consequences accruing from insulin resistance development. This is because skeletal muscle has been found to dispose of or metabolize 80 to 90% of daily ingested glucose (See, e.g., DeFronzo et al., 1985).

It has been documented by genome wide expression analysis that mitochondrial oxidative phosphorylation (OXPHOS) genes exhibit reduced expression in pre-diabetic and diabetic individuals when compared to healthy controls and that these genes are, in many cases, targets of the transcriptional coactivator proliferator-activated receptor gamma coactivator 1-alpha (PGC1-α, See, e.g., Mootha et al., 2003). In these studies, the typical decrease in expression for OXPHOS genes was modest (approximately 20%) but extremely consistent, with 89% of the genes studied showing lower expression in individuals with either impaired glucose tolerance or Type II diabetes relative to those with normal glucose tolerance.

It is generally understood and appreciated in the art that drugs or agents that boost OXPHOS activity in muscle exist as valuable therapeutics for type 2 diabetes. To bolster this hypothesis, it has long been known that aerobic exercise is the best non-pharmacological intervention for treating diabetes as it increases mitochondrial activity and number and promotes OXPHOS gene expression.

In liver, FOXO in its activated or unphosphorylated state resides in the nucleus where it binds to the promoter region for glucose 6-phosphatase and, together with other factors such as PGC-1a, increases transcription of glucose-6-phosphatase, thereby increasing the rate of glucose production. Glucose 6-phosphatase catalyzes the last step in gluconeogenesis and glycogenolysis causing the release of glucose from the liver. It is, therefore, important in the control of glucose homeostasis, particularly in diabetic subjects.

Normally, the process of FOXO phosphorylation is controlled directly by another kinase enzyme called AKT (Protein Kinase B). AKT phosphorylates FOXO and drives it from the nucleus, thereby decreasing glucose production via a decreased rate of transcription of glucose 6-phosphatase. AKT itself is under upstream control by a mini molecular cascade reaction, which starts with insulin binding to its receptor at the cell surface. This initiates a series of events involving two other kinase enzymes, Phosphatidylinositol 3-kinase (PI3K) and Phosphoinositide-dependent protein kinase 1 (PDK1). The overall pathway is known as the Insulin/PI3K/PDK1/Akt pathway and it has the job controlling glucose homeostasis via insulin signaling. In the context of FOXO control, PDK1 phosphorylates and activates Akt which, in turn, phosphorylates and inactivates FOXO.

In embodiments, a method or use is provided for increasing FOXO 3 and/FOXO 4 phosphorylation in a one or more liver cells comprising administering a composition comprising at least three compounds selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof.

In embodiments, a method of modulating glucose metabolism in one or more cells selected from the group consisting of liver cells, skeletal muscle cells, and combinations thereof comprises: administering an effective amount of a composition to the one or more cells the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount alters glucose metabolism in a liver or muscle cell as compared to cells not treated with the composition. In embodiments, the composition may exclude one or more of H (5'-Methylthioadenosine)), I (S-Adenosyl-L-homocysteine), and/or J (Gamma-glutamyl-methyl-cysteine).

In embodiments of the present application, a use is provided for a composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) for modulating glucose metabolism in a liver or muscle cell In embodiments, a method of treating type II diabetes comprises: administering an effective amount of a composition to a subject, the composition comprising at least three different compounds selected from the group consisting of: 5'-Methylselenoadenosine, Se-Adenosyl-L-homocysteine, Gamma-glutamyl-methylseleno-cysteine, a compound of formula (I), and a compound of formula (III), wherein the effective amount alters glucose metabolism in a liver or muscle cell as compared to cells not treated with the composition. In embodiments, the composition may exclude one or more of H (5'-Methylthioadenosine)), I (S-Adenosyl-L-homocysteine), and/or J (Gamma-glutamyl-methyl-cysteine).

In embodiments of the present application, a use is provided for a composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) for treating diabetes in a subject.

In embodiments, a method or use is provided for inhibiting expression of G6pc in one or more liver cells comprising: administering a composition comprising at least three compounds selected from the group consisting of 5'-Methylselenoadenosine, Se-Adenosyl-L-homocysteine, Gamma-glutamyl-methylseleno-cysteine, a compound of formula I, a compound of formula II, a compound of Formula III, and combinations thereof. In embodiments, the composition may exclude one or more of H (5'-Methylthioadenosine)), I (S-Adenosyl-L-homocysteine), and/or J (Gamma-glutamyl-methyl-cysteine).

In embodiments of the present application, a use is provided for a composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III) for inhibiting glucose-6-phophatase.

In embodiments, the increase in FOXO phosphorylation, or a decrease in G6pc ranges from an approximately 50% increase or decrease to a 500% increase or decrease, respectively, as compared to a cell of identical type not treated with the compound. The magnitude of the response depends on the cell type, the specific compound and the time in contact with the cell.

Selenium containing compounds affect gene expression in liver cells differently. In contrast to the effect compounds and compositions have on liver cells as described herein, the same or a similar composition can affect neuronal cells in an opposite way. For example, a composition as described herein, decreases the phosphorylation of FOXO3 and/or FOXO4 in neuronal cells. Expression of PGC1a is increased resulting in an increase in gluconeogenesis in neuronal cells. In contrast, the same compound or composition increases the phosphorylation of FOXO3 and/or FOXO4 in liver cells and the expression of PGC1a is not altered.

As described in the context of neuronal IMR-32 cells, PGC1a is a critical gene for MT biogenesis and carbohydrate metabolism. In liver cells, it also acts in concert with FOXO to drive the transcription of genes involved in gluconeogenesis, but cannot do this in the nuclear absence of FOXO. We examined PGC1a protein expression, and did not observe a significant change of PGC protein level in liver cells after the combination of CDE treatment by quantitative analysis. However, due to the robust effect noted on FOXO phosphorylation in response to CDE, it is almost certain that it would be excluded from the nucleus and, hence, the level of PGC1a becomes of low importance because it requires FOXO to initiate the gluconeogenic process. Together, these results suggest that the combination of CDE did not affect PI3k/PDK1/AKT signaling and several other AKT direct or indirect downstream signaling molecules, except the above described but critical FOXOs. In other words, the combination of CDE selectively inactivates FOXOs and this action appears to be independent on the PI3K/PDK1/AKT signaling in the liver cells.

In embodiments, the effective amount of compounds and compositions as described herein is an amount effective to inhibit expression of G6pc, modulate glucose metabolism, or increase FOXO phosphorylation in a liver cell without being toxic to the cells. Gene expression in liver cells can be determined using a number of assays on a sample taken from a subject treated in accord with the compositions described herein. The effective amounts selected do not show toxicity for any of the exemplified cells including kidney, mouse skeletal, human neuronal, or mouse liver cells.

As is well known in the medical arts, dosages for any one subject may depend upon many factors, including the patient's size, body surface area, age, the particular compound to be administered, sex, time and route of administration, general health, and interaction with other drugs being concurrently administered.

In embodiments, the effective amount of a selenium-containing composition of the invention to administer to a subject to inhibit expression of G6pc, modulate glucose metabolism, treat type II diabetes or increase FOXO phosphorylation in liver, or skeletal muscle cell is about 5 ug or greater or 800 ug or less per day of a single desirable biologically active selenium-containing compound of the invention or multiple desirable biologically active selenium-containing compounds of the invention. When multiple desirable biologically active selenium-containing compounds are present, the effective amount of the composition to be administered to a subject is the total amount for all desirable biologically active selenium-containing compounds in the composition.

In embodiments an effective amount to administer to a subject of a desirable biologically active selenium-containing compound of the invention is about 5 ug to about 800 ug and every number in between, 5 ug to about 700 ug and every number in between, 5 ug to about 600 ug and every number in between, 5 ug to about 500 ug and every number in between, 5 ug to about 400 ug and every number in between, 5 ug to about 300 ug and every number in between, 5 ug to about 200 ug and every number in between, 5 ug to about 100 ug and every number in between, and 5 ug to 50 ug.

In embodiments of the invention, compositions comprising compounds as described herein, are preferably administered at 200 ug or less per day or 50 ug or less per day. In embodiments of the invention, the dose may be adjusted depending on efficacy or whether any overt signs of selenium toxicosis, such as garlicky breath, hair loss, or flaky nails are observed in the subject.

In embodiments, in compositions that comprise two or more compounds selected from the group consisting of 5'-Methylselenoadenosine, Se-Adenosyl-L-homocysteine, Gamma-glutamyl-methylseleno-cysteine, a compound of formula (I), a compound of formula (II), a compound of formula (III), and combinations thereof, the compounds are present in the composition in equal proportions. In other embodiments the ratio of one compound to another can be about 4:1 to 1:1.

In embodiments, the dose is administered at least once daily for a period of time to achieve a steady state of elemental selenium in the blood. In embodiments, the dose is administered daily for at least 60 or 90 days. In embodiments, the dose is administered while the subject is experiencing symptoms of the disease or disorder. In embodiments, the subject is at an age where the risk of mitochondrial related diseases is increased, e.g. at least 40 years of age.

In other embodiments, delivery to the liver can be targeted by using liposomes or PLGA spheres having an antibody, by preparing a selenoglycoside, or a prodrug targeted to the liver.

Other Embodiments of the Present Application

In some embodiments, a composition is provided consisting essentially of or consisting of a compound according to formula (I):

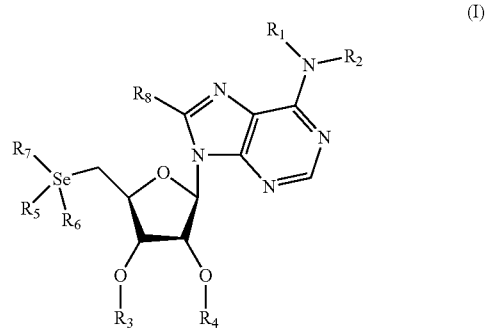

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_7$ is H, alkyl, alkenyl, alkynyl, ketone, amino alcohol, amino acid, OR', Se—R', S—R', where R' is selected from H, alkyl, cycloalkyl, aryl, aralkyl, or heterocyclyl; and $R_8$ is hydrogen, azido, alkyl, alkenyl, alkynyl.

In further embodiments, one or more of these compounds of Formula (I) can be isolated and/or purified.

In some embodiments, a composition is provided consisting essentially of or consisting of a compound according to formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', or C(O)OR', where R' is selected from alkyl, cycloalkyl, aryl, aralkyl, or heterocyclyl; $R_5$ and $R_6$ are each absent; and $R_7$ is alkyl, or amino acid.

In some embodiments, a composition is provided consisting essentially of or consisting of a compound according to formula (I), or a pharmaceutically acceptable salt, hydrate, or prodrug thereof, wherein $R_1$, $R_3$, $R_4$ and $R_8$ are each H; $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; $R_5$ and $R_6$ are each absent; and $R_7$ is alkyl, or amino acid; with the proviso that 5'-selenoadenosyl methionine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In a specific aspect, a composition is provided consisting essentially of or consisting of a compound, or a pharmaceutically acceptable salt, hydrate, or prodrug thereof, according to formula (I) that is 5'-methylselenoadenosine ("compound C").

In some embodiments, compositions consist essentially of or consist of a compound according to formula (I), or a pharmaceutically acceptable salt, hydrate, or prodrug thereof, with the proviso that 5'-selenoadenosyl methionine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se(methyl)-selenoxide, adenosyl-hydroxy selenoxide, ethyl selenoadenosine, seleno-(hydroxy)-selenophene-(3'-desoxy-adenosine), adenosyl-hydroxy selnoxide, and seleno-adenosyl-Se(methyl)-selenoxide may each be excluded from the composition.

In some embodiments, a composition is provided consisting essentially of or consisting of a compound according to formula (II):

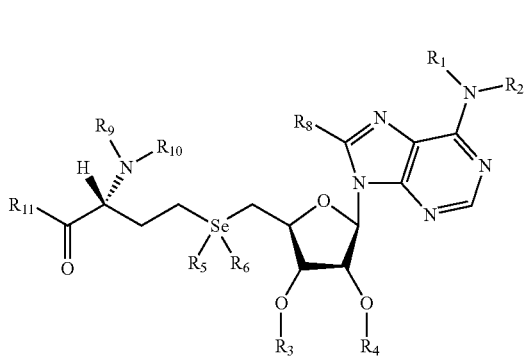

(II)

or a pharmaceutically acceptable salt, hydrate, or prodrug thereof,
wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_8$ is hydrogen, azido, alkyl, alkenyl, alkynyl;

$R_9$ is H, acyl, alkyl, alkenyl, alkynyl, aralkyl, carboxyl, cycloalkyl, C(O)R', C(O)OR', where R' is alkyl, cycloalkyl, aryl, aralkyl, or heterocyclyl; or $R_9$ together with $R_{10}$ form a heterocyclic ring having 4 to 8 ring members with at least one heteroatom selected from oxygen or nitrogen;

$R_{10}$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_9$ together with $R_{10}$ form a heterocyclic ring having 4 to 8 ring members with at least one heteroatom selected from oxygen or nitrogen; and $R_{11}$ is OH, OR, alkoxy, aralkoxy, or amino, where R is selected from alkyl, cycloalkyl, aryl, aralkyl, heterocyclyl, or a pharmaceutically acceptable salt, or inner salt.

In further embodiments, one or more of these compounds of Formula (II) can be isolated and/or purified.

In some embodiments, a composition is provided consisting essentially of or consisting of a compound according to formula (II), or a pharmaceutically acceptable salt, hydrate, or prodrug thereof, wherein $R_1$, $R_3$, $R_4$, $R_8$ and $R_9$ are each H; $R_2$ is H, acyl, alkyl, carboxyl, C(O)R', or C(O)OR', where R' is selected from alkyl, cycloalkyl, aryl, aralkyl, or heterocyclyl; $R_5$ and $R_6$ are absent; $R_{10}$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; and $R_{11}$ is OH, OR, alkoxy, aralkoxy, or amino, where R is selected from alkyl, cycloalkyl, aryl, aralkyl, heterocyclyl, or a pharmaceutically acceptable salt, or inner salt.

In some embodiments, a composition is provided consisting essentially of or consisting of a compound according to formula (II), or a pharmaceutically acceptable salt, hydrate, or prodrug thereof, wherein $R_1$, $R_2$, $R_3$, $R_4$, $R_5$, $R_6$, $R_7$, $R_8$, $R_9$, $R_{10}$ are as defined above and wherein $R_{11}$ is OH or, where R is selected from methyl, ethyl, propyl, isopropyl, butyl, sec-butyl, or tert-butyl.

In a specific aspect, a composition is provided consisting essentially of or consisting of a compound according to formula (II), or a pharmaceutically acceptable salt, hydrate, or prodrug thereof, that is 5'-selenoadenosyl homocysteine (compound "D"), or a pharmaceutically acceptable salt, hydrate, or prodrug thereof.

In some embodiments, compositions consist essentially of or consist of a compound according to formula (II), or a pharmaceutically acceptable salt, hydrate, or prodrug thereof; with the proviso that 5'-selenoadenosyl methionine, allylselenoadenosyl homocysteine, seleno-adenosyl homocysteine, and seleno-hydroxy adenosyl homocysteine may each be excluded from the composition.

In some embodiments, a composition is provided consisting essentially of or consisting of a compound according to formula (III):

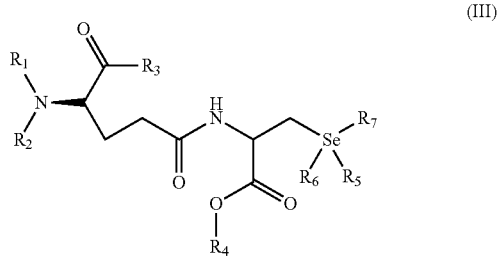

(III)

or a pharmaceutically acceptable salt, hydrate, or prodrug thereof, wherein
$R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;
$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;
$R_3$ is OH, OR, alkoxy, aralkoxy, or amino, where R is selected from alkyl, cycloalkyl, aryl, aralkyl, heterocyclyl, or a pharmaceutically acceptable salt, or inner salt;
$R_4$ is H, alkyl, alkenyl, alkynyl, cycloalkyl, aryl, aralkyl, heterocyclyl, or a pharmaceutically acceptable salt, or inner salt;
$R_5$ is oxo, hydroxyl, alkyl, alkenyl, alkynyl, OR', or is absent; where R' is selected from alkyl, alkenyl, alkynyl, cycloalkyl, aryl, or aralkyl;
$R_6$ is oxo, hydroxyl, alkyl, alkenyl, alkynyl, OR', or is absent; where R' is selected from alkyl, alkenyl, alkynyl, cycloalkyl, aryl, or aralkyl; and
$R_7$ is H, alkyl, alkenyl, alkynyl, ketone, OR', Se—R', S—R', where R' is selected from H, alkyl, cycloalkyl, aryl, aralkyl, or heterocyclyl.

In some embodiments, a composition is provided consisting essentially of or consisting of a compound according to formula (III), or a pharmaceutically acceptable salt, hydrate, or prodrug thereof, wherein
$R_1$ and $R_2$ are each H;
$R_3$ is OH, OR, alkoxy, aralkoxy, or amino, where R is selected from alkyl, cycloalkyl, aryl, aralkyl, heterocyclyl, or a pharmaceutically acceptable salt, or inner salt;
$R_4$ is H, or a pharmaceutically acceptable salt, or inner salt;
$R_5$ and $R_6$ are absent; and
$R_2$ is alkyl, alkenyl or alkynyl.

In further embodiments, one or more of these compounds of Formula (III) can be isolated and/or purified.

In some embodiments, a composition is provided consisting essentially of or consisting of a compound according to formula (III), or a pharmaceutically acceptable salt, hydrate, or prodrug thereof, wherein $R_1$ and $R_2$ are each H; $R_3$ is OH or, where R is selected from methyl, ethyl, propyl, isopropyl, butyl, sec-butyl, or tert-butyl; $R_4$ is H; $R_5$ and $R_6$ are absent; and $R_7$ is alkyl that is methyl, ethyl, propyl, isopropyl, butyl, iso-butyl, sec-butyl, or tert-butyl.

In some embodiments, a composition is provided consisting essentially or consisting of a compound according to formula III, or a pharmaceutically acceptable salt, hydrate, or prodrug thereof, wherein $R_1$ and $R_2$ are each H; $R_3$ is OH or, where R is selected from methyl, ethyl, propyl, isopropyl, butyl, sec-butyl, or tert-butyl; $R_4$ is H; $R_5$ and $R_6$ are absent; and $R_7$ is methyl.

In a specific aspect, a composition is provided consisting essentially of or consisting of a compound according to formula (III), or a pharmaceutically acceptable salt, hydrate, or prodrug thereof, that is gamma-glutamyl-methylselenocysteine ("compound E"), or a pharmaceutically acceptable salt, hydrate, or prodrug thereof.

In some embodiments, a composition consisting essentially of or consisting of a compound according to formula (III), or a pharmaceutically acceptable salt, hydrate, or prodrug thereof, with the proviso that γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, and selenoglutathione-γ-glutamoylcysteine may each be excluded from the composition.

In some embodiments, a composition is provided consisting essentially of or consisting of one or more compounds according to one or more of formulas (I), (II) and/or (III), wherein each of the following compounds is excluded from the composition in order to minimize selenium toxicity, remove inactive or inhibitory compounds, and/or maximize the therapeutic index of the composition, wherein the excluded compounds are γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, γ-glutamoyl selenocysteine-γ-glutamoyl cysteine, γ-glutamoylcysteine-2,3-DHP-selenocysteine, di-γ-glutamoylselenocysteine, selenoglutathione-γ-glutamoylcysteine, dehydroxy 5'-methylselenoadenosine, ethylselenoadenosine, seleno(hydroxyl)-selenophene-(3'-deoxy-adenosine), allylselenoadenosyl homocysteine, seleno-adenosyl homocysteine, seleno-hydroxy adenosyl homocysteine, seleno adenosine, seleno-adenosyl-Se (methyl)-selenoxide, adenosyl-hydroxy selenoxide, ethyl selenoadenosine, seleno-(hydroxy)-selenophene-(3'-desoxy-adenosine), adenosyl-hydroxy selenoxide, and seleno-adenosyl-Se(methyl)-selenoxide.

In embodiments, any of the compounds described herein can be modified to prolong half-life, to protect the compound against oxidation, to target the compound to a tissue, to allow the compound to pass the blood brain barrier as described herein.

In some embodiments, a composition is provided consisting essentially of or consisting of one or more compounds each according to formula (I). In some aspects, the composition comprising one or more compounds each according to formula (I) comprises 5'-methylselenoadenosine, or a pharmaceutically acceptable salt, hydrate, or prodrug thereof; and 5'-selenoadenosyl homocysteine, or a pharmaceutically acceptable salt, hydrate, or prodrug thereof.

In some embodiments, a composition is provided consisting essentially of or consisting of one or more compounds each according to formula (I) and formula (III). In some aspects, the composition comprising one or more compounds each according to formula (I) and formula (III) comprises 5'-methylselenoadenosine, or a pharmaceutically acceptable salt, hydrate, or prodrug thereof; 5'-selenoadenosyl homocysteine, or a pharmaceutically acceptable salt, hydrate, or prodrug thereof; and gamma-glutamyl-methylseleno-cysteine, or a pharmaceutically acceptable salt, hydrate, or prodrug thereof.

In some embodiments, the composition consisting essentially of or consisting of one or more compounds each according to formula (I) and formula (III) comprises 5'-methylselenoadenosine, or a pharmaceutically acceptable salt, hydrate, or prodrug thereof; and gamma-glutamyl-methylseleno-cysteine, or a pharmaceutically acceptable salt, hydrate, or prodrug thereof.

In some embodiments, a composition is provided consisting essentially of or consisting of one or more compounds each according to formula (II) and formula (III). In some aspects, the composition comprising one or more compounds each according to formula (II) and formula (III) comprises 5'-selenoadenosyl homocysteine, or a pharmaceutically acceptable salt, hydrate, or prodrug thereof; and gamma-glutamyl-methylseleno-cysteine, or a pharmaceutically acceptable salt, hydrate, or prodrug thereof.

According to another aspect, the present invention provides a pharmaceutical composition, which consists essentially of or consists of a therapeutically-effective amount of one or more compounds of the present invention or a pharmaceutically-acceptable salt, ester or prodrug thereof, together with a pharmaceutically-acceptable diluent or carrier. Pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions may be formulated for any route of administration as described herein.

Example 1

Synthesis and Characterization of 5'-Methylselenoadenosine ("C")

The synthesis scheme and methodology was:

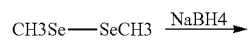

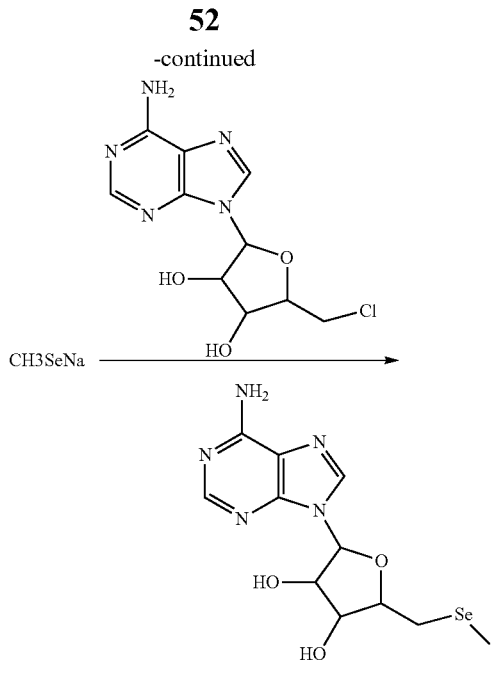

Place sodium borohydride (227 mg, 6.0 mM, under Ar°) in a 200 mL round-bottom flask containing 20 mL of anhydrous ethyl alcohol, equipped in a magnetic stirrer and located in an ice cooling bath. Add from a syringe dimethyldiselenide (190 uL, 376 mg, 2.0 mM), with cooling, stirring and under Ar flow. After discoloration of a yellowish solution add solid 5'-chloro-5'-deoxyadenosine (1,143 g, 4.0 mM). The 5-Cl-Ade is very poorly soluble in ethyl alcohol. 100 mL more ethyl alcohol was added to dissolve the precipitate. Stirring of the mixture at r.t. was continued for the following four days. MS was used to monitor the conversion. ~75% conversion accomplished after 5 days. The solvents were evaporated and the product 3.22 g (with ~20% of SM) was collected and purified by the reverse phase (C-8) preparative chromatography to yield 1.1 g of pure product which molecular weight was confirmed by mass spectrometry.

Example 2

Synthesis and Characterization of Se-Adenosyl-L-Homocysteine ("D")

The synthesis scheme and methodology was:

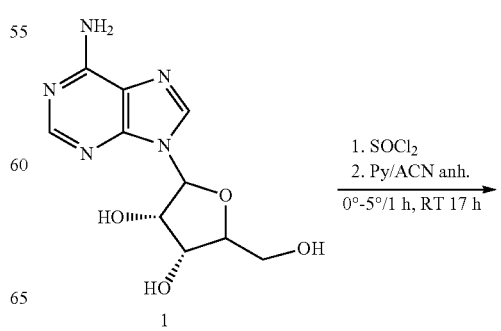

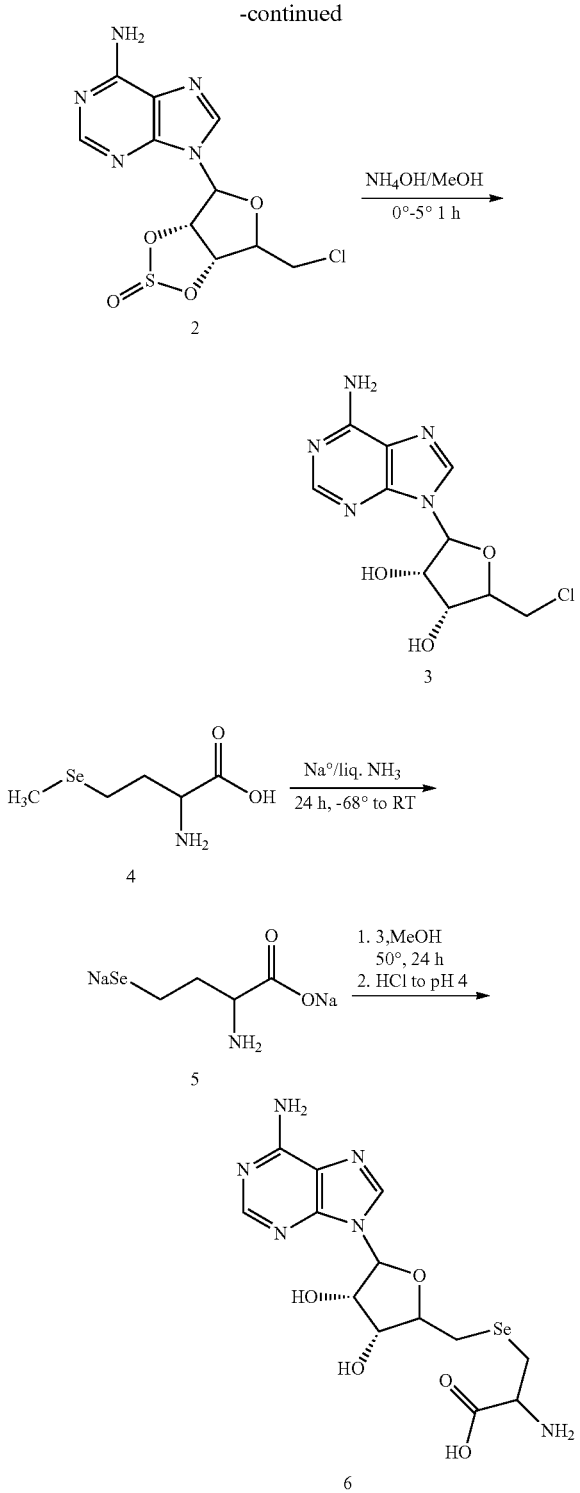

5'-Chloro-5'-deoxyadenosine (639-62)

Place 89 G (0.366 mole, 1 eq.) adenosine, 59.3 ML (58 G, 1.833 mole, 2 eq.) anhydrous pyridine and 1 L anhydrous acetonitrile in an oven dried, 2 L, 4 neck flask, equipped in a dropping funnel, a stirrer, gas inlet/outlet and a thermometer. The reaction set is placed in an ice/salt bath. Initiate agitation and when the temperature of the solution drops below 3° C. start a very slow addition of thionyl chloride (strong exotherm!). The temperature of the reaction mixture needs to be maintained below 5° C. during thionyl chloride addition and for 4 h more (at this time the solution is yellow with white-yellow precipitate on the bottom. Then the reaction is left overnight at ambient temperature. The next morning the voluminous precipitate is filtered off using sintered glass filter and washed on the filter with three 100 ML volumes of dry acetonitrile during which the precipitate color changes into white. The wet precipitate is then transferred back into the 2 L reaction flask, containing a mixture of 800 ML of methanol and 160 ML of water into which, 80 ML of concentrated ammonium hydroxide solution is added drop-by-drop with mechanical stirring and cooling with water bath. The mixture is agitated for 45 min at ambient temperature and a white precipitate that is formed is separated from the liquid by vacuum filtration. The filtrate is concentrated to dryness using vacuum rotary-evaporator, while the precipitate is crystallized from ~560 ML hot water, cooled in an ice-water bath, and the first crop of the crystals is filtered off and freeze-dried.

Then this filtrate is used as a solvent in the crystallization of solids resulted from the rotary evaporation of the first filtrate to obtain second crop of the product which is also freeze-dried (2 days). Both crops of crystals are finally dried for two days over phosphorous pentoxide in a vacuum dessicator. 84 G of white crystals, 80.5% yield are obtained. MS (286-M+H), mp. 187° C.

Selenoadenosylhomocysteine (655-40)

9.806 G (50 mM, 1 eq.) of L-selenomethionine are charged into a 2 L, three neck flask equipped in a thermometer, a large cooling finger (with bubble-meter at the outlet), ammonia gas inlet (reaching bottom of the flask) and a magnetic stirring bar and placed in a 2.5 L duar vessel containing $CO_2$-Aceton cooling bath. $Ar^o$ is passed through the flask before adding solid $CO_2$ to acetone bath and the cooling finger. When the temperature inside the flask drops below −35° C. the flow of anhydrous ammonia (gas) is started and when liquid ammonia level reaches the volume of 800 ML the gas flow is stopped. At this time small pieces of metallic sodium are added to a well stirred solution until blue-violet coloration of the solution persists for ~30 sec. Total of 2.645 G (115 mM, 2.3 eq.) of sodium are added within 45 min. Agitation and cooling is maintained for 30 min more. At this time all of the components are in the solution. 14.856 G (52 mM, 1.04 eq.) of anhydrous 5'-chloro-5'-deoxyadenosine are added in a single portion and the reaction mixture is left with stirring and very slow $Ar^o$ flow overnight. The next morning (if all of ammonia is gone) 350 ML of anhydrous methanol are added to the white solids which are present in the flask. The flask is placed in an oil bath, a reflux condenser is installed, $Ar^o$ gas flow is maintained and an oil bath is heated to 50° C. for the subsequent 24 h. At this time 1 ML of the solution is acidified to pH 3.5 with few drops of 0.1N HCl and the sample is analyzed for the presence of substrates using mass spectrometry. If they are below 5% the mixture can be acidified with 1N HCl to pH 3.5, filtered from salts, concentrated to dryness using vacuum rotary-evaporator and the crude product can be purified by crystallization from water-ethanol mixture. 15.98 G (74% yield) of the first crop of Selenoadenosylhomocysteine crystals is ~95% clean, and can be used in biological studies without further purification.

Example 3

Synthesis and Characterization of Gamma-Glutamyl-Methylseleno-Cysteine

The synthesis scheme and methodology was:

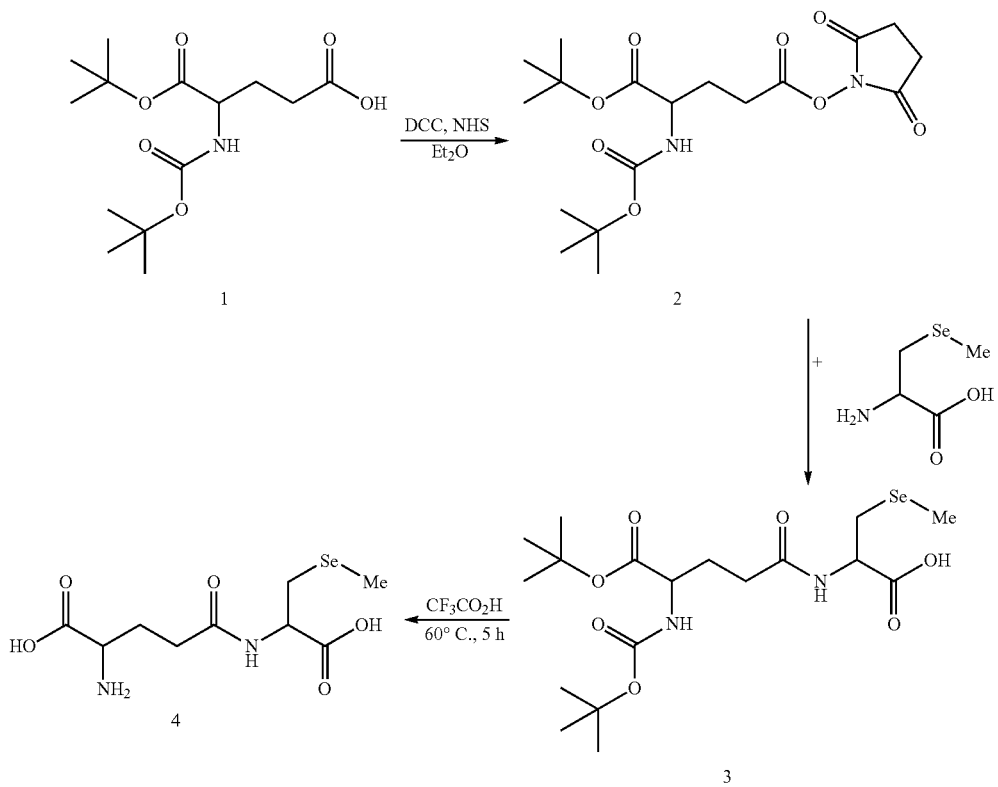

Synthesis of N-Boc-(O-tBu)-L-Glu-OSu (655-90)

N-Boc-(O-tBu)-L-Glu-OH (303 mg, 1.0 Mmol), N-hydroxysuccinimide (121 mg, 1.05 Mmol) and dicyclohexyl carbodiimide (227 mg, 1.1 Mmol) were suspended/dissolved in 15 mL of anhydrous ethyl ether and 10 uL of dimethylethylbenzylamine was added from a syringe into the reaction mixture. Stirring at ambient temperature (22° C.) was maintained for 48 h. The mixture was filtered and the precipitate was washed 10×10 mL of ethyl ether. The filtrate was concentrated and dried under high vacuum yielding white crystalline product (570 mg, ~90% yield). MS (M+Na$^+$)=423.17;

Synthesis of N-Boc-(O-tBu)-L-Glu-MeSe-Cys-OH (655-90)

N-Boc-(O-tBu)-L-Glu-OSu (570 mg, 0.9 Mmol), methylselenocysteine (175 mg, 0.8 Mmol), triethylamine (152 mg, 209 µL, 1.5 Mmol) were added into a mixture of 6 mL of 1,4-Dioxane and 2 mL of water. Magnetic stirring of the reaction mixture was maintained for 100 h. After this time 1.21N HCl (1.65 mL) were added and the post-reaction mixture was extracted with 3×20 mL of ethyl ether and the extract was concentrated to dryness using vacuum rotary-evaporator yielding 649 mg of waxy product that was submitted to preparative HPLC. 283 mg of the product were collected (75.6% Yield). The mass spectrum confirmed the molecular weight of the product and the presence of a single Se atom in it. Calcd. Ms for $C_{18}H_{32}N_2O_7Se$=468.42. Found 469.24 m/e (M+H$^+$) and 491.24 m/e (M+Na$^+$).

Synthesis of Gamma-Glutamyl-Methylseleno-Cysteine (655-92)

A mixture of 283 mg (0.6 Mmol) of N-Boc-(O-tBu)-L-Glu-MeSe-Cys-OH, 2 mL of thioanisol and 5 mL of trifluoroacetic acid were heated with magnetic stirring in an oil bath, for 6 h and at 63° C. and left over night at ambient temperature (22° C.). After this time the reaction mixture was added (drop-by-drop) into vigorously stirred ethyl ether (20 mL). The precipitate that formed was washed with 2×20 mL of ethyl ether yielding 138.3 mg of creamy precipitate which was then purified by preparative HPLC.

Example 4

Three synthetic selenoorganic compounds were tested alone or in combination in cell culture for effects on mitochondrial function, cell survival and gene expression. Cells tested included liver cells, kidney cells, neuronal cells and skeletal muscle.

Materials and Methods

Cell Lines and AT Compounds

Human embryonic kidney HEK293T cells were generously provided by Dr. Qiutang Li (University of Louisville). The mouse skeletal muscle myoblast C2C12 cell line was a gift from Dr. Xiao (University of Kentucky). Human neuroblast IMR-32 cells and mouse liver cell line AML-12 were purchased from American Type Culture Collection (ATCC, Manassas, Va.). All these cells were amplified in the ATCC recommended culture media.

Compound C (5'-Methylselenoadenosine), D (Se-Adenosyl-L-homocysteine)), and E (Gamma-glutamyl-methyl-seleno-cysteine)), and their sulfur analogs H (5'-Methylthioadenosine)), I (S-Adenosyl-L-homocysteine), and J (Gamma-glutamyl-methyl-cysteine) were identified as individual compounds of selenized yeast having less than 2% inorganic selenium and were either synthesized or obtained (where available) from commercial sources. The purities of all tested compounds were verified to be >99%, as determined by Mass-Spectrometry.

Fluorescence Analysis of Mitochondrial Potential in HEK293T Cells

HEK293T cells were cultured in 8-chamber glass slides ($1 \times 10^4$ cells/chamber) for 24 hours, and then treated with various concentrations of compounds or its respective sulfur analogs (dissolved in sterilized water) for 4.5 hr. These compound-treated cells were rinsed twice with PBS, and incubated with Mitotracker Orange Fluorescence Dye (Invitrogen) at 37° C. for 30 min, and then replaced with fresh PBS according to the Manufacturer's protocol. Then fluorescent signals (mitochondrial potential) in these living cells were recorded using a Zeiss Axio Vert.A1 fluorescence microscope (Thornwood, N.Y.). At least three samples in each treatment group were analyzed under the fluorescent microscope.

Quantitative Analysis of Mitochondrial Potential in C2C12, IMR-32 and AML-12 Cells For C2C12 cells, equal number of cells ($1 \times 10^4$) were seeded on Corning 96-well clear-bottom and dark-wall cell culture plates (VWR), cultured in 10% FBS DMEM media for 24 hr., and then treated with vehicle (sterilized water), compound C and D and their sulfur analogs for 24 and 48 hrs. These vehicle- or compound-treated cells were rinsed twice with PBS, incubated with Mitotracker Orange fluorescence dye at 37° C. for 30 min, and then replaced with PBS. Mitotracker Orange fluorescence intensities (mitochondrial potential) in these living cells were determined by a Bio-TeK Synergy HT Multi-Mode Fluorescence Microplate Reader (Winooski, Vt.). Eight samples per each treatment were examined for the above analysis, and data are presented as mean±sem of eight samples.

For AML-12 liver cells, cells were amplified in 10% FBS Dulbecco's modified Eagle's medium and Ham's F12 medium (1:1) (DMEM/F12) media supplemented with 1× Insulin/Transferin/Selenium (ITS, Sigma). Then equal number of cells ($1 \times 10^4$ cells/well) were seeded on Corning 96-well clear-bottom and dark-wall cell culture plates (VWR, Radnor, Pa.), cultured in ITS-free 10% FBS DMEM/F12 media for 24 hr., and then subjected to the treatments of various compounds or combination of compounds for 6, 24, and 48 hr. Mitochondrial potential in living cells was determined by quantitative analysis of fluorescence intensities using the Mitotracker orange dye as described above. In addition, the above treated cells were also incubated with Hoechst 33342 dye (Invitrogen, Grand Island, N.Y.) to stain cell nuclei according to the Manufacturer's protocol. The fluorescent intensities of stained cell nuclei by Hoechst 33342 dye were also determined by the fluorescence microplate reader. The mitochondrial potential per cell in living cells was obtained by normalizing the fluorescence intensities of Mitotracker orange dye to the fluorescence intensities of Hoechst 33342 dye in each well. Eight samples per each treatment were examined for the above analysis and data are presented as mean±sem of eight samples.

Similar to the above studies on AML-12 cells, the mitochondrial potential per cell in living IMR-32 cells was determined using the Bio-TeK Synergy HT Multi-Mode fluorescence microplate reader with the following modifications. To improve the attachment of IMR-32 cells to culture dishes, cell culture plates were precoated with 0.1% gelatin (Sigma, St. Louis, Mo.). $2 \times 10^4$ cells per a 96-well were seeded on gelatinized 96-well plates for the above studies. To reduce the cell dislodgment, Mitotracker orange and Hoechst 33342 fluorescent dyes (diluted in culture media) were directly added to each well after vehicle- or compound-treatments. After dye incubation, cell culture media were carefully replaced with 1× PBS for the quantitation analysis of fluorescence on the microplate reader. Eight samples per each treatment were examined for the above analysis, and the experiments were repeated at least five times. Data are presented as mean±sem of eight samples.

Cell Viability Assay

Cell viability in cultured cells was determined using Promega's CellTiter96® AQueous One Solution Cell Proliferation Assay kits, according to the Manufacturer's protocol. In brief, equal number of C2C12 ($1 \times 10^4$ cells/well), AML-12 ($1 \times 10^4$ cells/well) and IMR-32 ($2 \times 10^4$ cells/well) were seeded on 96-well clear plates (VWR) and treated with vehicle or compounds for 24, 28 and/or 72 hr. Then, cultured cells were incubated with AQueous One solution (100 ul/per well) at 37° C. for 1 hr, and the absorbance of OD490 nm in each sample was determined by the Bio-Tek microplate reader. Cell viability in culture cells were determined by the subtraction of OD490 nm in cultured cells with the OD490 nm in plain culture media (without seeding of cells). Eight samples per each treatment were examined for the above analysis. Data are presented as Mean±sem of eight samples.

RNA Isolation and Real-Time PCR Analysis

Human IMR-32 cells were seeded on gelatinized 6-well ($6.5 \times 10^5$ cells/well) or 24-well ($1.3 \times 10^5$ cells/well) plates, while mouse liver AML-12 cells were cultured on uncoated 6-well ($3.33 \times 10^5$ cells/well) or 24-well ($6.7 \times 10^4$ cells/well) plates. Cells were treated with vehicle (control) or various compounds for 6, 24 or 48 hr. Total RNA from these cells was using Trizol (Invitrogen) according to the Manufacturer's protocol, and then incubated with DNase I to remove any potential contaminated genomic DNA. Then RNA samples were subjected to real-time PCR analysis using the Applied-Bioscience's RT kit and predesigned Taqman probes (Invitrogen), as described previously (Lan et al EMBO J 2003). Three to six samples were analyzed in each treatment group. Data were normalized by Actin B (Actb) or Glyceraldehyde Phosphate Dehydrogenase (Gapdh) levels in each sample, and are presented as mean±sem of 3-6 samples.

Protein Preparation and Western Blot Analysis

IMR-32 and AML12 cells were seeded on 6-well plates, and then treated with vehicle and various compounds for 6 and 24 hr, as described above. After treatments, cells were rinsed with ice-cold PBS, and lysed in the ice-cold RIPA buffer containing complete proteinase and phosphotase inhibitors (Themo-Fisher Scientific, Waltham, Mass.) on ice for 30 min. Cell lysates were collected using a cell scraper and transfer pipette, and then centrifuged at 12000 g for 30 min at 4° C. to remove the DNA pellet and obtain the protein extract. Protein levels in the supernatant of these cell lysates were determined using the Pierce Micro-BCA protein assay kit (Themo Scientific-Piece Biotechnology, Rockford, Ill.) according to the manufacturer's protocol.

For Western blot analysis, five micrograms of total proteins from vehicle- and compound(s)-treated cells were subjected to SDS-PAGE gel separation, and then transferred to PVDF membranes, as described previously (Reddy, Liu et al. 2008 Science). Membranes were blocked in a phosphate-buffered saline (PBS) containing 5% (w/v) of bovine serum albumin (Sigma, St. Louis, Mo.), and incubated with specific primary antibodies followed by the incubation with HRP-conjugated anti-mouse or anti-rabbit secondary antibodies (1:5000 dilution, Cell Signaling Inc.). All primary antibodies except G6PC (Santa Cruz), Actb (Li-COR, Lincoln, Nebr.), Elf2bε and pElf2bε (Abcam, Cambridge, Mass.) were purchased from Cell Signaling Inc. Positive signals on the membrane blots were detected using the Amersham's enhanced chemiluminescence Western Blotting Prime Detection reagents (GE healthcare Lifescience, Pittsburgh, Pa.). Images of these luminescence signals on the membrane blots were captured using the LI-COR Odyssey Fc Image system (Lincoln, Nebr.). The same membrane blot was striped and re-blotted with another antibody as described in the GE WB ECL-prime-detection protocol (GE healthcare Lifescience, Pittsburgh, Pa.). Protein band densities in the Western blots were determined using the Li-COR Image studio software or NIH ImageJ software, and then normalized by Actb level in each sample. Data are presented as mean±sem of three samples per each group.

Statistical Analysis

If applicable, a Student's t-test was performed to determine the statistical difference between two groups. P value less than 0.05 was considered significant.

Results and Discussion: Mitochondrial Function

To test if compound C or D can enhance the mitochondrial ("MT") potential in cultured human kidney cells, HEK293T cells were treated with 37.5 and 75 ppb of compound C or D. These amounts were based on work with the SeaHorse assay where the effective dose was found to be 100-150 ppb. Compound C as well as its sulfur analog H were incubated with HEK293T cells for 4.5 hour (hr), and subjected to fluorescent analysis under the microscope. As shown in FIG. 1, compound C at the lower dose (37.5 ppb) enhanced MT potential while there were less effects on MT potential in kidney cells treated with a higher dose (75 ppb) of compound C for 4.5 hr. In contrast, compound D at all tested doses did not affect MT potential (FIG. 1).

Our results clearly demonstrate that compound C enhanced MT potential in kidney cells while compound D was ineffective. Considering that selenium is present in both compound C and D and that their sulfur analogs, H and J, respectively, proved incapable of stimulating mitochondrial activity, one must conclude that the stimulatory effect of compound C in kidney cells is due to a combined effect of selenium and the molecular structure surrounding selenium in this organoselenium compound. The stimulatory activity is not due to a selenium effect alone.

The importance of being able to increase mitochondrial activity in kidney cells may have very significant health benefits, especially in diabetic subjects. Very recent research (Sharma et al., JAM Soc Nephrol, 2013: 1901-12) concluded from a metabolomic analysis of urine from a diabetic population that diabetic kidney disease is clearly linked to a decrease in mitochondrial function. Diabetic kidney disease (DKD) is the leading cause of end-stage renal disease and the authors concluded that therapeutic approaches that restore or increase mitochondrial function could ameliorate or even arrest DKD. Of added interest is the fact that the authors link mitochondrial dysfunction in these cases to a decrease in the expression of a transcriptional co-activator called PGC1a. As discussed later, PGC1a is a target of the synthetic selenium compounds described in this application.

Mitochondrial Potential Enhanced by Compound C and D in Mouse C2C12 Cells

Figure 2:
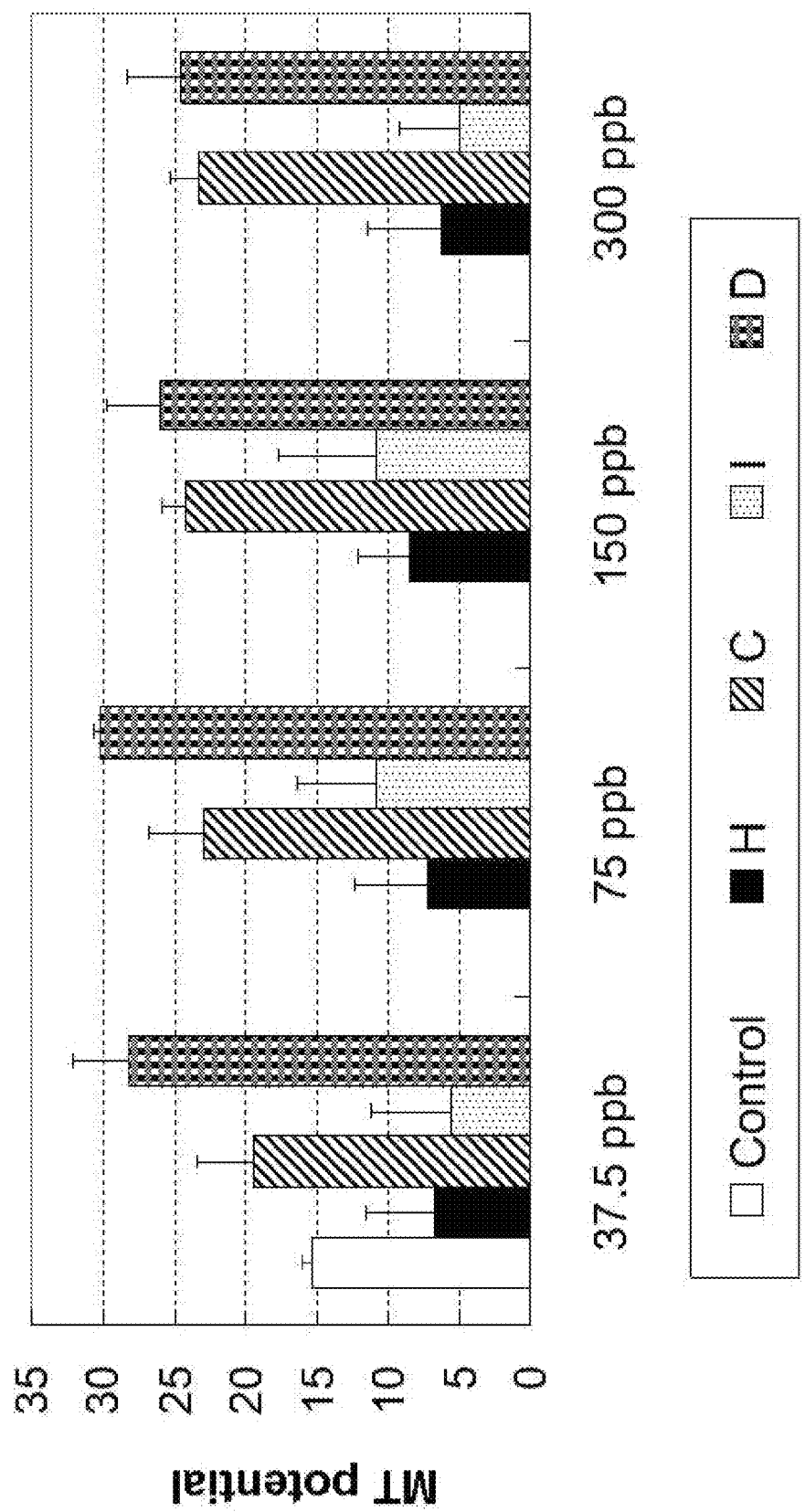
FIG. 2 shows enhanced mitochondrial ("MT") potential in skeletal muscle C2C12 cells upon treatment with compounds C (5'-Methylselenoadenosine) and D (Se-Adenosyl-L-homocysteine). The sulfur analogs H (5'-Methylthioadenosine) and I (S-Adenosyl-L-homocysteine) decreased mitochondrial potential at all concentrations.

To test whether compound C and D affect MT potential in skeletal muscle cells, C2C12 cells were treated with vehicle (water, control) or various concentrations of selenium and sulfur compounds, and then subjected to quantitative analysis of MT potentials. As shown in FIG. 2, MT potential was decreased in C2C12 cells after treatment with sulfur analogs for 24 hr (when compared to control), indicating that sulfur compounds displayed some MT toxicity in skeletal muscle cells. In contrast, selenium compounds C and D significantly enhanced MT potential (FIG. 2).

Two aspects of this result are particularly surprising and unanticipated. Firstly, compound D, while inactive in kidney cells was highly effective in stimulating mitochondrial activity in muscle cells (some two-fold over control levels at its most effective dose). Moreover, at lower doses (37.5 and 75 ppb, FIG. 2), it proved more potent than compound C which (as shown above) was the only effective tested compound in kidney cells.

Secondly, the sulfur analogs of C and D, rather than just having no effect, relative to vehicle-treated control cells, were inhibitory to mitochondrial activity (reducing it by ⅔ in some cases). This effect has not been reported in the past but may help explain why some studies using selenium enriched yeast preparations have reported pro-diabetic effects in subjects receiving these supplements. While selenium replaces sulfur in what are normally sulfur-containing molecules in yeast during the selenium enrichment process, there will always be a preponderance of sulfur-containing molecules in the final preparation (sulfur is a macro element and is impossible to remove completely from any growth or fermentation process). Thus, the presence of certain sulfur-containing molecules in selenium-enriched yeast may, in some cases, inhibit mitochondrial activity and lead, over time, to a pro-diabetic state. It is well documented in the literature that adult-onset diabetes is linked to a gradual decline in mitochondrial activity over a period of several years. This is particularly important in the case of skeletal muscle which, it is estimated, uses 75-80% of daily ingested glucose. Even modest declines in the ability of muscle mitochondria to efficiently utilize glucose can, over time, lead to serious health problems. The two-fold stimulation of mitochondrial activity noted in C2C12 muscle cells in response to compound D, for example, may represent a way to avoid or delay mitochondrial decline in the muscle tissue of pre-diabetic or diabetic subjects.

To investigate whether the observed increase of MT potential by compound C and D is simply caused by an increase in viable cell number, we performed a cell viability assay. It was found that compound C and D did not affect cell viability in C2C12 cells after treatments with these compounds at the same doses for 24 hr and 48 hr (data not shown). Together, our results suggest that compound C and D did not have a negative effect on cell survival, but can transiently enhance MT potential in C2C12 cells.

MT Potential Transiently Enhanced by Compound C, D, and E in IMR-32 Cells

Figure 3:
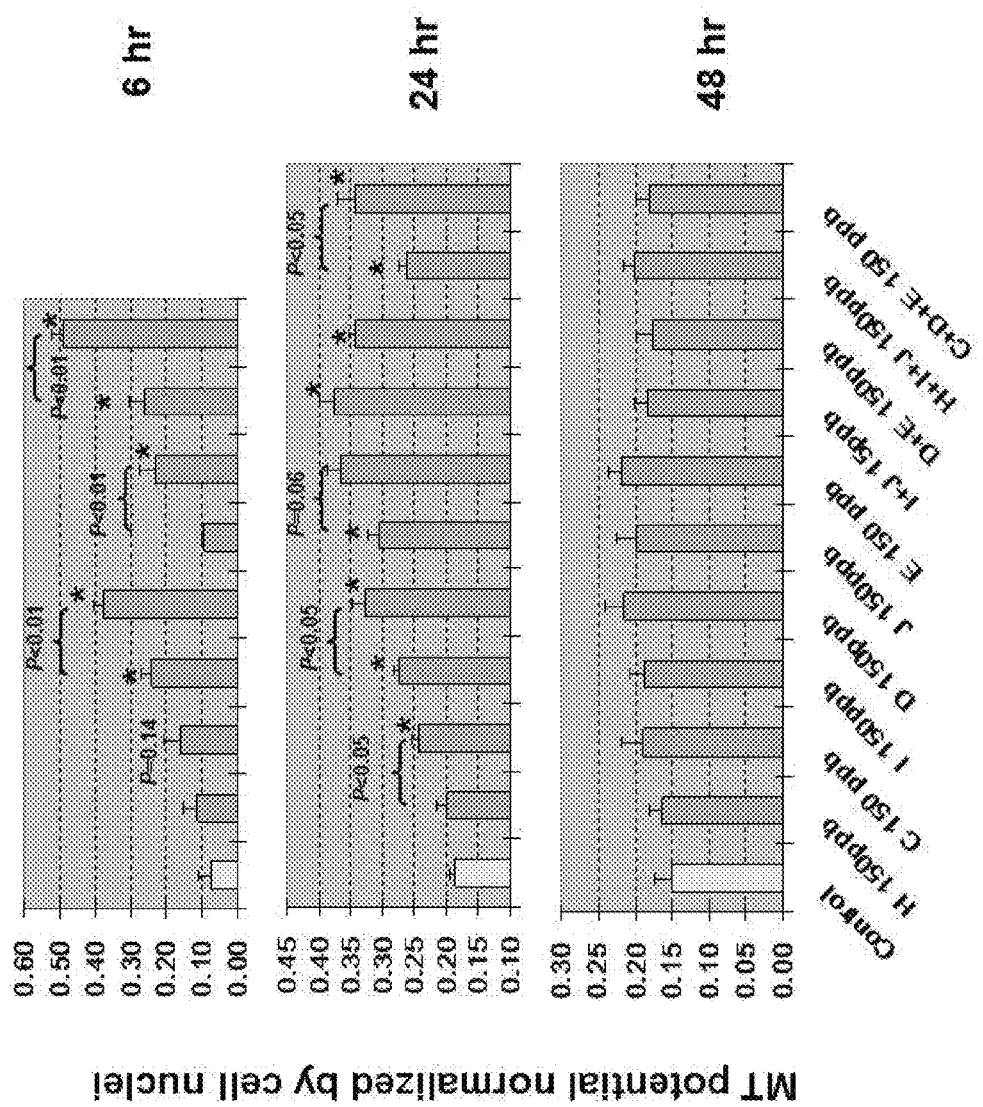
FIG. 3 shows a transient increase of mitochondrial ("MT") potential in IMR-32 human neuronal cells treated with compounds C (5'-Methylselenoadenosine), D (Se-Adenosyl-L-homocysteine), and E (Gamma-glutamyl-methylseleno-cysteine) or combinations thereof at 6 hours and 24 hours. Their sulfur analogs H (5'-Methylthioadenosine), I (S-Adenosyl-L-homocysteine), J (Gamma-glutamyl-methyl-cysteine) and combinations thereof also exhibited a transient increase in mitochondrial function. Data were normalized by the fluorescence intensities of stained cell nuclei. * denotes P values vs control.

To investigate whether selenium compounds can regulate MT function in neuronal cells, human IMR32 cells were treated with various compounds for 6, 24 and 48 hr, and then subjected to mitochondrial potential assays. As shown in FIG. 3 (top panel), treatment of compound D or E or a combination of both for 6 hr significantly enhanced MT potential when compared to control normal cells (with water vehicle treatment) while a trend towards elevated MT potential was also observed in compound C-treated IMR-32 cells.

Increased MT potential was also observed in cells treated with compound H or I and J (when compared to control, FIG. 3 top panel). However, the enhanced MT potential was more pronounced in cells treated with compound D or E or a DE combination than their respective sulfur analog(s) (FIG. 3 top panel).

At 24 hr after compound treatment, a significant increase in MT potential was observed in all selenium compound-treated cells (when compared to control). In general, enhanced MT potential was more pronounced in cells treated with selenium compound C, D, E or a combination of CDE than their sulfur analogs H, I, J, or a combination of HIJ. It should be noted that in one instance at the 24 hr time point the combination of I and J elicited the highest mitochondrial response. However at 48 hr, there was no significant change in MT potential among all tested groups. Together, these results suggest that selenium compound C, D, E or a combination of these compounds can transiently enhance the MT potential in IMR-32 cells, and the effects of these selenium compounds are more evident than their sulfur analogs.

Once again, there is a marked cell-specific and compound-specific response evident in this experiment which underscores the differential response of cell types to these specific selenium compounds and their combinations. Moreover, instead of being inhibitory to mitochondrial activity as in the case of muscle cells, sulfur compounds stimulated mitochondrial activity in IMR-32 cells—albeit to a generally lesser extent that selenium compounds. The transient or temporal effect noted in this case indicates that these compounds or their combinations would have to be repeatedly administered to a treated subject in order to maintain an effect on mitochondrial activity; in essence, a daily dose might be required.

MT Potential Elevated by Repeated D or E Treatments in IMR-32 Cells for a Total of 48 Hrs.

Figure 4:
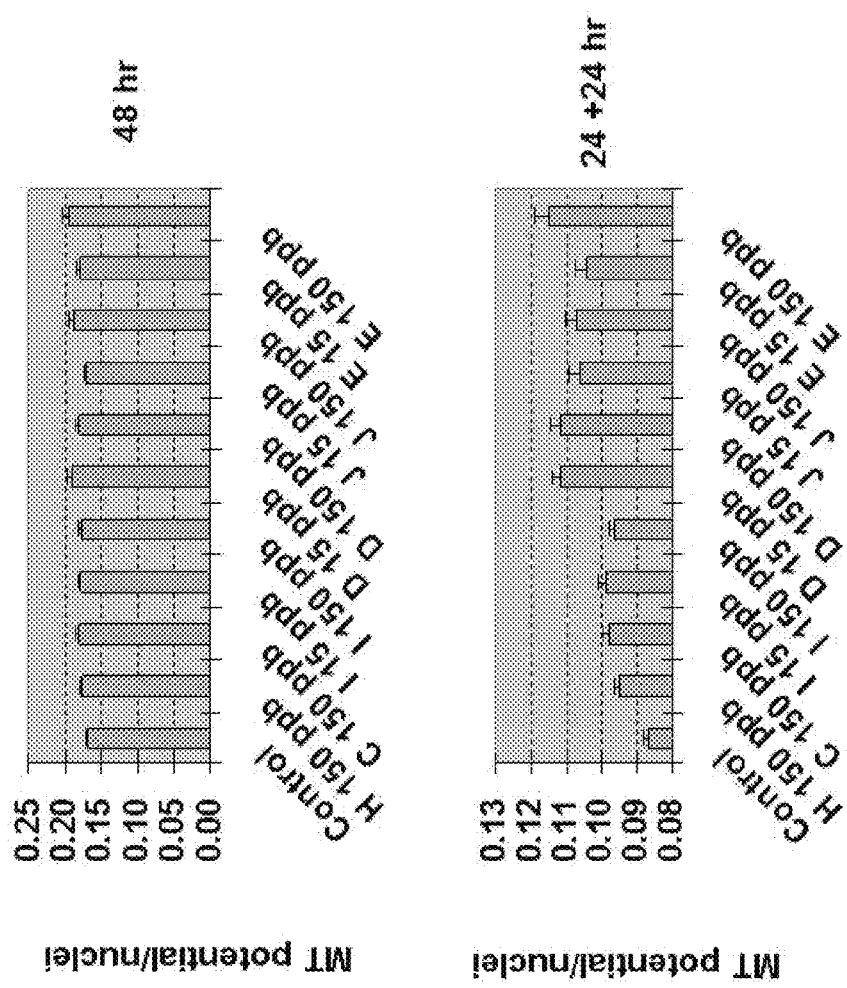
FIG. 4 shows that repeated treatments of C (5'-Methylselenoadenosine), D (Se-Adenosyl-L-homocysteine), and E (Gamma-glutamyl-methylseleno-cysteine) or their sulfur analogs H (5'-Methylthioadenosine)), I (S-Adenosyl-L-homocysteine), J (Gamma-glutamyl-methyl-cysteine) enhanced mitochondrial (MT) potential in IMR-32 neuronal cells. Cells were treated once with compounds for 48 hours (hr.) (top panel) or twice with compounds for a total of 48 hours. (bottom panel). Data were normalized by the fluorescence intensities of stained cell nuclei.

The above observed transient effects of compound C, D and E on MT potential prompted us to test whether repeated treatments can enhance the MT potential. Thus, IMR-32 cells were first treated with compound C, D or E for 24 hr, and then re-treated with freshly prepared compound C, D or E for another 24 hr. As a negative control, IMR-32 cells were treated only once with compound C, D, or E for 48 hr. Then, MT potential assays were performed on these cells. As anticipated, prolonged single treatments of compound C, D, or E for 48 hr (continuous 48 hr single treatment) did not affect MT potential in IMR-32 (FIG. 4 top panel). However, repeated treatments of compound D (at both 15 and 150 ppb) or E (at the dose of 150 ppb) significantly enhanced MT potential (when compared to control or the sulfur analogs I or J).

No Toxic Effects of Compound C, D, E on the Cell Survival of IMR-32 Cells

Figure 5:
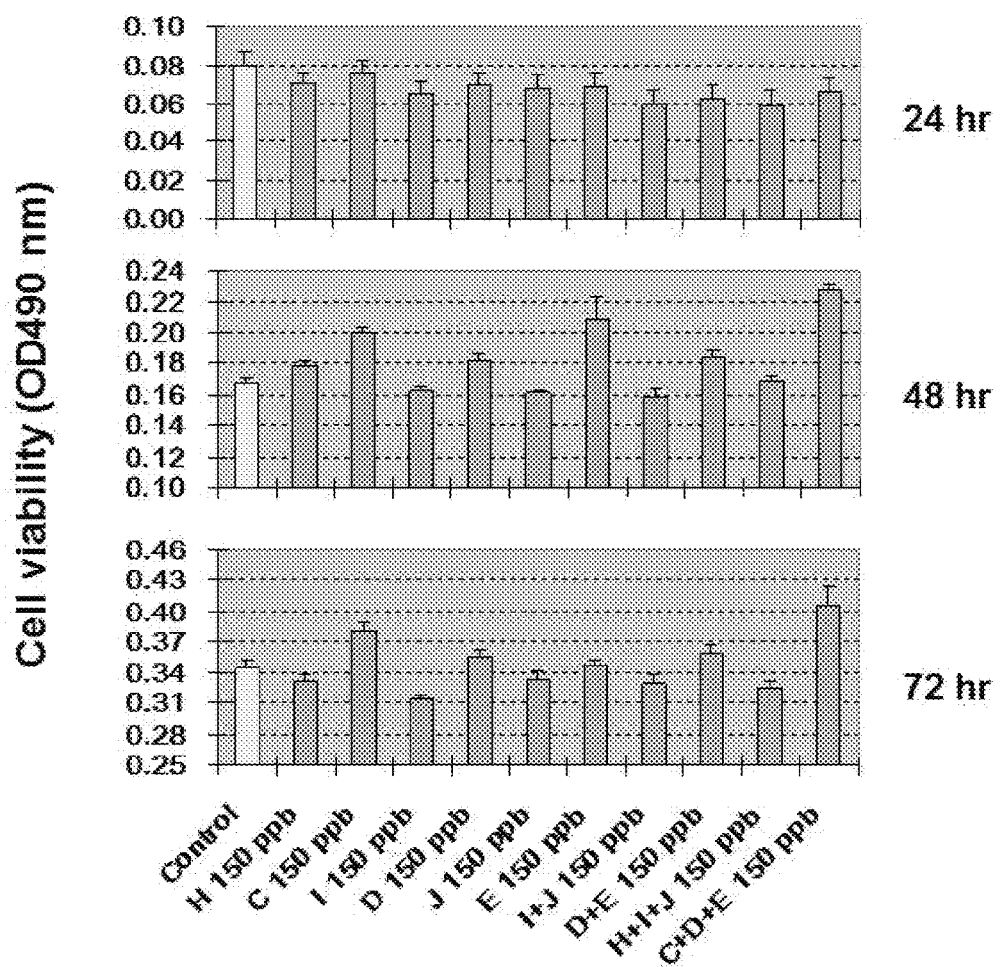
FIG. 5 shows the lack of toxic effects of compounds C (5'-Methylselenoadenosine), D (Se-Adenosyl-L-homocysteine), and E (Gamma-glutamyl-methylseleno-cysteine) or combinations thereof on the viability (indicated by OD490 nm) of human IMR-32 neuronal cells over a 72 hour time period. In contrast, sulfur analogs H (5'-Methylthioadenosine)), I (S-Adenosyl-L-homocysteine), J (Gamma-glutamyl-methyl-cysteine) and combinations thereof exhibited a slight decrease in viability over the 72 hour time period. The results are shown as mean±sem; n=8.

To test whether there is any toxic effect of selenium compounds on the survival of IMR-32 cells, cell viability assays were performed on cells after treatment with various compounds for 24, 48 and 72 hr. As shown in FIG. 5, treatment of all compounds for the tested time points did not cause a significant decrease of viable cells in IMR-32. In fact, there was a small but significant increase of cell viability in cells after selenium compound treatments for 48 and 72 hr (FIG. 5 middle and bottom panels). These data suggest that selenium compounds did not have a toxic effect on the survival of IMR-32 cells, but instead, had a small but significant beneficial effect on neuronal cell survival. It should be noted, however, that any observed increases in cell viability in this experiment are too slight to account for the increases in MT potential observed in the IMR-32 cell line in response to certain selenium compounds or their analogs.

Experimental Data to Demonstrate the Ability of Selected Synthetic Selenium Compounds to Increase or Decrease Mitochondrial Activity on Isolated Mitochondrial from Rat Brains.

A water soluble extract was obtained from selenized yeast. The water-soluble extract accounts for up to 25% of the total selenium present in the preparation. We reasoned that these selenium species would be the first to be liberated/digested from selenized yeast in its passage through the intestinal tract. Following identification of the selenium containing compounds in the extract by mass spectroscopy, we synthesized a number of selenium containing compounds and peptides, Accordingly, this round of synthesis and purification resulted in a panel of nine (9) selenium-containing species for further testing. Given the small quantities of the materials thus generated (low milligram quantities) it was deemed impractical to conduct feeding studies in live animals. Because we were primarily interested in the potential effects of these selenium species on mitochondrial bioenergetics, it was decided to test these selenium molecules directly using mitochondria.

Selenium concentration ranges low (50 ppb), mid (500 ppb) and high (1 ppm) were initially tested as a possible range for the compounds. Based on no observable toxicity against mitochondria in the mid-range, we selected 500 ppb (5 uM) concentration for performing our compound screens using mitochondrial bioenergetics as the primary outcome measure. Adult rat brain ficoll purified mitochondria were incubated with the 9 compounds for 30 min at 37° C. prior to being loading into the Seahorse Biosciences flux analyzer in triplicate. We measured OCR (Oxygen Consumption Rates) parameters in three respiratory states including ATP synthesis (State III), Complex I dependent (NADH-driven) Maximum Respiratory Capacity (State $V_{FCCP}$) and Complex II (FADH-driven) dependent Maximum Respiratory Capacity (State $V_{succ}$).

The results show that different selenium compounds derived from the water extract had differential activity in being able to increase mitochondrial potential.

Compound 5: Valine-Selenomethionine-Arginine

Compound 6: Leucine-Valine-Selenomethionine-Arginine

Compound 7: Leucine-Threonine-Glycine-Selenomethionine-Alanine-Phenylalanine-Arginine Compound 8: Selenoglutathione dimer Compound 9: MethylSelenoadenosine Compound 10: Glutamylselenocysteine Compound 25: Total water extract of yeast at pH 6.0

Compound 28: Glutathione oxidized

Compound 30: Glutamylcysteine

TABLE 1

Selenium compounds effects on mitochondrial bioenergetics
(rat brain purified mito 5 ug/well)

|   | CTRL | STATE III 432.6 | % Change | STATE V 182.1 | % Change | STATE Vsucc 350.1 | % Change |
|---|------|-----------------|----------|---------------|----------|-------------------|----------|
| * | #5   | 445.9 | 3.0   | 187.8 | 3.2   | 292.5 | -16.4 |
| + | #6   | 477.5 | 10.3  | 220.6 | 21.2  | 376.4 | 7.6   |
| - | #7   | 372.5 | -14.0 | 147.1 | -19.2 | 288.0 | -17.7 |
| * | #8   | 424.0 | -2.1  | 192.3 | 5.7   | 371.0 | 6.0   |
| + | #9   | 507.8 | 17.3  | 210.3 | 15.6  | 437.1 | 24.9  |
| - | #10  | 352.1 | -18.7 | 112.7 | -38.1 | 254.4 | -27.3 |
| - | #25  | 419.0 | -3.2  | 136.2 | -25.2 | 309.3 | -11.6 |
| * | #28  | 451.6 | 4.3   | 149.6 | -17.8 | 319.3 | -8.8  |
| * | #30  | 423.2 | -2.3  | 153.8 | -15.5 | 305.4 | -12.7 |

+ Positive Trend
* Positive/Negative trend
- Negative Trend

In particular, compounds 6 and 9 increased mitochondrial potential while compounds 7, 10, and 25 inhibited mitochondrial potential. These results show that compounds derived for a water extract of selenized yeast have very different effects on mitochondrial potential and led us to isolate, screen, and synthesize candidate compounds with a view to selecting only those which elicit positive responses on biological processes.

Experimental Data to Demonstrate the Ability of Synthetic Selenium Compounds to Restore Stressed Mitochondria to Normal Activity in Isolated Mitochondrial from Rat Brains.

Figure 6:
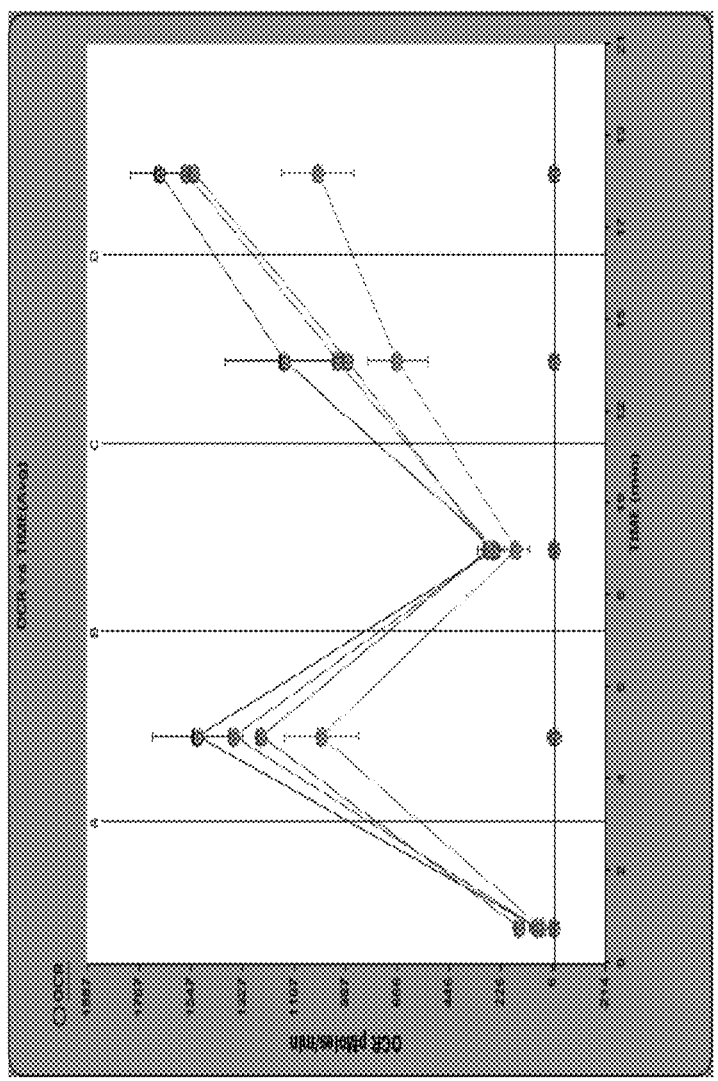
FIG. 6 shows the restoration of mitochondrial function by compounds D and E in rat cortex cells stressed by 10 micromolar calcium. The figure shows the respiration chart of normal mitochondria (top line) with the final OCR being the measured distance between the end of the graph line and the X-axis. The bottom line shows the inhibition of respiration of mitochondria by 10 micromolar calcium. The two lines in the middle represent the respiration of mitochondria in the presence of compounds C or D and 10 micromolar calcium.

The following example describes an experiment performed in the SeaHorse external flux analyzer; an instrument for measuring the respiration rate of mitochondria expressed as the oxygen consumption rate, or OCR. The experiment in question used mitochondria from the brain cortex of normal rats, maintained on normal laboratory chow which had not been fortified with any additional selenium sources. FIG. 6 shows the respiration chart of normal mitochondria (top line) with the final OCR being the measured distance between the end of the graph line and the X-axis.

An identical sample of the same mitochondrial preparation was treated in exactly the same manner as the control sample except that calcium (10 micromolar final concentration) was added to stress or damage the mitochondria by depolarizing them. As shown (bottom line) the OCR dropped from a value of 1,677 to 1,066 pMoles/min $O_2$.

Again, identical samples of rat brain cortex mitochondria were incubated as above except that they contained calcium (10 µM) and 150 ppb of compounds D and E, respectively. C was not tested. It is evident that the OCR of the compound-treated, calcium-stressed mitochondria were restored to near control levels, i.e. 1,564 pMoles/min O2 in the case of compound D and 1,531 pMoles/min O2 in the case of compound E.

Based on this result and those of repeat experiments using rat brain mitochondria, we conclude that the synthetic selenium compounds not alone have the ability to increase the mitochondrial activity of normal mitochondria (see examples using unstressed cells of various types) but can also restore the respiratory capacity of stressed or damaged mitochondria.

Figure 7:
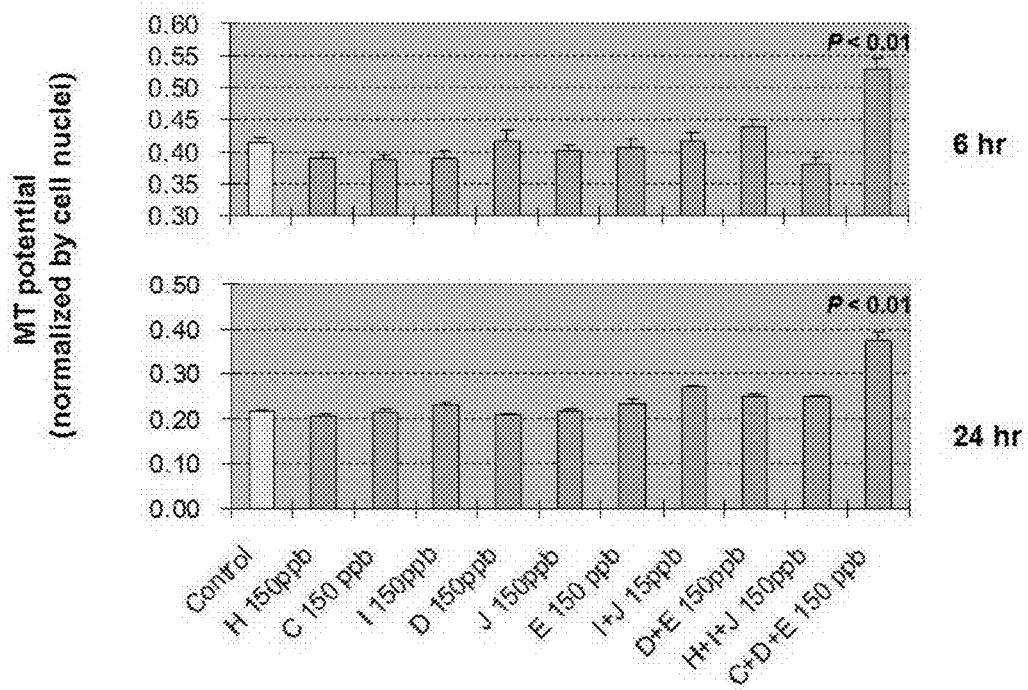
FIG. 7 shows a significant increase of mitochondrial (MT) potential in AML-12 mouse liver cells treated with the combination of selenium compounds C (5'-Methylselenoadenosine), D (Se-Adenosyl-L-homocysteine), and E (Gamma-glutamyl-methylseleno-cysteine)(150 ppb of each compound) as compared to a combination of H (5'-Methylthioadenosine)), I (S-Adenosyl-L-homocysteine), and J (Gamma-glutamyl-methyl-cysteine) at 6 and 24 hours. Data were normalized by the fluorescence intensities of stained cell nuclei. The P values shown in the bar graphs were determined by comparing CDE group to control or HIJ group.

MT Potential Enhanced by the Combination of C, D, and E, but not by Individual Compounds in Mouse Liver AML-12 Cells To investigate whether selenium compounds can regulate MT function in liver cells, mouse AML-12 cells were treated with various compounds for 6 and 24 hr, and then subjected to mitochondrial potential assays. As shown in FIG. 7, separate treatments with compounds C, D, or E at 150 ppb or their respective sulfur analogs at the same concentration did not significantly affect MT potential when compared to control normal cells (with water vehicle treatment). However, the combination of C, D and E caused a highly significant increase of MT potential when compared to both vehicle- or HIJ-treated groups (FIG. 7). Thus, in liver cells, a specific combination of compounds C, D and E is required to elicit an increase in MT potential while the individual compounds and their sulfur analogs have no effect. This effect is totally different from that observed in neuronal cells and has never been documented before in the literature.

UCP2 Expression is Downregulated by the Combination of Compound C, D and E in AML-12 Cells One candidate family of genes which have the ability to increase or decrease mitochondrial activity are the so-called Uncoupling Protein Genes or UCPs. The elevated MT potential observed in response to treatment with the CDE combination led us to test whether there is differential regulation of these genes in vehicle-, HIJ- and CDE-treated AML-12 cells. In normal AML-12 cells, Ucp2 mRNA expression levels were four hundred sixteen-fold higher than Ucp1, while Ucp3 mRNA was undetected by real-time RT-PCR (FIG. 8A, Ucp3 data not shown). Treatment of AML-12 cells with CDE compounds did not affect Ucp1 expression (FIG. 8B). However, there was a significant decrease of Ucp2 mRNA expression in AML-12 cells after treatment with CDE but not HIJ (FIG. 8C). As Ucp2 can inhibit MT potential, reduced Ucp2 expression may be at least a partial cause of the enhanced MT potential elicited by CDE compounds in AML-12 cells. Since obese patients generally have high levels of Ucp2 in the liver, reduced Ucp2 expression by CDE indicates that CDE compounds may be beneficial for the treatment of obesity.

No Toxic Effects of CDE Compounds on the Survival of AML-12 Cells

Figure 9:
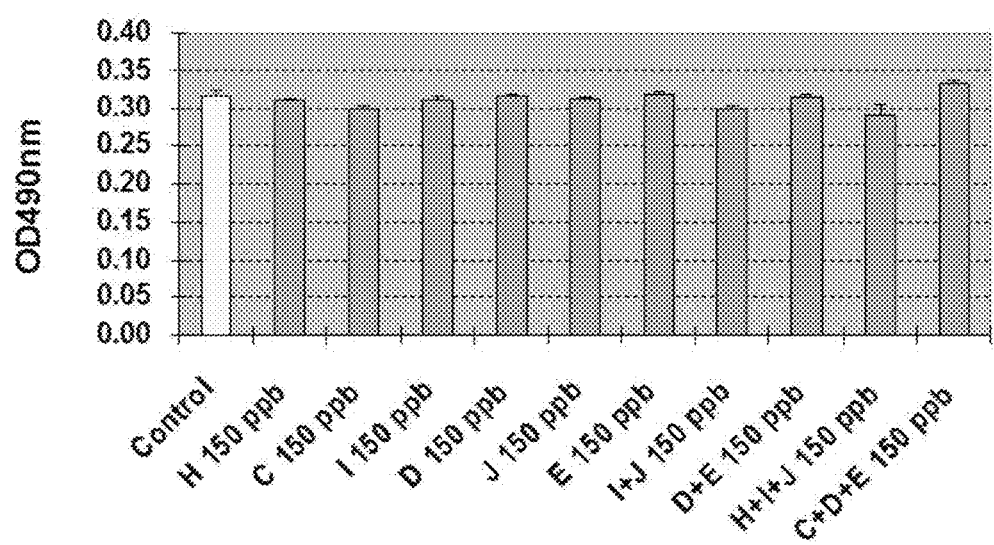
FIG. 9 shows no toxic effects of compounds C (5'-Methylselenoadenosine), D (Se-Adenosyl-L-homocysteine), E (Gamma-glutamyl-methylseleno-cysteine) and combinations thereof or their sulfur analogs H (5'-Methylthioadenosine)), I (S-Adenosyl-L-homocysteine), J (Gamma-glutamyl-methyl-cysteine) and combinations thereof on the viability (indicated by OD490 nm) of AML-12 mouse liver cells.

To test whether there is any toxic effect of selenium compounds on the survival of AML-12 cells, cell viability assays were performed on cells after treatment with various compounds for 48 hr. We found that no treatment (both single compounds and their combinations) caused a significant decrease of cell viability in AML-12 cells (FIG. 9) which confirms that selenium compounds did not have the toxic effect on the survival of AML-12 cells.

Figure 10:
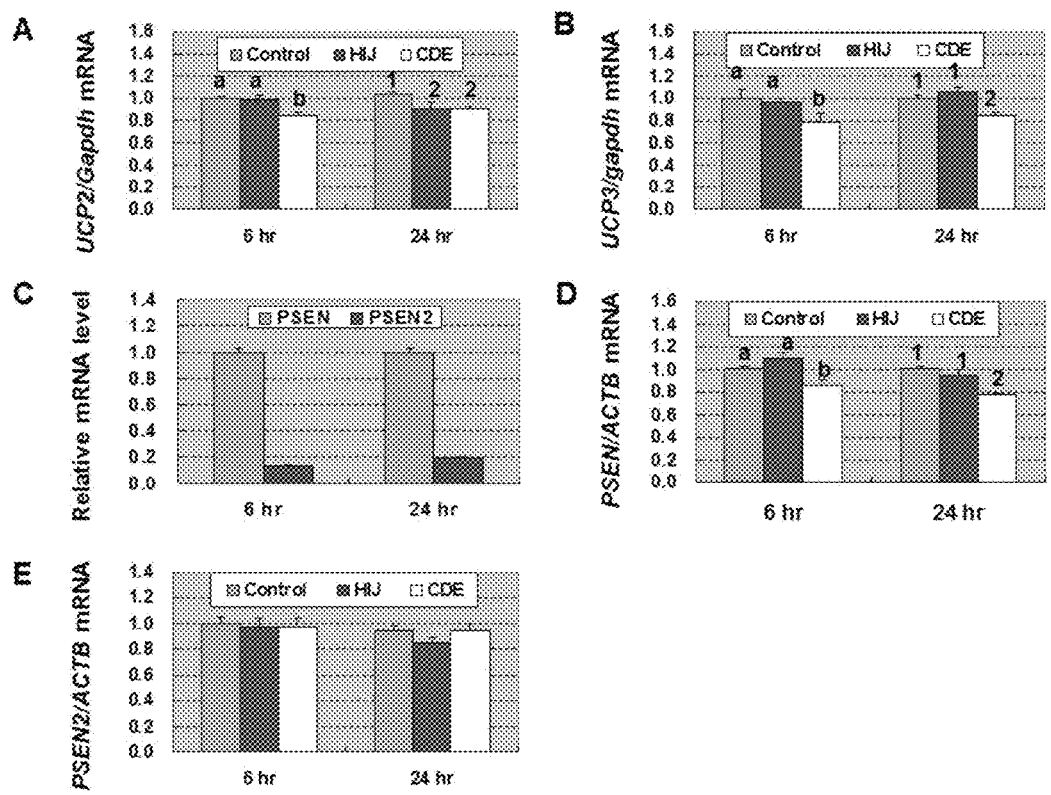
FIG. 10 shows downregulation of Ucp2, Ucp3 and Presenilin (PSEN) expression in human IMR-32 neuronal cells after the treatment with the combination of C (5'-Methylselenoadenosine), D (Se-Adenosyl-L-homocysteine), and E (Gamma-glutamyl-methylseleno-cysteine) (150 ppb of each compound) compounds. (A) Ucp2 mRNA expression at 6 and 24 hours. (B) Ucp3 mRNA expression at 6 and 24 hours. (C) Relative PSEN and PSEN2 mRNA level in human IMR-32 neuronal cells treated with vehicle (water) at 6 and 24 hours. (D) PSEN mRNA expression after normalization by the amount of actin beta (ACTB) mRNA level in human IMR-32 neuronal cells treated with a combination of C (5'-Methylselenoadenosine), D (Se-Adenosyl-L-homocysteine), E (Gamma-glutamyl-methylseleno-cysteine) (150 ppb of each compound or a combination of H (5'-Methylthioadenosine), I (S-Adenosyl-L-homocysteine), and J (Gamma-glutamyl-methyl-cysteine) (150 ppb of each compound) at 6 and 24 hours. (E) PSEN2 expression after normalization by (ACTB) mRNA level in human IMR-32 neuronal cells treated with a combination of C (5'-Methylselenoadenosine), D (Se-Adenosyl-L-homocysteine), and E (Gamma-glutamyl-methylseleno-cysteine) or a combination of H (5'-Methylthioadenosine)), I (S-Adenosyl-L-homocysteine), and J (Gamma-glutamyl-methyl-cysteine) at 6 and 24 hours. Data are presented as mean±sem of 3-4 samples per group. Different alphabetic letters (a vs. b) and different numbers (1 vs. 2) in the bar graph means a significant difference among those groups (P<0.05)

Downregulation of UCP2/3 by the Combination of Compounds C, D and E in IMR-32 Cells As mentioned earlier, UCPs such as Ucp1, 2 and 3 are critical genes for the regulation of MT potential. The elevated MT potential observed in IMR-32 cells in response to CDE (FIG. 3 top two panels) prompted us to test whether there is differential expression of these three genes in response to the combination treatment. It was found that Ucp1 mRNA was undetectable in normal IMR-32 cells by real-time RT-PCR analysis (data not shown). Treatment of IMR-32 cells with CDE compounds but not HIJ for 6 hour caused a significant decrease of both Ucp2 and Ucp3 expression (FIG. 10A-B). At 24 hr. treatment, Ucp2 expression was significantly decreased in both HIJ- and CDE-treated groups (FIG. 10A), while a significant decrease of Ucp3 expression was also observed in CDE-treated IMR-32 cells (FIG. 10B). These results suggest that the downregulation of Ucp2/3 may be at least one reason for the enhanced MT potential observed in IMR-32 cells in response to CDE compounds.

Discussion

Thus, we have presented evidence that three synthetic organoselenium compounds have the ability, either singly or in various combinations, to significantly increase mitochondrial activity in diverse cell types; namely, kidney cells, skeletal muscle cells, neuronal cells and liver cells. Mechanistically, we note that modulation of UCPs may offer one explanation for this increase and present evidence below that the expression of other proteins, critical to mitochondrial function and biogenesis, may also be favorably affected by these compounds. Regardless of mechanism of action, however, the fact that these compounds can stimulate mitochondrial activity in a cross-tissue manner means that they may be particularly valuable in ameliorating the onset and progress of seemingly diverse diseases; for example, Alzheimer's disease (AD) and Type2Diabetes (T2DM).

In the case of Alzheimer's disease, there has been a rapid growth in the literature supporting the idea that AD originates from impaired glucose import, defective energy metabolism, mitochondrial dysfunction, chronic oxidative stress and DNA damage in the brain (reviewed by de la Monte and Wands, 2008). For example, many studies have concluded that insulin deficiency and insulin resistance can mediate many of the effects noted in AD-degeneration. Furthermore, it has been found that T2DM causes brain insulin resistance, oxidative stress and cognitive impairment. Extensive disturbances in brain insulin and Insulin-like Growth Factor (IGF)-signaling mechanisms can account for a number of the molecular, biochemical and histopathological effects seen in AD.

A well-known statistic, published by the Alzheimer's Association of America, states that some 80% of AD sufferers also have T2DM. These, and other reasons, have led to many researchers using the term "Type-3 Diabetes" to reflect the fact that AD represents a form of diabetes that selectively involves the brain and has molecular and biochemical features that overlap with both Type 1 and Type 2 diabetes.

The link between AD and Type-2 diabetes is becoming very solid in the scientific literature but what is the link between these diseases and mitochondrial dysfunction? It is that T2DM, which combines defects in insulin secretion by the pancreas and insulin resistance in peripheral tissues, most notably liver and skeletal muscle, is caused by a modest and gradual loss of mitochondrial respiratory function over a prolonged period (Lowell and Shulman, 2005). Any agent, therefore, which can increase mitochondrial function in diverse tissues may be extremely valuable as an intervention for conditions tracing their origins to mitochondrial decline.

Results and Discussion of Alzheimer's Disease Pathogenesis

Downregulation of PSEN by the Combination of Compounds C, D and E in IMR-32 Cells IMR-32 cells have been reported to be an appropriate in vitro model system for the study of the pathogenesis of Alzheimer's disease (AD). (Neill et al., J. Neuroscience Res. 1994 39:482). One of the key pathological features of AD are Amyloid Plaques which occur between neurons and which contribute to brain atrophy and cell death. The mechanisms involved in the production of amyloid plaques are complicated but chiefly rely on the action of an enzyme called beta-secretase (BACE) which acts in concert with a multi-enzyme complex called gamma-secretase. Together, in AD, these enzymes act to aberrantly process a brain protein called amyloid precursor protein (APP). The resulting product is an abnormal amyloid beta peptide which clumps together to form plaques.

As stated, the gamma-secretase enzyme is actually a multimeric complex composed of four known members: Presenilin-1 (PSEN1 or PSEN), Nicastrin, APH-1 (Anterior Pharynx Defective 1) and PEN2 (Presenilin Enhancer 2). The other paralog of PSEN is Presenilin2 or PSEN2. While all four components are important for the correct functioning of gamma-secretase, two components in particular have become the focus for pipeline therapeutic drugs. These are Presenilin1 and Nicastrin. This is because Presenilin 1 is the actual catalytic component of the gamma-secretase—the component that physically cleaves the amyloid precursor protein. Furthermore the gene for Presenilin 1 is the most frequently mutated gene in familial AD. Relative to PSEN2, PSEN1 is much more abundant and is functionally better defined. Nicastrin is of interest, not because it is catalytic but because it binds to and orients APP so that Presenilin can cleave it. PSEN 1 and Nicastrin are, therefore, the targets of greatest interest for gamma-secretase-focused AD interventions.

It should also be noted that AD is thought by several research groups to have its origins in a gradual decline in mitochondrial function, as a person ages. In this regard, it is also of interest to note that one of the first physiological changes measurable in the AD disease process is a defective uptake and utilization of glucose by brain cells; clearly, both these phenomena may be linked. Accordingly, we examined the expression of the genes encoding the PSENs in IMR32 cells treated with a combination of compounds C, D, and E (CDE), alongside a combination of their sulfur analogs (HIJ).

We found that the expression of PSEN was almost eight-fold higher than PSEN2 in normal IMR32 cells (FIG. 10C). More importantly, PSEN1 expression was significantly decreased in CDE-treated cells when compared to control or HIJ group (FIG. 10D). In contrast, there was no obvious change in PSEN2 expression among control, HIJ and CDE groups (FIG. 10E). These results suggest that selenium compounds can selectively down-regulate PSEN but not PSEN2 expression in IMR-32 cells and there may exist a lead substance among CDE compounds against amyloid plaque formation.

Compound C, a Lead Compound for Preventing the Cleavage of APP for Plaque Formation in AD by Targeting the Gamma-Secretase Complex Genes PSEN and Nicastrin in IMR-32 Cells As shown above (FIG. 10D), compound CDE mixtures inhibited PSEN expression, indicating that there exists a biological lead among these three compounds against gamma-secretase components for the production of amyloid beta peptide. That study was limited to PSEN expression but, because gamma secretase is a multi-enzyme complex, another important component protein, Nicastrin, was included in this particular example. In order to identify the lead compound, IMR-32 cells were treated with individual compounds and subjected to Western blot and RT-PCR analyses.

Figure 11:
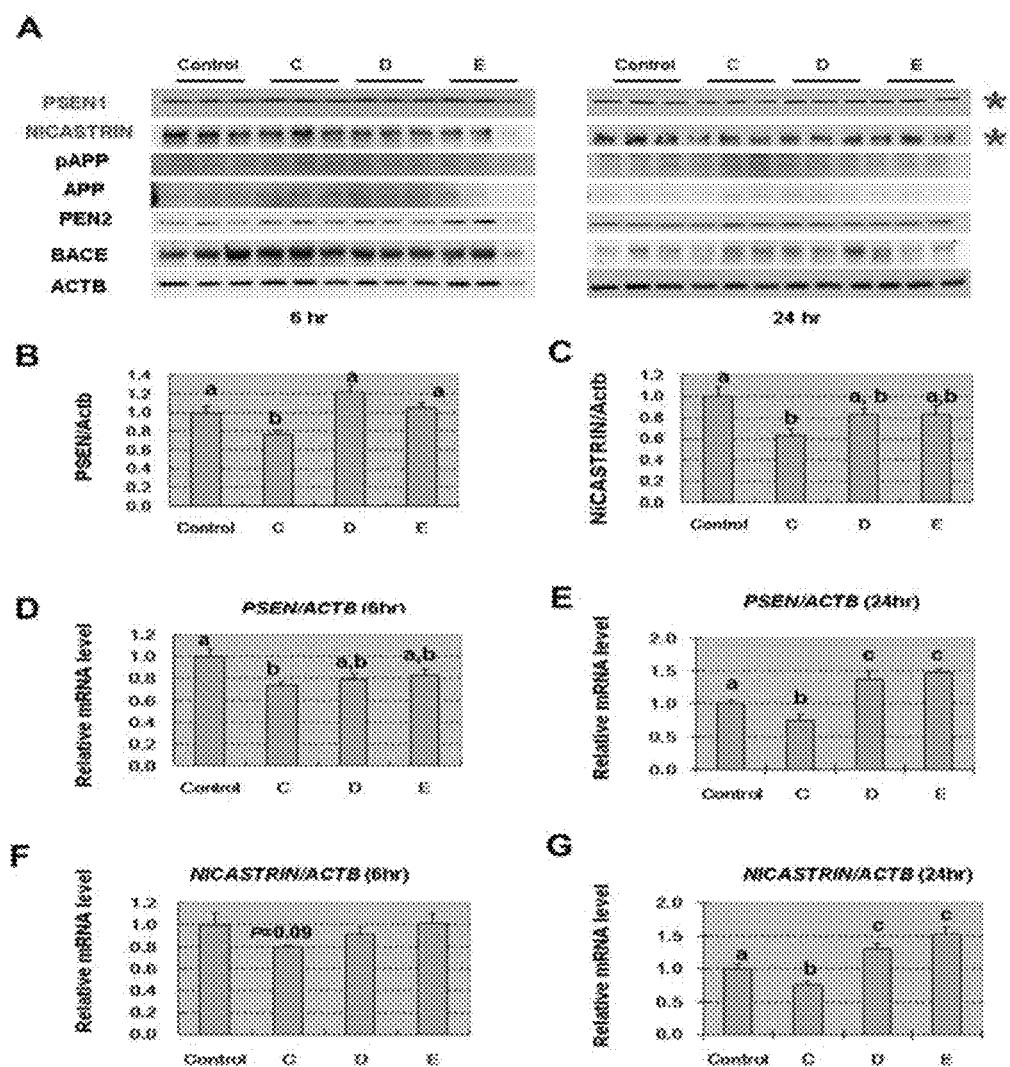
FIG. 11 shows gamma secretase complexes PSEN and Nicastrin were the targets of Compound C (5'-Methylselenoadenosine) as determined by Western blot and real time polymerase chain reaction ("RT-PCR") analyses. (A) Photographs of Western blot analysis of various proteins (key for plaque formation in Alzheimer's disease (AD) in human IMR-32 neuronal cells treated with 150 ppb compound C (5'-Methylselenoadenosine), D (Se-Adenosyl-L-homocysteine), or E (Gamma-glutamyl-methylseleno-cysteine) for 6 and 24 hours. (B-C) Quantitative analysis of (B) PSEN and (C) Nicastrin protein levels in the above Western blots (after treatment with the listed compound for 24 hours, right panel). Data are presented as mean±sem of 3 samples. (D-G) Quantitative RT-PCR analysis of (D-E) PSEN and (F-G) Nicastrin expression in human IMR-32 neuronal cells treated with water vehicle (control) and the listed compounds for (D, F) 6 and (E, G) 24 hr. Data are presented as mean±sem of 4 samples. Different letters (a vs. b, a vs. c, or b vs. c) in the bar graphs means a significant difference between those two groups (P<0.05). The letters "a,b" denote no significant difference from a or b.

As shown in FIG. 11A, PSEN and Nicastrin, but not PEN2 and beta-secretase BACE proteins were attenuated in IMR-32 cells after 24 hr of treatment by compound C. Quantitative analysis showed that there was a significant reduction of both PSEN and Nicastrin protein levels only by C, while the D and E compounds also elicited a trend towards reduced Nicastrin protein expression (FIG. 11B-C). Consistent with attenuated PSEN expression, PSEN mRNA expression was significantly reduced by compound C not only at 6 hr but also at 24 hr. of treatment (FIG. 11 D-E). Similarly, compound C treatment also caused a trend towards reduced Nicastrin mRNA expression in IMR-32 cells after 6 hr. treatment, (FIG. 11F), and, more importantly, a significant decrease in Nicastrin mRNA expression in IMR-32 cells after 24 hr treatment (FIG. 11G). In contrast, compounds D and E treatments did not inhibit, but instead stimulated PSEN and Nicastrin mRNA expression in IMR-32 cells (FIGS. 11E and 11G).

Together, our data suggested that compound C can inhibit both PSEN and Nicastrin expression at both mRNA and protein levels. These results suggest that compound C is an anti-AD compound of the three candidates and achieves this by targeting gamma-secretase complex components, more specifically PSEN and Nicastrin, which are known to be responsible for plaque formation in AD.

Compound C, a Cell-Specific GSK3b Downregulator Against the Hyperphosphorylation of Tau Protein in IMR-32 Cells The second main pathology, besides amyloid plaques, in AD is called the Neurofibrillary tangle, NFT or tangle for short. It has been well characterized that tangle formation in AD is caused by hyperphosphorylation of a protein called Tau and that this phosphorylation is caused by kinase enzymes such as DYRK1A (Dual specificity tyrosine-phosphorylation-regulated kinase 1A) and mainly Gsk3b (Glycogen synthase kinase 3 beta). To explore whether the selenium compounds C, D or E can potentially contribute to diminished tangle formation in AD, we first investigated the phosphorylation status of two AD biomarkers, pTau 5396 and pTauS400/T403/5404, as well as the total Tau protein concentration in IMR32 cells. Phosphorylation of Tau at the sites indicated has been associated with destabilization of the Tau protein and the eventual formation of tangles. For this purpose, cells were treated with compound C, D, and E for 6 and 24 hr, and then subjected to Western blot analysis.

As shown in FIG. 12A, protein levels of all tested Tau protein species were not affected at 6 hr treatment. However after 24 hr treatment, protein levels of pTauS396, pTauS400/T403/S404 and/or total Tau in IMR-32 cells were significantly downregulated by compound C and/or E. Quantitative analysis showed that compound C did not affect total Tau protein level, but significantly inhibited the phosphorylation of Tau at S400/T403/S404 but not at 5396 (FIG. 12B-C). Compound D had no effect on Tau phosphorylation at all tested serine/threonine residues, or on total Tau protein level, while the phosphorylation of Tau at S396 and S400/T403/S404, and total Tau protein were significantly downregulated by E compound (FIG. 12B-C).

Analysis of the ratio of total pTauS396 and pTauS400/T403/S404 to total Tau proteins showed that only compound C, but not D or E, significantly attenuated total phosphorylation of Tau protein in IMR-32, even though there was a trend of reduced Tau phosphorylation at all tested serine/threonine residues by compound E (FIG. 12E).

Together, our data showed that compound C can markedly inhibit Tau phosphorylation but does not affect total Tau protein in IMR32 cells, while compound D did not have any effect in the process. Compound E may also play a role in the regulation of Tau phosphorylation but the effect of this compound is likely through the down-regulation of total Tau protein in IMR-32 cells. Given that hyperphosphorylation of Tau is a cause of tangle formation in AD, our data suggest that C inhibits Tau hyperphosphorylation that contributes to tangle formation in AD.

To investigate whether the downregulation of Tau phosphorylation by compound C is due to Gsk3 and DYRK1A (two key kinases for Tau phosphorylation in AD), Western blot analysis was performed to examine their protein levels. As shown in FIG. 12A, phosphorylation of Gsk3b, total Gsk3a and DYRK1A proteins were not affected by any of the three compounds in IMR-32 cells. However, Gsk3b protein levels were visibly decreased in IMR-32 cells after treatment with compound C, but not D or E, for 24 hr but not 6 hr (FIG. 12A). Quantitative analysis showed that there was a statistically significant decrease of Gsk3b protein levels in Compound C, but not D or E, treated IMR-32 cells (when compared to control cells) (FIG. 12F).

To further confirm that Gsk3b expression is inhibited by compound C, quantitative RT-PCR was performed to examine its mRNA level. As shown in FIG. 12G, Gsk3b mRNA levels were significantly decreased in IMR32 cells after treatment with compound C for 6 hr. A trend of decreased Gsk3b mRNA expression was also observed in IMR-32 cells after treated with compound C for 24 hr (FIG. 12H). In contrast, compound D and E treatments for 6 hr did not significantly inhibit Gsk3b mRNA expression in IMR-32 cells (FIG. 12G). Instead, there was a significant increase of Gsk3b mRNA expression in IMR-32 cells after treated with compound D or E for 24 hr (FIG. 12H). Together, these data suggest that compound C can inhibit Gsk3b expression at both the mRNA and protein levels and that down-regulation of GSK3b by Compound C is likely the cause of reduced Tau phosphorylation indicated above.

Figure 16:
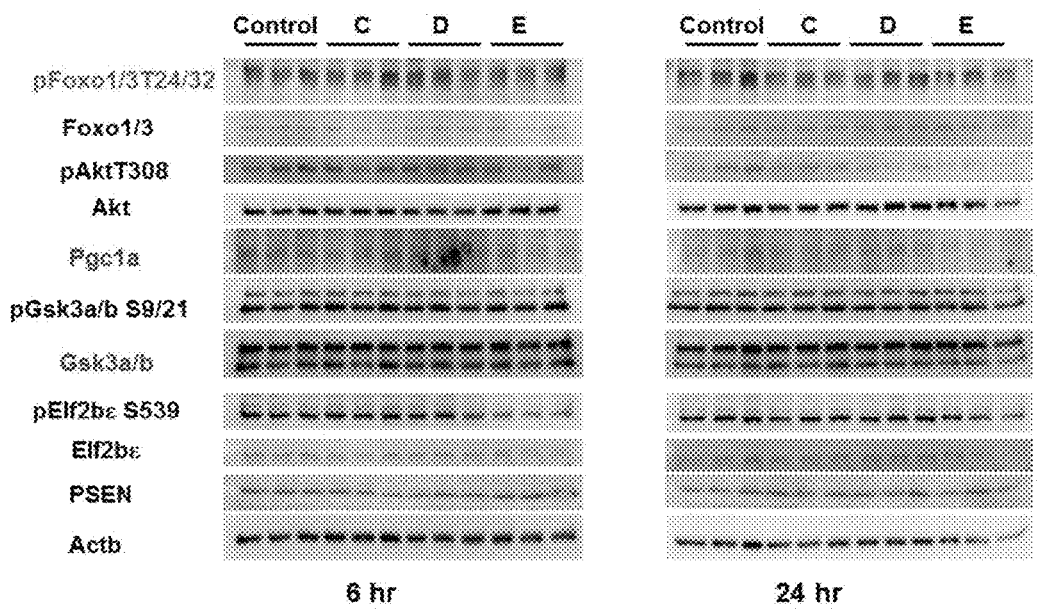
FIG. 16 shows a Western blot analysis of various listed molecules in mouse liver AML-12 cells after treated with vehicle (water, control), or compound C (5'-Methylselenoadenosine), D (Se-Adenosyl-L-homocysteine), or E (Gamma-glutamyl-methylseleno-cysteine), each at 150 ppb, for 6 and 24 hours.

To investigate whether the inhibitory effect of compound C on Gsk3b expression is neuronal cell-specific, we examined its protein levels in mouse liver cells. Protein extracts were prepared from liver cells at the same time and the same experimental conditions as the above IMR-32 cells. It was found that Gsk3b protein levels were not affected by compound C in liver cells (FIG. 16). Thus, the downregulation of Gsk3b expression is neuronal cell-specific. The lack of a GSK3b response to compound C in liver cells could be of significant value from a therapeutic perspective. It means that compound C could be used as a therapeutic in neuronal tissue without running the risk of causing serious disturbances to liver carbohydrate metabolism.

Together, our results suggest that Compound C is a neuronal cell-specific Gsk3b down-regulator and can inhibit phosphorylation of Tau in neuronal cells, which will be beneficial against tangle formation in AD. These data provide further in vitro evidence that compound C may be a valuable therapeutic in the field of AD.

Neuronal-Specific Downregulation of FOXO Phosphorylation and Upregulation of PGC1a Protein by CDE in IMR32 Cells Given the observed effects of CDE compounds on mitochondrial activity in IMR-32 cells, we wished to examine if these compounds can regulate key factors responsible for cellular growth and metabolism, mitochondrial function and energetics. The FOXO (Forkhead box) proteins are a family of key nuclear transcription factors, having diverse roles in cell proliferation, differentiation and longevity. They partially control key functions in the cell, such as gluconeogenesis (glucose production from non-carbohydrate substrates). Their entry into the cell nucleus is controlled by phosphorylation; phosphorylated FOXO is excluded from the nucleus while dephosphorylated FOXO can enter.

PGC1a (Peroxisome proliferator-activated receptor gamma coactivator 1-alpha) is a potent transcriptional activator that regulates genes involved in energy metabolism and is also the chief regulator of mitochondrial biogenesis and growth. It provides a direct link between external stimuli (such as exercise) and the regulation of mitochondrial biogenesis. It performs its diverse functions by teaming with different transcription factors to co-activate genes. In the context of neuronal-specific mitochondrial activity and AD progression, it is of interest to note that PGC1a expression decreases in the Alzheimer's disease brain as function of dementia (Qin et al., 2009. Arch Neurol; 66:352-361).

Figure 13:
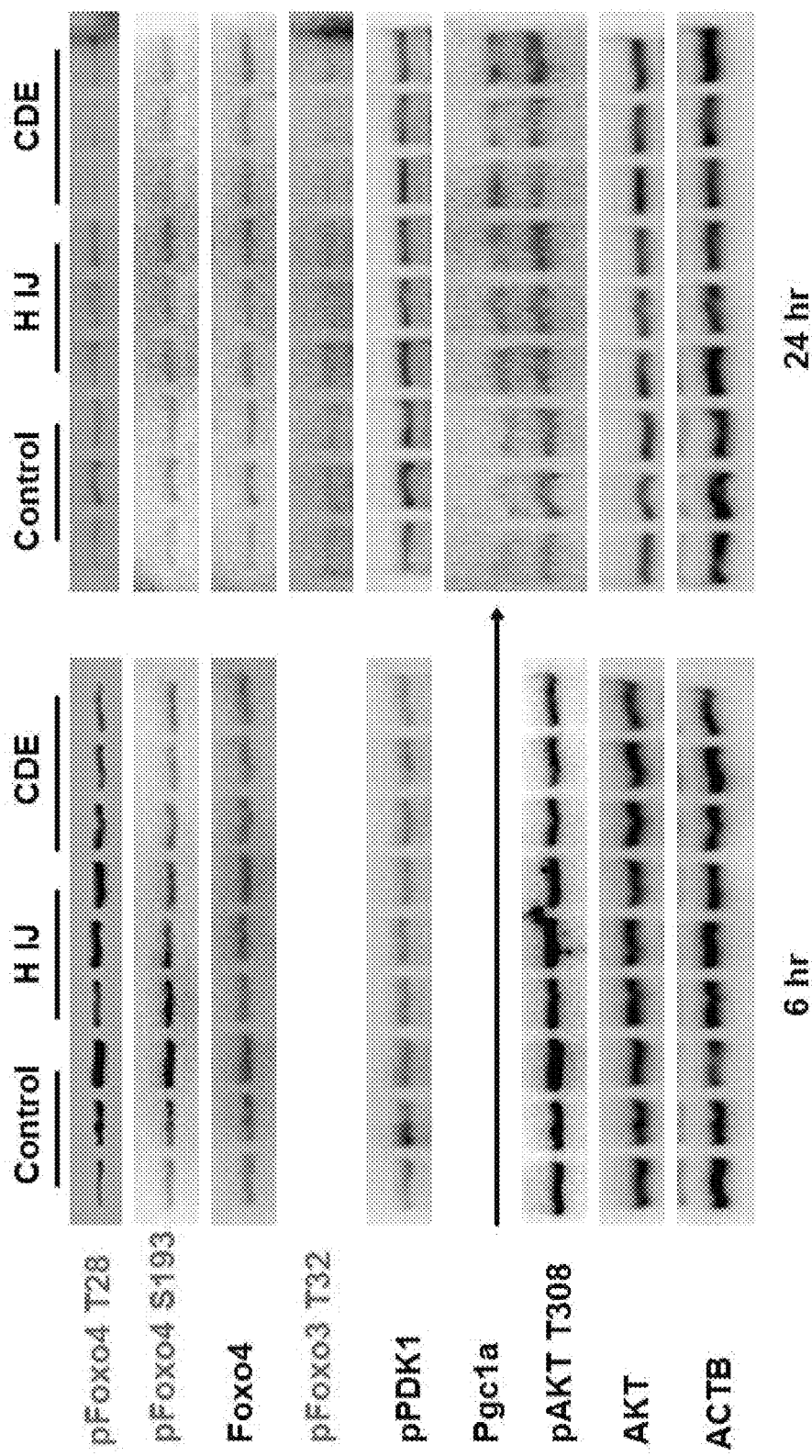
FIG. 13 shows reduced FOXO phosphorylation and increased PGC1a protein expression in human IMR-32 neuronal cells by the combination of compounds C (5'-Methylselenoadenosine), D (Se-Adenosyl-L-homocysteine), and E (Gamma-glutamyl-methylseleno-cysteine) (150 ppb of each compound).

Accordingly, we were interested to study if any of the CDE compounds could influence the expression of these potent signaling factors. As shown in FIG. 13, phosphorylation of Foxo4 and Foxo3 were downregulated in IMR-32 cells after treatment of CDE for both 6 and 24 hr, while PGC1a protein was increased in IMR-32 cells after 24 hr treatment. There were little or no effects on the protein expression of other tested signaling molecules. Enhanced PGC1a protein may promote MT biogenesis which may offer another explanation why MT potential was enhanced by the combination of CDE in IMR-32 cells (FIG. 3, top and middle panels). It is well characterized that dephosphorylation of FOXOs, such as Foxo 4 at T28 and S193, leads to nuclear localization of FOXO proteins. This result strongly suggests that the combination of CDE compounds likely will enhance nuclear FOXO action. Together our data suggest that CDE contain one or more Foxo activator(s) and positive PGC1a regulator(s) in neuronal cells.

This result may be very significant from a therapeutic perspective in neuronal cells, such as brain. It is well established that co-localization of certain FOXO proteins and PGC1a in the nucleus can lead to a potent activation of gluconeogenesis (glucose production). While such a situation would be undesirable in, say, the liver of a diabetic subject, it could be viewed as extremely favorable in the situation of a subject in early stage AD—where glucose import into the neuron is impaired and, consequently, the brain cell is starved of its primary fuel source. An enhanced ability to produce glucose from the carbon skeletons of other molecules would be very beneficial, in such circumstances.

To test whether the observed activation of FOXO and PGC1a (above) is neuronal cell-specific, we also examined their protein levels in mouse liver AML-12 cells. Protein extracts were prepared from liver cells at the same time and the same experimental conditions as IMR-32 cells. However, the effects noted in liver cells (FIG. 15) described in a later section were quite opposite those obtained for IMR-32 cells and certainly suggest that the dephosphorylation of FOXO and the upregulation of PGC1a by CDE is not a tissue-wide phenomenon and may be restricted to neuronal cells.

Compound C, a Neuronal-Specific FOXO Activators and a PGC1a Upregulator

As described above, CDE compounds together brought about the dephosphorylation of FOXOs and stimulated PGC1a protein expression (FIG. 13). To identify which compound in the CDE mixture has these effects, we examined the expression of the aforementioned proteins in C-, D- and E-treated IMR32 cells. As shown in FIG. 14A, pFOXO4 levels were decreased dramatically in IMR32 cells after 6 hr treatments of all three compounds. After 24 hr treatment, decreased pFOXO4 T28 levels were also observed in C- and E-, but not D-, treated IMR-32 cells. Quantitative analysis showed that the decrease of pFoxo4 levels in IMR-32 cells by C, D, and E at 6 hr treatment, and by C and E at 24 hr treatment was statistically significant (FIG. 14B-C).

Figure 14:
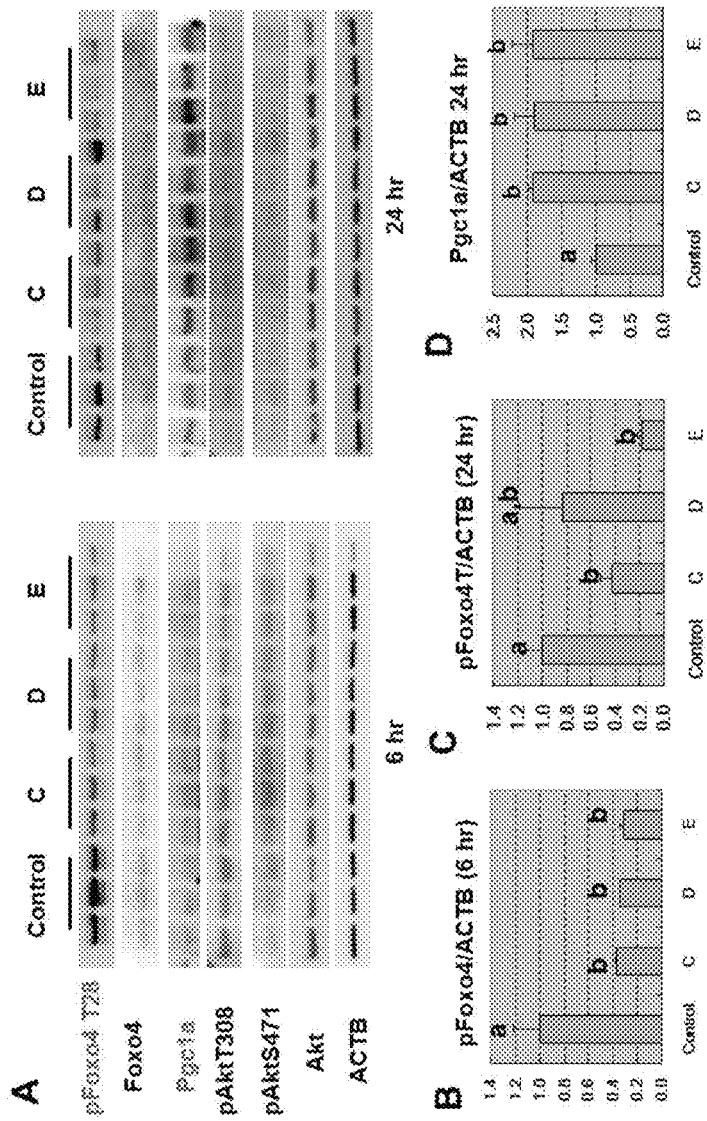
FIG. 14 shows a western blot analysis of various other signaling molecules including phosphorylated forkhead box protein O4 phosphorylated at threonine 28 ("pFOXO4 T28"), forkhead box protein O4 ("FOXO4"), phosphorylated murine thymoma viral oncogene homolog 1 at threonine 308 ("pAktT308"), phosphorylated murine thymoma viral oncogene homolog 1 at serine 471 ("pAktS471"), Akt, and peroxisome proliferator activated receptor gamma coactivator 1 alpha ("PGC1a") in IMR-32 neuronal cells treated with compounds C (5'-Methylselenoadenosine), D (Se-Adenosyl-L-homocysteine), or E (Gamma-glutamyl-methylseleno-cysteine), each compound at 150 ppb. (A) Photographs of Western blots. (B-C) Quantitative analysis of phosphorylated forkhead box protein O4 at threonine at position 28 (pFoxo4 T28) in the above Western blots of AML-12 cells treated with the listed compounds for (B) 6 and (C) 24 hours. Data are presented as mean±sem of 3 samples. Different letters (a vs. b) in the bar graphs means a significant difference between those two groups (P<0.05). The letters "a,b" denote no significant difference from a or b.

It is important to note that neither the CDE combination nor the individual C, D or E treatments brought about any change in total FOXO levels (FIGS. 13 and 14), but rather just changed the control of FOXO action by dephosphorylating it. Reduced FOXO phosphorylation was unlikely due to the down-regulation of AKT phosphorylation, as pAKT protein levels were not visibly decreased in C-, D- or E-treated cells (FIG. 14A). Also, pElf2beS539 protein level was also not affected by C, D or E, indicating that these compounds likely did not affect protein translation in neuronal cells (FIG. 14A). In contrast, PGC1a protein levels were markedly elevated after 24 hr treatment of all three compounds (FIG. 14A, 14D), which may explain why MT potential was upregulated by these compounds in IMR-32 cells (FIG. 3 top and middle panels). Together, our data suggest that compound C and E are FOXO activators and PGC1a upregulators, while compound D is a PGC1a upregulator and have mixed effects in the regulation of FOXO phosphorylation.

Discussion

Figure 12:
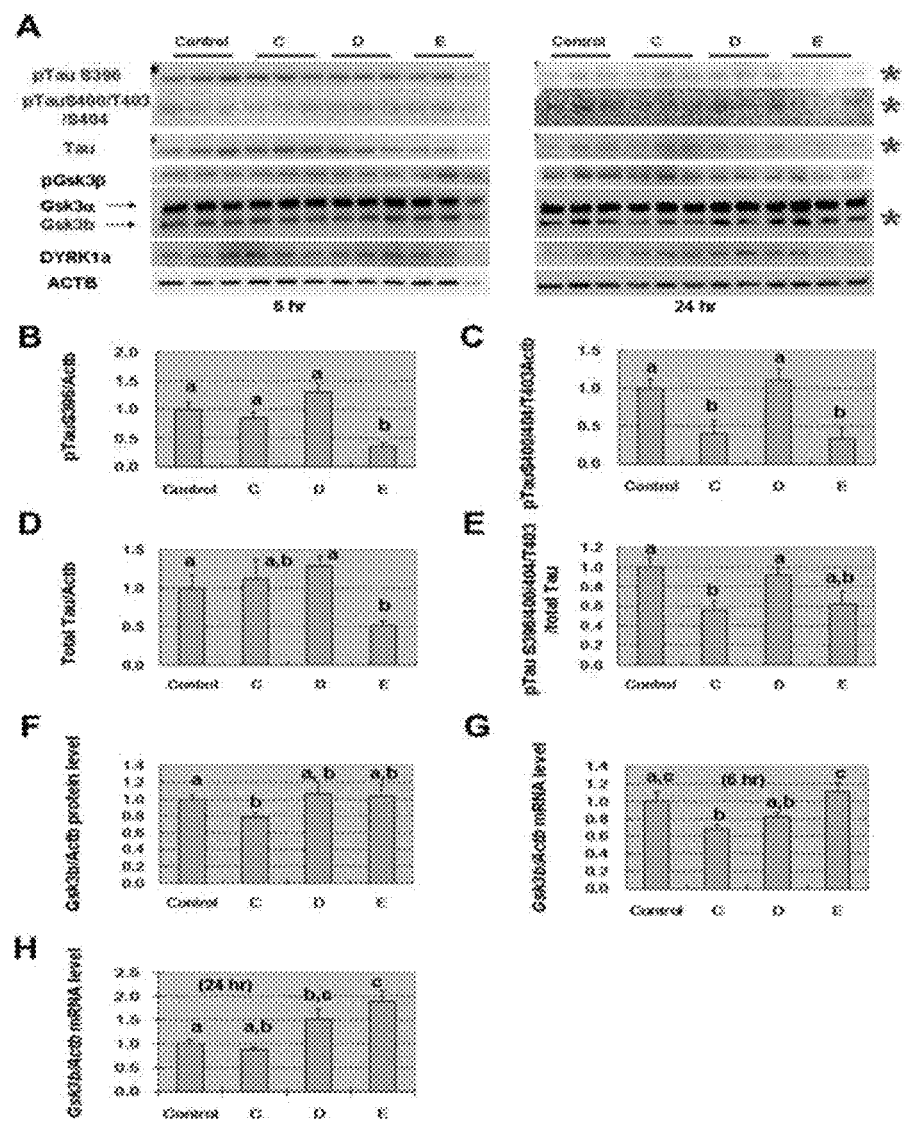
FIG. 12 shows that Compound C (5'-Methylselenoadenosine) is a novel inhibitor of Tau phosphorylation, and a glycogen synthase kinase 3 beta ("GSK3b") downregulator as determined by Western blot and RT-PCR analyses. (A) Photographs of Western blot analysis of various proteins (key for tangle formation in AD) in human IMR-32 neuronal cells treated with 150 ppb compound C (5'-Methylselenoadenosine), D (Se-Adenosyl-L-homocysteine), or E (Gamma-glutamyl-methylseleno-cysteine) for 6 and 24 hours. (B-E) Quantitative analysis of (B) phosphorylated Tau at serine residue at position 396 ("pTau S396") and (C) phosphorylated Tau at serine residue at serine residue at position 400, at threonine residue at position 403, and serine residue at position 404 ("pTau S400/T403/S404"), (D) total Tau, and (E) combined pTauS396 and pTau S400/T403/S404 per total Tau protein levels in the above Western blots (after 24 hr treatment, right panels). Data are presented as mean±sem of 3 samples. (F) Quantitative analysis of GSK3b protein levels in the above Western blots of IMR-32 cells treated with water vehicle (control) or compounds for 24 hours). Data are presented as mean±sem of 3 samples. (G-H) Quantitative RT-PCR analysis of GSK3b mRNA expression in human IMR-32 neuronal cells treated with water vehicle (control) and the listed compounds for (G) 6 and (H) 24 hours. Data are presented as mean±sem of 4 samples. Different letters (a vs. b, a vs. c, or b vs. c) in the bar graphs means a significant difference between those two groups (P<0.05). The letters "a,b" or "b,c" denote no significant difference from a or b or c.

When viewed in their totality, our results in neuronal cells put compound C as the favored agent for eliciting beneficial effects in these cells. While the results described directly above show that all three compounds are capable of bringing about dephosphorylation of FOXO and upregulation of PGC1a—very desirable effects from an energetic standpoint in neuronal cells, it should be recalled that compound C is the only candidate which elicits these FOXO/PGC1 effects and, at the same time, significantly reduces PSEN and Nicastrin levels (FIG. 11). Furthermore, it was the compound which demonstrated a favorable response in terms of reducing phospho-Tau levels and GSK3b levels in IMR-32 cells (FIG. 12).

As such, Compound C appears to be the compound of choice for eliciting a triad of beneficial effects in neuronal cells, as follows; 1) a beneficial impact on mitochondrial activity and function, by stimulating overall mitochondrial potential, increasing PGC1 levels and decreasing FOXO phosphorylation—thus allowing it nuclear access, 2) an implied effect in reducing amyloid build-up by decreasing the expression of PSEN1 and Nicastrin and, 3) an implied effect of reduced Tau tangle formation by reducing levels of phosphorylated Tau and the enzyme (GSK3b) which is thought to be responsible for Tau phosphorylation.

Figure 15:
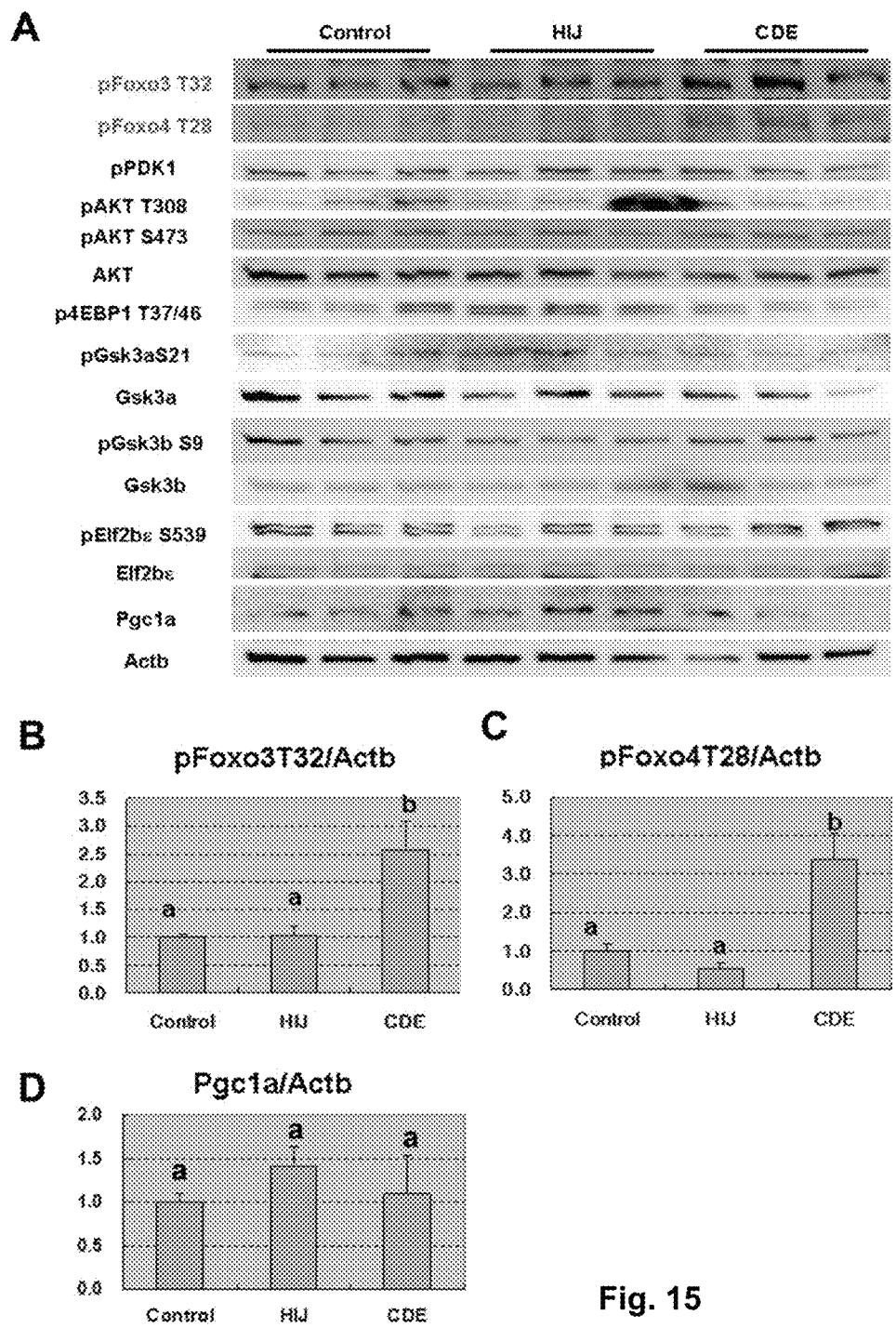
FIG. 15 shows a Western blot analysis of various other signaling molecules including FOXOs, PDK1, AKT, Gsk3a/b, 4EBP1, Elf2be, and PGC1a in mouse liver AML-12 cells treated with a combination of C (5'-Methylselenoadenosine), D (Se-Adenosyl-L-homocysteine), and E (Gamma-glutamyl-methylseleno-cysteine) (each compound at 150 ppb) for 6 hours. (A) Photographs of Western blots. (B-C) Quantitative analysis of (B) phosphorylated Foxo3 at T32, and (C) phosphorylated Foxo4 at T28 in AML-12 cells shown in the above Western blots. Data are presented as mean±sem of 3 samples. Different letters (a vs. b) in the bar graphs means a significant difference between those two groups (P<0.05).

Once again, to test the cell-specificity of these effects, protein extracts from a combination of CDE-treated liver AML-12 cells were probed with the same antibodies to detect differences in FOXO phosphorylation and PGC1a levels. As shown in FIGS. 15 and 16, and discussed in more detail in a later section, the effects seen with the three respective compounds confirmed that the IMR-32 cell effects were certainly not observed in liver. In fact, one could say that directly opposing effects were noted; namely, increased FOXO phosphorylation (nuclear exclusion), no change in PGC1a levels and no change in GSK3b levels. As will become clear, however, these are the type of effects one would wish to see happening in liver, especially in the case of a diabetic subject where hepatic glucose output needs to be controlled. Most importantly, it was found that, completely unlike neuronal cells, liver AML-12 cells did not respond to treatment with the individual compounds and, instead, only responded to the C,D,E mixture. Once again, this points to very definite cell-specificities and unanticipated cellular responses in relation to the mode of action of these compounds.

Results and Discussion: Liver Cells

Liver Cell-Specific and PDK1/AKT-Independent Upregulation of FOXO Phosphorylation by Compound CDE in Combination but not by Individual Compounds or their Sulfur Analogs As was the case with IMR-32 neuronal cells, the observations that selenium compounds (CDE combination, in this case) enhanced MT activity and modulated the expression of a key gene controlled in cellular energetic (UCP2) prompted us to look for effects which this combination of selenium compounds might have on other critical genes involved in liver energy metabolism, insulin signaling and cell proliferation. Accordingly, Western blot analyses were performed on CDE-treated AML-12 cells.

As described previously, FOXOs are major signaling molecules for gluconeogenesis and insulin sensitivity in the liver. It will be recalled that the functionality of FOXO proteins is governed by their state of phosphorylation. Phosphorylation of FOXOs excludes them from the nucleus, thereby essentially inactivating them. Dephosphorylation allows entry of FOXO proteins into the nucleus where they can participate in transcriptional regulation of several key genes concerned with energy metabolism. As shown in FIG. 15A, the phosphorylated forms of FOXO3 and 4 (pFOXO3 and pFOXO4 protein levels) were found to be significantly elevated in AML-12 cells after treatment of CDE, but not HU, for 6 hr. Quantitative analysis showed there was approximately a 2.5-fold increase of pFoxo3 and about a 3.2-fold increase of pFoxo4 in CDE-treated AML-12 cells (FIG. 15B-C). As phosphorylation of FOXOs causes nuclear exclusion to inactivate FOXO in the nucleus, our results suggest that CDE will function as FOXO inactivators in liver cells. As increased FOXO phosphorylation was not observed in CDE-treated IMR-32 neuronal cells in analyses that were performed at the same time and under the same experimental conditions (see the above FIG. 13), we can conclude that the inactivation of FOXO by CDE is liver-cell specific.

Together, our results suggest that the combination of CDE will function as novel liver cell-specific FOXO inactivators. In fact, in IMR-32 neuronal cells, a marked and highly significant activation (dephosphorylation) of FOXO proteins occurred in response to the single or combination of selenium compounds C, D and E. Thus, what we have in the case of these particular compounds is the ability to selectively activate FOXO proteins in neuronal cells and inactivate them in liver cells. The overall importance and novelty of this finding becomes apparent when one considers it in the context of glucose handling in Type-2 diabetes and Alzheimer's disease.

As a brief background, in its activated or unphosphorylated state FOXO resides in the nucleus where it binds to the promoter region for glucose 6-phosphatase and, together with other factors such as PGC-1a, increases transcription of glucose-6-phosphatase, thereby increasing the rate of glucose production. Glucose 6-phosphatase catalyzes the last step in gluconeogenesis and glycogenolysis causing the release of glucose from the liver. It is, therefore, critically important in the control of glucose homeostasis, particularly in diabetic subjects. Normally, the process of FOXO phosphorylation is controlled directly by another kinase enzyme called AKT (Protein Kinase B). AKT phosphorylates FOXO and drives it from the nucleus, thereby decreasing glucose production via a decreased rate of transcription of glucose 6-phosphatase. AKT itself is under upstream control by a mini molecular cascade reaction, which starts with insulin binding to its receptor at the cell surface. This initiates a series of events involving two other kinase enzymes, Phosphatidylinositol 3-kinase (PI3K) and Phosphoinositide-dependent protein kinase 1 (PDK1). The overall pathway is known as the Insulin/PI3K/PDK1/Akt pathway and it has the job controlling glucose homeostasis via insulin signaling. In the context of FOXO control, PDK1 phosphorylates and activates Akt which, in turn, phosphorylates and inactivates FOXO.

Since PI3K/PDK1/AKT is the major signaling pathway upstream of FOXO for the insulin-mediated control of glucose production in the liver, we asked whether enhanced FOXO phosphorylation by CDE is due to the activation of PI3K/Pdk/Akt signaling pathway in liver cells. To test this, we examined the protein levels of pPDK1, pAKT T308 and 5473 and total AKT in CDE-treated liver cells. Surprisingly, CDE did not affect the phosphorylation of PDK1, AKT, or total AKT levels (FIG. 15A). We also examined levels of two other downstream signaling molecules pGSk3a and pGSK3b which are directly controlled by AKT, and did not observe any change in their protein levels (FIG. 15A), which is consistent with no change of pAKT in CDE-treated cells. The levels of p4Ebp (a downstream molecular target of AKT/mTor signaling) and pElf2be 5539 (a downstream molecular target of Gsk3) that are key for insulin-driven protein synthesis or translation were also not affected (FIG. 15A). This provides additional direct molecular evidence that CDE did not have a toxic effect in affecting liver cell proliferation/survival as described earlier.

As described in the context of neuronal IMR-32 cells, PGC1a is a critical gene for MT biogenesis and carbohydrate metabolism. In liver cells, it also acts in concert with FOXO to drive the transcription of genes involved in gluconeogenesis, but cannot do this in the nuclear absence of FOXO. We examined PGC1a protein expression, and did not observe a significant change of PGC protein level in liver cells after the combination of CDE treatment by quantitative analysis (FIGS. 15A and D). However, due to the robust effect noted on FOXO phosphorylation in response to CDE, it is almost certain that it would be excluded from the nucleus and, hence, the level of PGC1a becomes of low importance because it requires FOXO to initiate the gluconeogenic process. Together, these results suggest that CDE did not affect PI3k/PDK1/AKT signaling and several other AKT direct or indirect downstream signaling molecules, except the above described but critical FOXOs. In other words, CDE can selectively inactivate FOXOs and this action appears to be independent on the PI3K/PDK1/AKT signaling in the liver cells.

In essence, therefore, the mode of action of CDE in liver cells may be totally independent of the insulin-driven PI3k/PDK1/AKT signaling pathway, i.e. it may be insulin-independent. The importance of this becomes immediately obvious to anyone skilled in the art of metabolic signaling pathways because it lessens the physiological consequences of a liver cell becoming insulin-resistant, in the context of controlling hepatic glucose output. Bypassing insulin signaling while still being able to control glucose homeostasis through FOXO regulation opens up many therapeutic possibilities for the treatment of diabetes in general; making it less dependent on the administration of exogenous insulin.

In addition, the importance of finding a potentially AKT-independent FOXO inhibitor in liver should not be underestimated from a broader health perspective. It is well established that the PI3k/PDK1/AKT pathway is the prototypic pathway that promotes cell growth and is constitutively active in many cancers. AKT, when activated, performs critical roles in diverse cellular processes—not just glucose homeostasis through FOXO inactivation. Chief among these other pathways is cancer progression. In this respect, it is of interest to note that AKT was originally identified as the oncogene in the transforming retrovirus AKT8. Thus, any compound which can perform a key role of AKT, but do it in an AKT-independent fashion is both very novel and valuable.

Once again, to complete our investigations into compound specificity, we wished to determine if the single compounds in CDE had the ability to inactivate FOXOs in liver cells, AML-12 cells were treated with individual compounds under the same experimental conditions. Western blot analysis showed that the inactivation of FOXO (indicated by increased pFOXOs) was not observed in individual compound-treated liver cells after 6 or 24 hr treatment (FIG. 16). We also examined a number of other signaling molecules and did not observed the increased phosphorylation of AKT, Gsk3a/b and Elf2be in the liver cells after treatment with C, D, or E for 6 or 24 hr (FIG. 16). The only effects noted had to do with compound E which appeared to slightly reduce the levels of pAKT and pElf2bε S539 in AML-12 cells after 6 hr treatment (FIG. 16). The effect on AKT by compound E, however, must be marginal since this was not reflected by a compound E-mediated decrease in phosphorylation of FOXOs (the immediate downstream target of AKT). As such, this does not indicate a significant change in gluconeogenic potential in E-treated cells. Dephosphorylation of EIF2bε may signify an increased level of mRNA/Protein translation, but this has not been thoroughly explored. However, it is clear that the protein expression of the species tested in these Western blots was not altered by any of these three selenium compounds (FIG. 16). Regardless, our results suggest that the individual selenium compounds C, D or E alone did not increase FOXO phosphorylation in liver cells. Therefore, there exists a synergistic effect among C, D and E compounds to inactivate FOXO in liver cells.

Together, our results suggest that CDE, but not individual compounds, will function as liver cell-specific and PI3K/PDK/AKT-independent FOXO inactivators.

Downregulation of the Expression of G6pc, a FOXO Downstream Target for Glucose Production, in AML-12 Cells after Treatment with Compound CDE Selenium Compounds As mentioned above, Glucose 6-Phosphatase, Catalytic subunit (G6PC) is a direct downstream target of FOXO which enhances glucose production, especially in the liver. Enhanced levels of pFOXOs (inactive) in CDE-treated liver cells suggests that CDE can play a role in controlling glucose production and in improving insulin sensitivity in liver cells. The real proof that the selenium compound combination, CDE, can modulate gluconeogenesis or glycogenolysis through FOXO phosphorylation, would be to see a decreased expression of G6PC in a hepatic environment. To test this hypothesis, we examined G6pc expression in liver cells by quantitative RT-PCR analysis.

Figure 17:
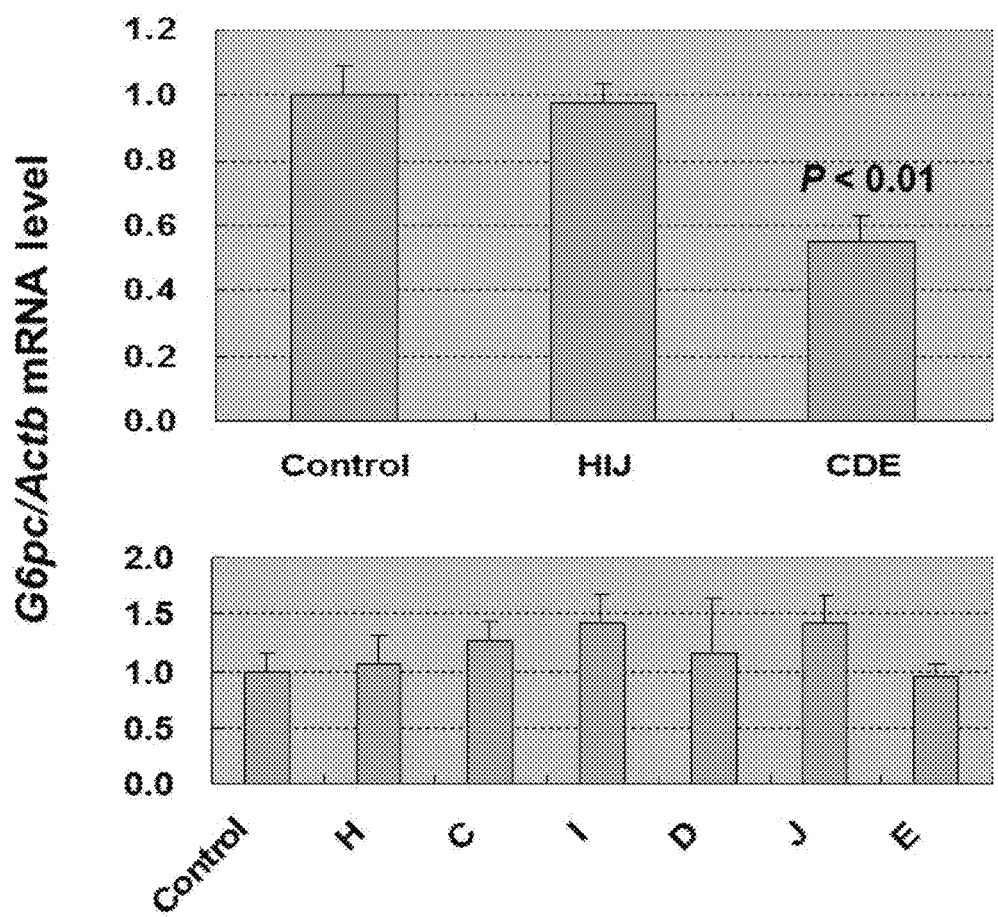
FIG. 17 shows glucose 6 phosphatase catalytic subunit ("G6pc") expression in mouse liver AML-12 cells is significantly downregulated by the combination of compounds C (5'-Methylselenoadenosine), D (Se-Adenosyl-L-homocysteine), and E (Gamma-glutamyl-methylseleno-cysteine), but not by the individual compounds. Cells were treated with vehicle (control), individual selenium compound (150 parts per billion (ppb) or the combination of CDE (150 ppb of each compound) as well as their respective sulfur analog(s) for 48 hour, and then subjected to quantitative RT-PCR. Data are presented as mean±sem of four samples in the bar graph.

As shown in FIG. 17, treatment of AML-12 liver cells with the CDE combination, but not the HIJ sulfur analog combination caused a very significant 45% decrease in G6pc expression in liver cells. In addition, we also examined G6pc expression in AML-12 cells after treatment with all of the individual compounds, and did not observed any significant alteration (increase or decrease) in G6pc expression (FIG. 17); a finding consistent with the unchanged FOXO phosphorylation levels noted in compound-, D- or E-treated liver cells, as determined by Western blot analysis (FIG. 16). The effect of decreased G6pc expression in response to the CDE combination was observed in three repeat experiments using different batches of cells (data not shown).

Together, our results demonstrate that CDE, but not the individual compounds, can significantly attenuate G6pc expression, thereby representing a novel way to reduce hepatic glucose output. Our collective findings further point to the mode of action of these compounds being mediated by an AKT-independent increase in FOXO phosphorylation. These data provide strong in vitro evidence that CDE has significant potential in a therapeutic capacity for controlling hepatic glucose output in obese and type-2 diabetic subjects.

Overall Summary and Discussion

We have identified that compound C, but not D, enhanced MT potential in kidney cells, and that both compound C and D enhanced MT potential in mouse skeletal muscle myoblast C2C12 cells. These results suggest that compound C may be useful against progressive kidney failure, and C and D against sarcopenia caused by progressive loss of MT function in the kidney or skeletal muscle. In the case of skeletal muscle, we also expect C and D to be potentially useful in the area of T2DM research and control, given that skeletal muscle utilizes 75-80% of daily ingested glucose and that mitochondrial dysfunction in skeletal muscle is believed to be a key initiator of T2DM.

In addition, our experiments using human neuronal IMR-32 cells indicate that one of these compounds in particular (compound C) may be uniquely against AD pathogenesis. This conclusion is based on the following key findings:

(1) MT potential transiently enhanced by C (FIG. 3)
(2) Improved neuronal cell survival by compound C (FIG. 5)
(3) Neuronal cell-specific downregulation of FOXO phosphorylation (key for cell metabolism) and upregulation of PGC1a (key for MT biogenesis) (FIG. 14 vs liver cell data in FIG. 16);
(4) Selective targeting of the gamma-secretase complex genes PSEN and Nicastrin to inhibit their expression for APP cleavage (FIG. 11);
(5) Inhibition of Tau phosphorylation likely against tangle formation in AD (FIG. 12); and
(6) Neuronal cell-specific GSK3b downregulation which, again indicates reduces Tau phosphorylation potential and reduced tangle formation in AD situations (FIG. 12 vs liver cell data FIG. 16).

Figure 8:
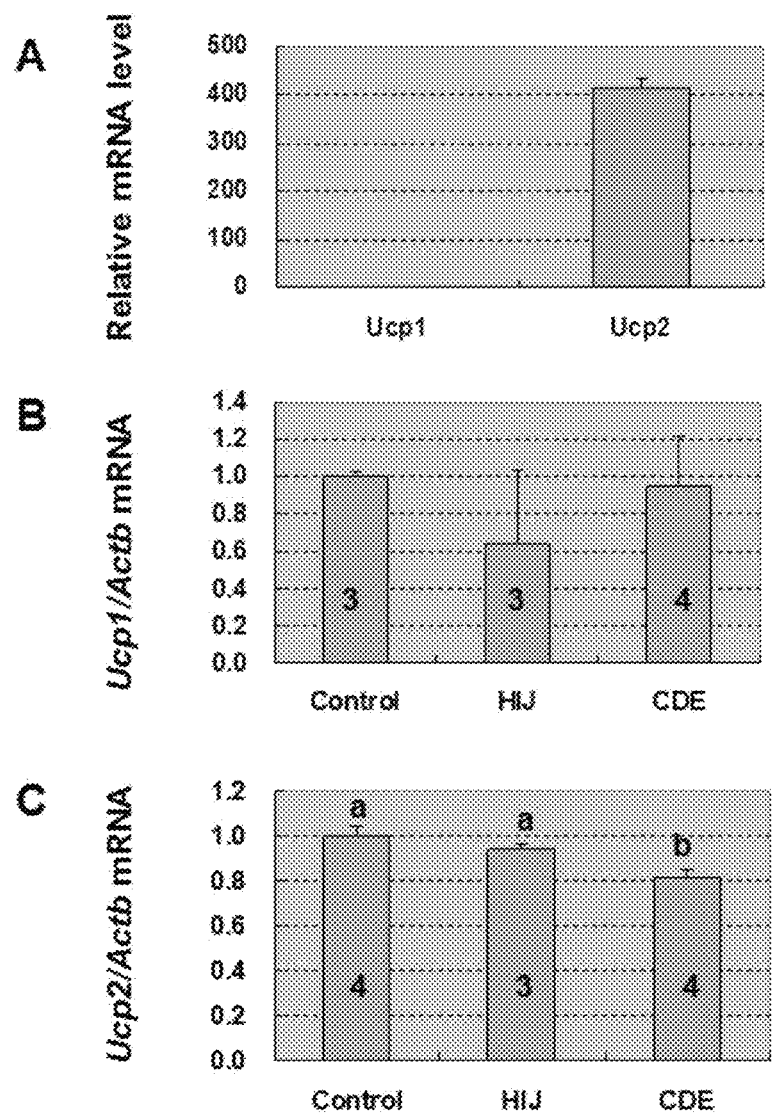
FIG. 8 shows predominant expression of mitochondrial Uncouple Protein 2 (Ucp2) in AML-12 mouse liver cells, and downregulation of its expression by the combination of compounds C (5'-Methylselenoadenosine), D (Se-Adenosyl-L-homocysteine), and E (Gamma-glutamyl-methylseleno-cysteine) (150 ppb of each compound)(A) Relative expression of mitochondrial Uncouple Protein 1 (Ucp1) and Ucp2 in normal AML-12 cells (after treatment with water vehicle for 6 hours). n=4 as denoted in the bar. (B) No effect of the combination of C (5'-Methylselenoadenosine), D (Se-Adenosyl-L-homocysteine), and E (Gamma-glutamyl-methylseleno-cysteine) on Ucp1 expression. (C) Ucp2 expression downregulated by the combination of C (5'-Methylselenoadenosine), D (Se-Adenosyl-L-homocysteine), and E (Gamma-glutamyl-methylseleno-cysteine). Data are presented as mean±sem of denoted number of sample in each bar. Different letters (a vs. b) in the bar graph means a significant difference among those groups (P<0.05).

We have identified a novel liver cell-specific and PI3K/PDK1/AKT-independent FOXO inactivation compound combination (CDE) (i.e., the combination of CDE, but not the individual compounds). This combination of compounds dramatically downregulates G6pc expression in liver cells through the nuclear exclusion of FOXO proteins. We envisage that this combination may be particularly useful in the research and amelioration of symptoms and pathologies arising from metabolic syndrome, obesity and T2DM. Our reasoning is based on the following findings:

(1) MT potential is significantly enhanced in liver cells by a combination of CDE only; not any other compound or their combinations. (FIG. 7);
(2) There was no toxic effect on the survival of liver cells or neuronal cell (FIG. 5, FIG. 9)
(3) The Uncoupling Protein 2 (Ucp2) gene was specifically and significantly downregulated by CDE (FIG. 8); Of particular note in this regard are the findings from recent studies that inhibition of UCP2 expression reverses diet-induced diabetes by affecting both insulin secretion and action.
(4) Liver cell-specific FOXO was inactivated ((phosphorylated) by CDE (FIG. 15 vs neuronal cell data FIG. 13);
(5) No effect on FOXO inactivation by individual compounds was noted (FIG. 16)
(6) No effect on phosphorylation of PI3K/PDK/Akt signaling by CDE was noted (FIG. 15). This indicates that CDE represents a novel AKT-independent FOXO inactivator.

(7) Significant downregulation of the critical FOXO target gene G6pc by CDE (FIG. 17) but not by any of the individual compounds (FIG. 17). It will be recalled that hepatic glucose output is controlled by FOXO-mediated activation of G6pc transcription.

Figure 18:
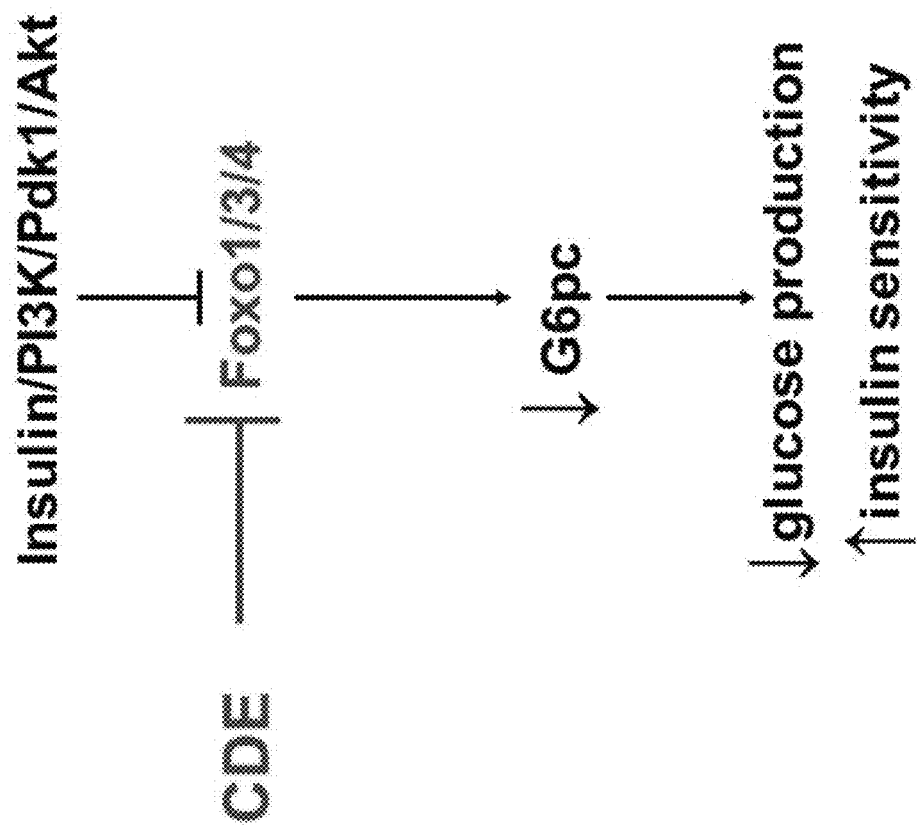
FIG. 18 shows a schematic representation of the combination of compounds CDE in the regulation of G6pc expression in liver cells.

Based on the above experimental data, we believe that the CDE combination can specifically act as a potent FOXO inactivator in liver cells to reduce G6pc expression and lower hepatic glucose output. Furthermore, we have shown that this action is independent of PI3K/PDK/Akt signaling. A depiction of how this process may work is shown in FIG. 18. Whereas, normally, FOXO phosphorylation and its subsequent entry or exclusion from the nucleus is governed by the Insulin/PI3K/PDK1/AKT pathway, we show that the specific combination of compounds C, D and E brings about the phosphorylation of FOXO by an as yet unidentified kinase enzyme. Phosphorylated FOXO, excluded from the nucleus, is unable to transcriptionally activate G6PC which leads, in turn, to reduced glucose output from the liver. Reduced hepatic glucose output and the associated decrease in blood glucose concentration will lead to an insulin-sparing effect, i.e. reduced demand on the pancreas to secrete insulin in response to high blood glucose.

It is also quite reasonable to expect that the lower level of blood glucose may lead to both enhanced insulin sensitivity in peripheral tissues and a more controlled release of insulin by the beta-cells of the pancreas. That is to say, insulin output by the pancreas will be less likely to be overtaxed, due to lower circulating glucose levels overall. From the experiments conducted and presented in this application, we have been unable to identify any negative effects on either the growth of all cell types tested or activation of pathways which may signal initiation of uncontrolled proliferation and growth, i.e. cancer causing. In fact, the ability of these compounds to bypass the AKT-signaling pathway (at least in liver) makes them particularly interesting from a reduced toxic potential viewpoint.

Figure 19A:
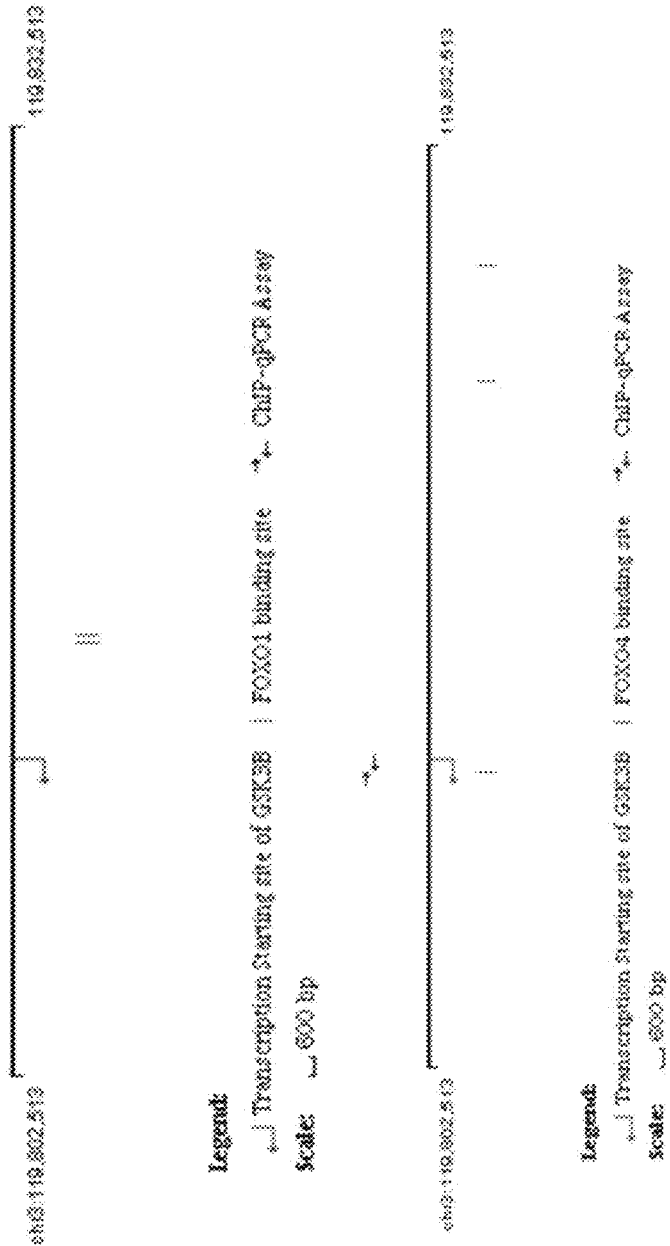
FIG. 19 shows the presence of Foxo binding motifs in the promoter regions of human GSK3B, PSEN, and NICASTRIN genes, as well as a schematic representation of the effect of compound C on the regulation of mediators important in plaque and tangle formation in neuronal cells. Panel (A) shows the location of five FOXO1/3/4 binding motifs on the human GSK3B promoter. Panel (B) shows the location of two FOXO1/3/4 binding motifs on the human PSEN promoter. Panel (C) shows the location of a FOXO1/3/4 binding motif on the human Nicastrin (NCSTN) promoter. Panel (D) shows the schematic representation of the effect of compound C on the regulation of mediators important in plaque and tangle formation in neuronal cells.
Figure 19B:
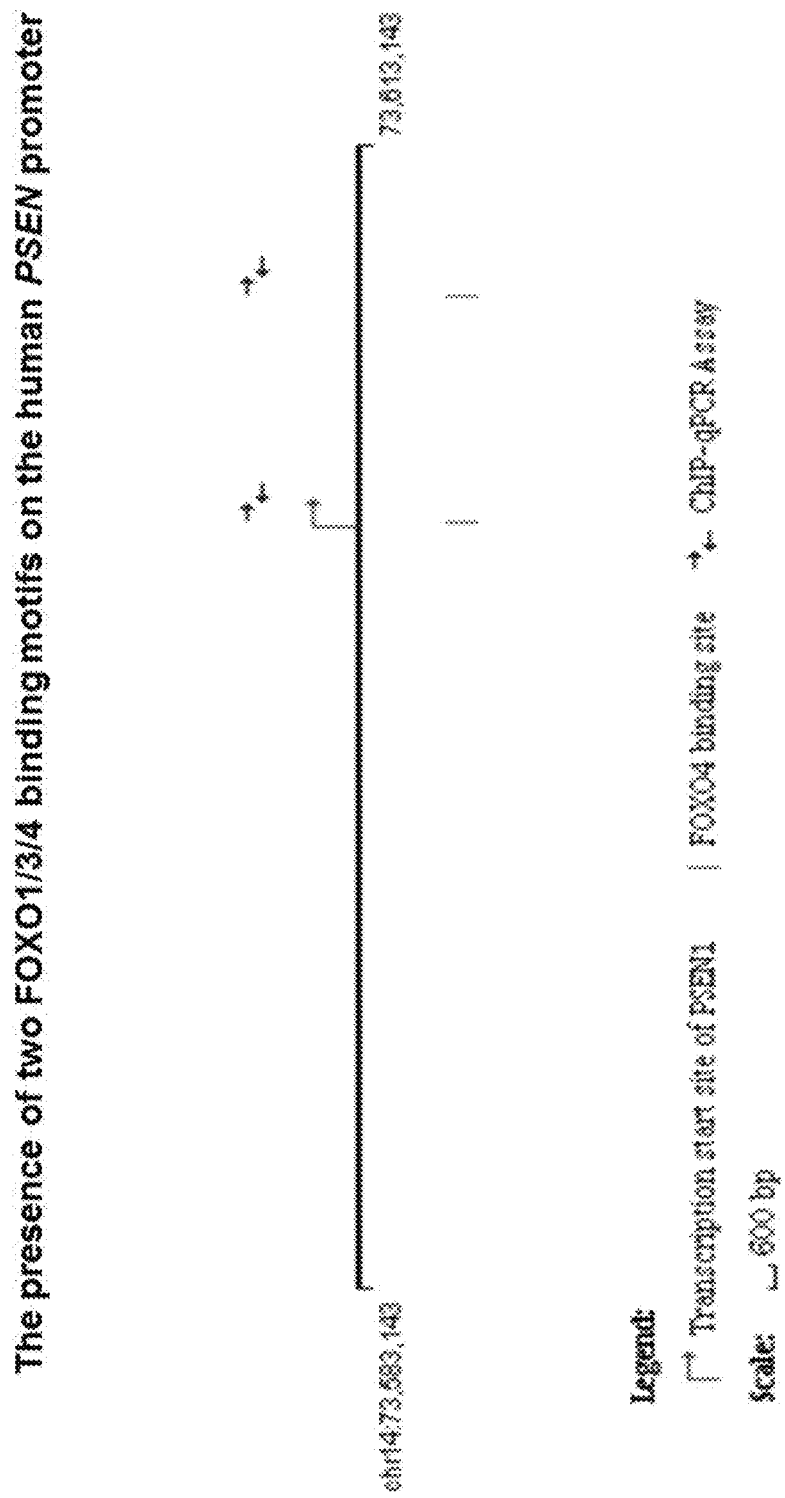
Figure 19C:
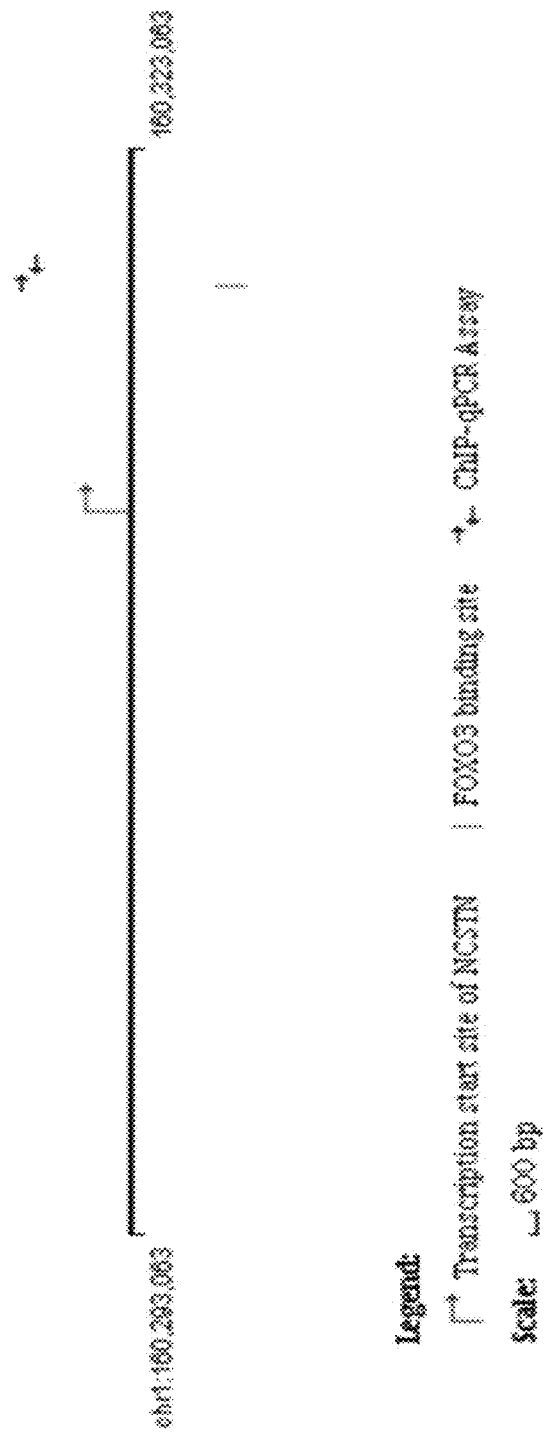
Figure 19D:
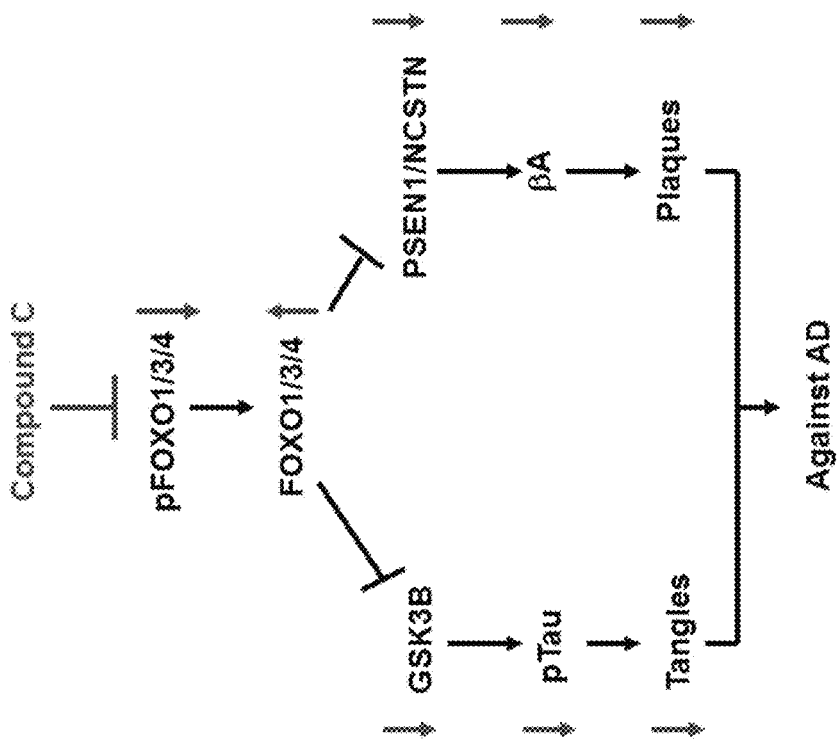

Based on the findings presented above, we also believe that we can hypothesize a plausible model for the effect of compound C, in particular, on ameliorating the impacts of the AD pathologies (Amyloid plaques and Tau tangles). As shown in FIG. 19A-C, the key AD-related genes whose expression is reduced or altered in IMR-32 cells have the binding motifs (sites) for FOXOs 1, 3 or 4 in their gene promoter regions. This is true for Gsk3b (FIG. 19A), Psen1 (FIG. 19B) and Nicastrin (FIG. 19C). This means that nuclear-localized FOXO proteins could bind to and negatively regulate transcription from these gene promoters. With this knowledge, it is thus quite easy to visualize a situation (FIG. 19D) where compound C dephosphorylates FOXO proteins and allows them into the nucleus. Here, the active FOXO proteins bind to and inhibit transcription from the promoter regions of the genes mentioned above. Lower levels of GSK3b in IMR cells (FIG. 12) will result in decreased phosphorylation of Tau, followed by decreased microtubule stabilization and decreased tangle formation as a direct result.

Likewise, binding of FOXO proteins to the promoter regions of PSEN and Nicastrin inhibits transcription from these genes which results in lower amounts of these critical gamma-secretase components being produced in neuronal cells. The natural implication of this would be lower levels of aberrant APP processing, lower amyloid-beta peptide concentration and decreased amyloid plaque burden as a result.

All publications and patents mentioned in the present application are herein incorporated by reference. Various modification and variation of the described methods and compositions of the present application will be apparent to those skilled in the art without departing from the scope and spirit of the present application. Although the present application has been described in connection with specific preferred embodiments, it should be understood that the present application as claimed should not be unduly limited to such specific embodiments. Indeed, various modifications of the described modes for carrying out the present application that are obvious to those skilled in the relevant fields are intended to be within the scope of the following claims.

The invention claimed is:

1. A method for enhancing mitochondrial function in one or more cells selected from the group consisting of skeletal muscle cell, neuronal cell, and combinations thereof, said method comprising:
    administering an effective amount of a composition to the one or more cells, the composition comprising a compound selected from the group consisting of 5'-Methylselenoadenosine, Se-Adenosyl-L-homocysteine, Gamma-glutamyl-methylseleno-cysteine, a compound of formula (I), a compound of formula (III), and combinations thereof, wherein the effective amount enhances mitochondrial function as compared to cells not treated with the composition,
    wherein the formula (I) is:

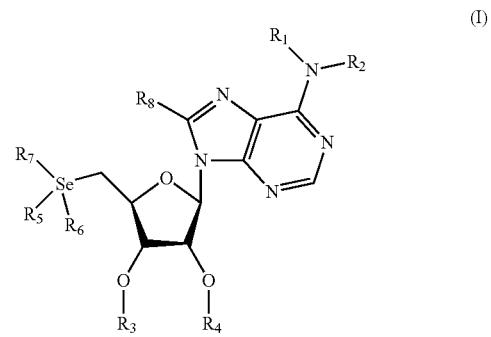

or a pharmaceutically acceptable salt, hydrate, or prodrug thereof, wherein
    $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;
    $R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;
    $R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;
    $R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_7$ is H, alkyl, alkenyl, alkynyl, ketone, amino alcohol, amino acid, OR', Se—R', S—R', where R' is selected from H, alkyl, cycloalkyl, aryl, aralkyl, or heterocyclyl;

$R_8$ is hydrogen, azido, alkyl, alkenyl, alkynyl; and wherein the formula (III) is:

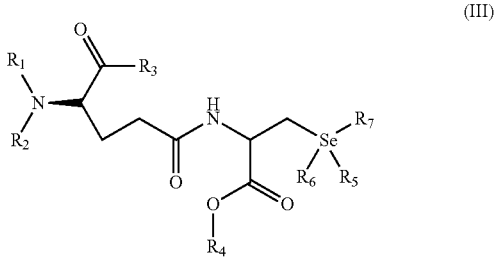

(III)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is OH, OR, alkoxy, aralkoxy, or amino, where R is selected from alkyl, cycloalkyl, aryl, aralkyl, heterocyclyl, or a pharmaceutically acceptable salt, or inner salt;

$R_4$ is H, alkyl, alkenyl, alkynyl, cycloalkyl, aryl, aralkyl, heterocyclyl, or a pharmaceutically acceptable salt, or inner salt;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl; and $R_7$ is H, alkyl, alkenyl, alkynyl, ketone, OR', Se—R', S—R', where R' is selected from H, alkyl, cycloalkyl, aryl, aralkyl, or heterocyclyl.

2. A method of claim 1, wherein the compound is isolated.

3. A method of claim 1, wherein the composition comprises 5'-Methylselenoadenosine.

4. A method of claim 3, wherein the compound is purified.

5. A method of claim 1, wherein the composition excludes one or more of glutamyl selenocysteine, methionine or selenomethionine.

6. A method of claim 1, wherein the effective amount is 200 micrograms or less per day.

7. A method of claim 1, wherein the composition is administered once daily.

8. A method of claim 1, wherein the 5'-Methylselenoadenosine, or a compound of formula (I) is a selenoglycoside.

9. A method for enhancing mitochondrial function in in one or more liver cells comprising:

administering an effective amount of a composition to the one or more liver cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount enhances mitochondrial function as compared to cells not treated with the composition, wherein the formula (I) is:

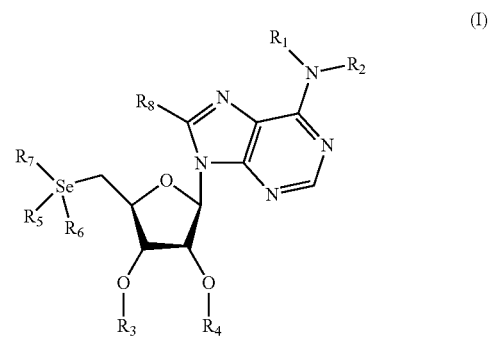

(I)

or a pharmaceutically acceptable salt, hydrate, or prodrug thereof, wherein $R_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or $R_1$ together with $R_2$ form a heterocyclic ring having 4 to 8 ring members with at least one heteroatom selected from oxygen or nitrogen;

$R_3$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_4$ is H, acyl, alkyl, alkenyl, alkynyl, aralkyl, cycloalkyl, carboxyl, or C-amido; or $R_3$ together with $R_4$ and the atoms to which they are attached form a heterocyclic ring having 4 to 8 ring members with at least one heteroatom selected from oxygen or nitrogen;

$R_5$ is oxo, hydroxyl, alkyl, alkenyl, alkynyl, OR', or is absent; where R' is selected from alkyl, alkenyl, alkynyl, cycloalkyl, aryl, or aralkyl;

$R_6$ is oxo, hydroxyl, alkyl, alkenyl, alkynyl, OR', or is absent; where R' is selected from alkyl, alkenyl, alkynyl, cycloalkyl, aryl, or aralkyl;

$R_7$ is H, alkyl, alkenyl, alkynyl, ketone, amino alcohol, amino acid, OR', Se—R', S—R', where R' is selected from H, alkyl, cycloalkyl, aryl, aralkyl, or heterocyclyl;

$R_8$ is hydrogen, azido, alkyl, alkenyl, alkynyl; and wherein the formula (III) is:

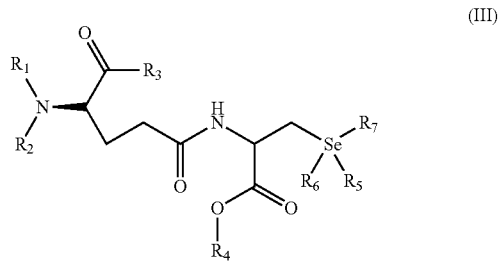

(III)

or a pharmaceutically acceptable salt, hydrate, or prodrug thereof, wherein
- R$_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_3$ is OH, OR, alkoxy, aralkoxy, or amino, where R is selected from alkyl, cycloalkyl, aryl, aralkyl, heterocyclyl, or a pharmaceutically acceptable salt, or inner salt;
- R$_4$ is H, alkyl, alkenyl, alkynyl, cycloalkyl, aryl, aralkyl, heterocyclyl, or a pharmaceutically acceptable salt, or inner salt;
- R$_5$ is oxo, hydroxyl, alkyl, alkenyl, alkynyl, OR', or is absent; where R' is selected from alkyl, alkenyl, alkynyl, cycloalkyl, aryl, or aralkyl;
- R$_6$ is oxo, hydroxyl, alkyl, alkenyl, alkynyl, OR', or is absent; where R' is selected from alkyl, alkenyl, alkynyl, cycloalkyl, aryl, or aralkyl; and
- R$_7$ is H, alkyl, alkenyl, alkynyl, ketone, OR', Se—R', S—R', where R' is selected from H, alkyl, cycloalkyl, aryl, aralkyl, or heterocyclyl.

10. A method of modulating glucose metabolism in one or more cells selected from the group consisting of liver cells, skeletal muscle cell, and combinations thereof said method comprising:
administering an effective amount of a composition to the one or more cells, the composition comprising at least three different compounds selected from the group consisting of 5'-Methylselenoadenosine, Se-Adenosyl-L-homocysteine, Gamma-glutamyl-methylseleno-cysteine, a compound of formula (I), and a compound of formula (III), wherein the effective amount modulates glucose metabolism in one or more cells as compared to cells not treated with the composition,
wherein the formula (I) is:

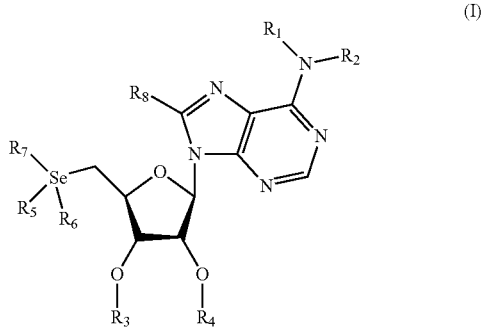

or a pharmaceutically acceptable salt, hydrate, or prodrug thereof, wherein
- R$_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_3$ is H, acyl, alkyl, alkenyl, alkynyl, aralkyl, cycloalkyl, carboxyl, or C-amido; or R$_3$ together with R$_4$ and the atoms to which they are attached form a heterocyclic ring having 4 to 8 ring members with at least one heteroatom selected from oxygen or nitrogen;
- R$_4$ is H, acyl, alkyl, alkenyl, alkynyl, aralkyl, cycloalkyl, carboxyl, or C-amido; or R$_3$ together with R$_4$ and the atoms to which they are attached form a heterocyclic ring having 4 to 8 ring members with at least one heteroatom selected from oxygen or nitrogen;
- R$_5$ is oxo, hydroxyl, alkyl, alkenyl, alkynyl, OR', or is absent; where R' is selected from alkyl, alkenyl, alkynyl, cycloalkyl, aryl, or aralkyl;
- R$_6$ is oxo, hydroxyl, alkyl, alkenyl, alkynyl, OR', or is absent; where R' is selected from alkyl, alkenyl, alkynyl, cycloalkyl, aryl, or aralkyl;
- R$_7$ is H, alkyl, alkenyl, alkynyl, ketone, amino alcohol, amino acid, OR', Se—R', S—R', where R' is selected from H, alkyl, cycloalkyl, aryl, aralkyl, or heterocyclyl;
- R$_8$ is hydrogen, azido, alkyl, alkenyl, alkynyl; and
wherein the formula (III) is:

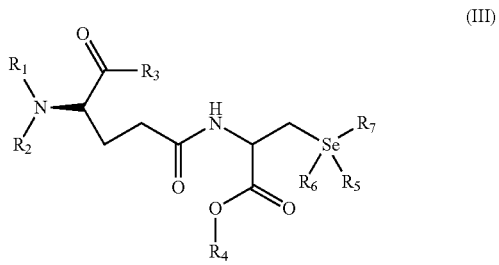

or a pharmaceutically acceptable salt, hydrate, or prodrug thereof, wherein
- R$_1$ is H, acyl, alkyl, alkenyl, alkynyl, aralkyl, carboxyl, cycloalkyl, C(O)R', C(O)OR', where R' is alkyl, alkenyl, alkynyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_2$ is H, acyl, alkyl, alkenyl, alkynyl, aralkyl, carboxyl, cycloalkyl, C(O)R', C(O)OR', where R' is selected from alkyl, cycloalkyl, aryl, aralkyl, or heterocyclyl; or R$_1$ together with R$_2$ form a heterocyclic ring having 4 to 8 ring members with at least one heteroatom selected from oxygen or nitrogen;
- R$_3$ is OH, OR, alkoxy, aralkoxy, or amino, where R is selected from alkyl, cycloalkyl, aryl, aralkyl, heterocyclyl, or a pharmaceutically acceptable salt, or inner salt;
- R$_4$ is H, alkyl, alkenyl, alkynyl, cycloalkyl, aryl, aralkyl, heterocyclyl, or a pharmaceutically acceptable salt, or inner salt;
- R$_5$ is oxo, hydroxyl, alkyl, alkenyl, alkynyl, OR', or is absent; where R' is selected from alkyl, alkenyl, alkynyl, cycloalkyl, aryl, or aralkyl;
- R$_6$ is oxo, hydroxyl, alkyl, alkenyl, alkynyl, OR', or is absent; where R' is selected from alkyl, alkenyl, alkynyl, cycloalkyl, aryl, or aralkyl; and $R_7$ is H, alkyl, alkenyl, alkynyl, ketone, OR', Se—R', S—R', where R' is selected from H, alkyl, cycloalkyl, aryl, aralkyl, or heterocyclyl.

\* \* \* \* \*